US012612438B2

(12) United States Patent
Yizhar et al.

(10) Patent No.: US 12,612,438 B2
(45) Date of Patent: Apr. 28, 2026

(54) BISTABLE TYPE II OPSINS AND USES THEREOF

(71) Applicant: Yeda Research and Development Co. Ltd., Rehovot (IL)

(72) Inventors: Ofer Yizhar, Rehovot (IL); Mathias Mahn, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 787 days.

(21) Appl. No.: 17/478,926

(22) Filed: Sep. 19, 2021

(65) Prior Publication Data

US 2021/0403518 A1 Dec. 30, 2021

Related U.S. Application Data

(63) Continuation of application No. PCT/IL2020/050330, filed on Mar. 19, 2020.

(30) Foreign Application Priority Data

Mar. 19, 2019 (IL) .......................................... 265486

(51) Int. Cl.
| | |
|---|---|
| *C07K 14/47* | (2006.01) |
| *A61K 38/00* | (2006.01) |
| *A61N 5/06* | (2006.01) |
| *A61P 25/00* | (2006.01) |

(52) U.S. Cl.
CPC ............... *C07K 14/47* (2013.01); *A61N 5/06* (2013.01); *A61P 25/00* (2018.01); *A61K 38/00* (2013.01); *A61N 2005/0658* (2013.01)

(58) Field of Classification Search
None
See application file for complete search history.

(56) References Cited

U.S. PATENT DOCUMENTS

| | | |
|---|---|---|
| 8,716,447 B2 | 5/2014 | Deisseroth et al. |
| 9,175,095 B2 | 11/2015 | Deisseroth et al. |
| 9,365,628 B2 | 6/2016 | Deisseroth et al. |
| 9,505,817 B2 | 11/2016 | Deisseroth et al. |
| 9,522,288 B2 | 12/2016 | Deisseroth et al. |
| 9,757,587 B2 | 9/2017 | Deisseroth et al. |
| 11,324,824 B2 | 5/2022 | Shemesh et al. |
| 2013/0347137 A1 | 12/2013 | Deisseroth et al. |
| 2016/0316730 A1 | 11/2016 | Deisseroth et al. |
| 2018/0154170 A1 | 6/2018 | Tonegawa et al. |
| 2018/0199850 A1 | 7/2018 | Lee et al. |
| 2019/0071476 A1 | 3/2019 | Deisseroth et al. |
| 2020/0179350 A1 | 6/2020 | During |
| 2022/0031864 A1 | 2/2022 | Lucas et al. |
| 2022/0280807 A1 | 9/2022 | Van De Ven et al. |
| 2023/0165938 A1 | 6/2023 | Lucas et al. |

FOREIGN PATENT DOCUMENTS

| | | | |
|---|---|---|---|
| CN | 106581056 | 4/2017 | |
| WO | WO 2013/090356 | 6/2013 | |
| WO | WO 2013/126521 | 8/2013 | |
| WO | WO-2013126521 A1 * | 8/2013 | .......... A61K 38/177 |
| WO | WO 2015/157761 | 10/2015 | |
| WO | WO 2020/188572 | 9/2020 | |
| WO | WO 2021/105509 | 6/2021 | |

OTHER PUBLICATIONS

Koyanagi et al. (Proc Natl Acad Sci U S A. Mar. 26, 2013;110(13):4998-5003) (Year: 2013).*
Gradinaru et al. (Cell. Apr. 2, 2010; 141(1): 154-165) (Year: 2010).*
Sato et al. (Nat. Commun. Mar. 28, 2018;9(1):1255) (Year: 2018).*
Invitation to Pay Additional Fees Dated Sep. 12, 2024 From the International Searching Authority Re. Application No. PCT/IL2024/050531. (3 Pages).
Atamian et al. "Human Cerebellar Organoids With Functional Purkinje Cells", Cell Stem Cell, 31(1): 39-51, Jan. 4, 2024.
Douglass et al. "Neural Basis for Fasting Activation of the Hypothalamic-Pituitary-Adrenal Axis", Nature, 620(7972): 154-162, Published Online Jul. 26, 2023.
Jaramillo Poulsen "Cholecystokinin Inputs Into the Lateral Periaqueductal Gray Drive Socially Enhanced Pain in Mice", Thesis Submitted With the Requirements for the Degree of Doctor of Philosophy, Department of Psychology, Bahvioural Neuroscience, University of Toronto, Canada, p. 1-184, 2024.
Labouesse et al. "A Non-Canonical Striatopallidal go Pathway That Supports Motor Control", Nature Communications, 14(1): 6712-1-6712-20, Published Online Oct. 23, 2023.
Zelmanoff et al. "Oxytocin Signaling Regulates Maternally-Directed Behavior During Early Life", BioRxiv Preprint, 2024: 1-88, Posted Feb. 15, 2024.
International Search Report and the Written Opinion Dated Jun. 26, 2020 From the International Searching Authority Re. Application No. PCT/IL2020/050330. (16 Pages).
Office Action and Search Report Dated Nov. 18, 2019 From the Israel Patent Office Re. Application No. 265486. (9 Pages).
Eickelbeck et al. "Lamprey Parapinopsin ('UVLamP'): A Bistable UV-Sensitive Optogenetic Switch for Ultrafast Control of GPCR Pathways", ChemBioChem Communications, 21(5): 612-617, Published Online Oct. 30, 2019.
Eickelbeck et al. "Optogenetic Approaches for Controlling Neuronal Activity and Plasticity", Handbook of In Vivo Neural Plasticity Techniques, XP0009520979, 28(Chap.16): 285-310, Jan. 2018.
Ellwardt et al. "Optogenetic Control of Intracellular Signaling: Class II Opsins", Optogenetics: A Roadmap, 133(Chap.4): 63-73, Published Online Oct. 25, 2017.

(Continued)

*Primary Examiner* — Sergio Coffa

(57) ABSTRACT

Bistable type II opsins are provided. Accordingly, there is provided a polypeptide comprising a bistable type II opsin and a heterologous ER export signal and/or membrane trafficking signal. Also provided are polynucleotides encoding same, cells expressing same and methods of use thereof.

5 Claims, 9 Drawing Sheets
(9 of 9 Drawing Sheet(s) Filed in Color)

Specification includes a Sequence Listing.

(56)                    References Cited

OTHER PUBLICATIONS

Gradinaru et al. "Molecular and Cellular Approaches for Diversi-fying and Extending Optogenetics", Cell, 141(1): 154-165, Apr. 2, 2010.
Isoldi et al. "Rhabdomeric Phototransduction Initiated by the Ver-tebrate Photopigment Melanopsin", Proc. Natl. Acad. Sci. USA, PNAS, 102(4): 1217-1221, Jan. 25, 2005.
Kawano-Yamashita et al. "Activation of Transducin by Bistable Pigment Parapinopsin in the Pineal Organ of Lower Vertebrates", PLoS ONE, 10(10): e0141280-1-e0141280-13, Oct. 22, 2015.
Kim et al. "Optogenetics: Lighting A Path From the Laboratory to the Clinic", Optogenetic: A Roadmap, 133(Chap.14): 277-300, Published Online Oct. 25, 2017.
Koyanagi et al. "Homologs of Vertebrate Opn3 Potentially Serve as A Light Sensor in Nonphotoreceptive Tissue", Proc. Natl. Acad. Sci. USA, PNAS, 110(13): 4998- 5003, Mar. 26, 2013.
Koyanagi et al. "Vertebrate Bistable Pigment Parapinopsin: Impli-cations for Emergence of Visual Signaling and Neofunctionalization of Non-Visual Pigment", Frontiers in Ecology and Evolution, 5(Art.23): 1-7, Published Online Apr. 11, 2017.
Sakai et al. "Diversity of Active States in TMT Opsins", PLoS ONE, 10(10): e0141238-1-e0141238-12, Oct. 22, 2015.
Sato et al. "Opn5L1 is a Retinal Receptor That Behaves as a Reverse and Self-Regenerating Photoreceptor", Nature Communications, XP055704703, 9(1): 1255-1-1255-10, Mar. 28, 2018.
Tsukamoto et al. "A Ciliary Opsin in the Brain of a Marine Annelid Zooplankton is UV-Sensitive and the Sensitivity is Tuned by a Single Amino Acid Residue", The Journal of Biological Chemistry, 292(31): 12971-12980, Published Online Jun. 16, 2017.
Wiegert et al. "Silencing Neurons: Tools, Applications, and Experi-mental Constraints", Neuron, 95(3): 504-529, Aug. 2, 2017.

Yizhar et al. "Optogenetics in Neural Systems", Neuron, 71(1): 9-34, Jul. 14, 2011.
Paz et al. "Closed-Loop Optogenetic Control of Thalamus as a New Tool to Interrupt Seizures After Cortical Injury", Nature Neurosci-ence, 16(1): 64-70, Published Online Nov. 7, 2012.
Rost et al. "Optogenetics at the Presynapse", Nature Neuroscience, 25(8): 984-998, Jul. 14, 2022.
Salanova et al. "The SANTÉ Study at 10 Years of Follow-Up: Effectiveness, Safety, and Sudden Unexpected Death in Epilepsy", Epilepsia, 62(6): 1306-1317, Published Online Apr. 8, 2021.
Paz et al. "Closed-Loop Optogenetic Control of Thalamus as a New Tool to Interrupt Seizures After Cortical Injury", Nature Neurosci-ence, 16(1): 64-70, Jan. 2013.
Communication Pursuant to Article 94(3) EPC Dated Aug. 8, 2024 From the European Patent Office Re. Application No. 20716958.2. (4 Pages).
International Search Report and the Written Opinion Dated Nov. 26, 2024 From the International Searching Authority Re. Application No. PCT/IL2024/050531. (13 Pages).
Clegern et al. "Simultaneous Electroencephalography, Real-Time Measurement of Lactate Concentration and Optogenetic Manipu-lation of Neuronal Activity in the Rodent Cerebral Cortex", Journal of Visualized Experiments, 19(70): e4328-1-e4328-6, Dec. 19, 2012.
International Search Report and the Written Opinion Dated Sep. 24, 2024 From the International Searching Authority Re. Application No. PCT/IL2024/050742. (14 Pages).
Communication Pursuant to Article 94(3) EPC Dated Oct. 16, 2025 From the European Patent Office Re. Application No. 20716958.2 (6 Pages).
International Preliminary Report on Patentability Dated Dec. 11, 2025 From the International Bureau of WIPO Re. Application No. PCT/IL2024/050531 (9 Pages).

* cited by examiner

FIG. 1A

```
PufTMT    MIVSNVS........LSGCAGVNGAVCAAEGHQAGGSDRSTLTPTGNLVVSVFLGFIGTFG
BovRhod   --MNGTEGPNFYVPFSNKTGVVRSPFEAPQYYLAEPWQFSM-------LAAYMFLLIMLG
vSWO      ...MSGED..DFYL.FQNISSV..GPWDGPQYHLAPVWAFRL........QAAFMGFVFFVG
cOPN5     --MSGMA----------SDCNSSSQFEEYLPHYVQQEDPFASKLSREADIIAGFYLTVIGILS
MosOPN3   --MYDAP---------NDVASS------VADYEDLMAPWAYNA-------AAITLFFIGFFG PufTMT    LVNNLLVLVLFCRYKMLRSPINLLLMNISISDLLVCVLGTPFSFAASTQGRWLIGEAGCV
BovRhod   FPINFLTLYVTVQHKKLRTPLNYILLNLAVADLFMVGGFTTTLYTSLHGYFVFGPTGCN
vSWO      TPLNAIVLVATILHYKKLBQPLNYILVNVSLGGFLFCIFSVFTVFIASCHGYFLFGRHVCA
cOPN5     TLGNGYVIFMSSKRKKKLRPALIMTVNLAVCDLGISVVGKPFSIISFFSHRWIFGWMGCR
MosOPN3   FFLNLFVIALMSKDMQLWTPMNIILFNLVCSDFSVSIIGNPLTLTSAISHRWIFGRTLCV PufTMT    WYGFANSLFGVVSLISLAVLSFERYSTMMTPTEADPSNYCKVCLGITLSWVYSLVWTVPP
BovRhod   LEGFFATLGGEIALWSLVVLAIERYVVVCKPMSNFRFGENHAIMGVAFTWVMALACAAPP
vSWO      LEAFLGSVAGLVTGWSLAFLAFERYYVICKPFGSIRFNSKHALMVVLATWIIGIGVSIPP
cOPN5     WYGWAGFFFGCGSLITMTAVSLDRYLRICHLAYGTWLKRHHAFICLALIWAYATFWATVP
MosOPN3   AYGFFMSLLGITSITTLTVLSYERYCLISRPFSSRNLSRKGAFLAIFFIWGYSFALTSPP PufTMT    LFGWSSYGPEGPGTTCSVNW--TAKTTNSISYIICLFVFCLIVPFLVIVFCYGKLLCAIR
BovRhod   LVGWSRYIPEGMQCSCGIDYYTPHEETNNESFVIYMFVVHFIIPLIVIFFCYGQLVFTVK
vSWO      FFGWSRFIPEGLQCSCGPDWYTVGTKYRSEYYTWFLFIFCFIIPLSLICFSYSQLLRTLR
cOPN5     FAGVGSYAPEPFGTSCTLDWWLAQASVAGQAFVLSILFFCLLFPTAVIVFSYVKIILKVK
MosOPN3   LFGWGAYVQEAANISCSVNW--ESQTKNATTYIIFLFVFGLVVPLIVIVYSYTNIIVYMR PufTMT    QVSGI-------NASTSRKREQRVLCMVVIMVICYLLCWLPYGVVALLATFGPPDLVTPEA
BovRhod   EAAAQQQ-----ESATTQKAEKEVTRMVIIMVIAFLICWLPYAGVAFYIFTHQGSDFGPIF
vSWO      AVAAQQQ----ESATTQKAEREVSHMVVVMVGSFCLCYVPYAALAMYMVNNRNHGLDLRL
cOPN5     SSTKEVAHYDTRIQNSHILEMKLTKVAMLICAGFLIAWIPYAVVSVWSAFGQPDSVPIQF
MosOPN3   RNSA--------RVGRINRAEQRVTSMVAVMIVAFMVAWTPYAIFALIEQFGPPELIGPGL PufTMT    SIIPSVLAKSSTVINPIIYVFMNKQFYRCFLALL
BovRhod   MTIPAFFAKTSAVYNPVIYIMMNKQFRNCMVTTL
vSWO      VTIPAFFSKSSCVYNPIIYCFMNKQFRACILEMV
cOPN5     SVVPTLLAKSAAMYNPIIYQVIDCKFA
MosOPN3   AVLFALIAKSSICYNPIIYVGMNTQFRAAFTRVRNKGGVPTADQNTTTMQRELTKSSRDN PufTMT    --------CCQ----------DPRSGSSMKSSSKVATKAKGVTPTGQRRTDLLYMVASLGRP
BovRhod   --------CCG----------------KNPLGDDEASTTVSKTETSQVAPA
vSWO      --------CRR----------------PMADESDVSGSQKTEVSTVSSSKVGP
cOPN5     --------CCR----------------SGGPKTLQKKSSLKESNMYTLSSHRDSA
MosOPN3   VECSFDFCRKKNRFKISLVKPTAPLAVVDVSSSSHPGKVTSRSPLDQTVLNEMNDELERGR PufTMT    AATIPQLGPSFDATNDFTKPPSSDTIKPVVVSLAAHCDG-
BovRhod   
vSWO      H
cOPN5     ALSGTQLEV
MosOPN3   ERSGAGYAGSRFVRPDFELSVINSGKSILIKSKNFRSNLL
```

PdCO2     LcPP     medakaTMT1A     zPP1     pPP2

BISTABLE TYPE II OPSINS AND USES THEREOF

RELATED APPLICATIONS

This application is a Continuation of PCT Patent Application No. PCT/IL2020/050330, having International filing date of Mar. 19, 2020 which claims the benefit of priority of Israel Patent Application No. 265486 filed on Mar. 19, 2019. The contents of the above applications are all incorporated by reference as if fully set forth herein in their entirety.

SEQUENCE LISTING STATEMENT

The ASCII file, entitled 89063SequenceListing.txt, created on Sep. 19, 2021, comprising 90,034 bytes, submitted concurrently with the filing of this application is incorporated herein by reference.

FIELD AND BACKGROUND OF THE INVENTION

The present invention, in some embodiments thereof, relates to bistable type II opsins and uses thereof.

Several neurological disorders and diseases associated with exocrine cells such as pancreatic and adrenal cells result from over excitation or secretion or loss of excitation or secretion.

For example, several neurological disorders, such as Parkinson's disease, dystonia, essential tremor and epilepsy are thought to result from altered patterns of neural activity in defined projection pathways in the brain. Similarly, psychiatric disorders such as depression, obsessive-compulsive disorder and addiction have been proposed to result from similar mechanisms, albeit in different brain circuits.

Deep-brain stimulation (DBS) has been shown to be effective for Parkinson's disease and several other movement disorders [e.g. Benabid A L et al. Lancet. 1991 Feb. 16; 337(8738):403-6; and Müller U J et al. Ann N Y Acad Sci. 2013 April; 1282:119-28]. However, the specificity of electrical DBS is limited by the non-specific effects of the stimulation currents on diverse neurons located at the site of stimulation.

In recent years, the development of cellular perturbation tools based on light sensitive proteins has resulted in a technology called optogenetics, referring to the integration of genetic and optical control to achieve gain- or loss-of-function of precisely defined events within specified cells of living tissues.

Thus, for example, optogenetics neuronal targeting combined with single-photon wide-field illumination has substantiated its enormous potential in neuroscience, enabling the optical control of entire neuronal networks and unravelling their role in the control of specific behaviors. However, while optogenetics allows robust and temporally-precise excitation of long-range projecting axons (Yizhar et al., 2011), silencing such long-range connections with existing optogenetics tools has proven more difficult (Wiegert et al., 2017). This is due to an inefficacy of most optogenetic tools to suppress synaptic transmission and to paradoxical effects of others (Mahn, et al., 2016). Suppression of axonal action potentials (APs) with potassium-conducting optogenetic tools has proven ineffective for presynaptic vesicle release inhibition (Cosentino, et al., 2015; Alberio, et al., 2018; Bernal Sierra, et al., 2018; Beck, et al., 2018). Chemogenetic tools such as hM4Di can be used for silencing presynaptic release (Stachniak, et al., 2014), but suffer from slow kinetics due to the unbinding and clearance of their small-molecule ligands. Some newly-developed optogenetic tools have also been used to selectively suppress exocytosis (Liu, et al., 2019), but these tools necessitate protein turnover to reinstate synaptic transmission and are consequently intrinsically slow.

Opsins are a major class of light-sensitive proteins that can be found across all kingdoms of life and serve a diverse range of functions. Opsins can be divided into two groups, while both types are seven-transmembrane-domain proteins belonging to the G protein-coupled receptor (GPCR) super-family, type I opsins (e.g. the microbial opsins) are ion channels or proton/ion pumps and thus are activated by light directly, while type II opsins activate G-proteins, which then activate effector enzymes that produce metabolites to e.g. open ion channels.

Current optogenetic approaches are mainly based on the light-activated microbial opsins such as channelrhodopsin, halorhodopsin, archaerhodopsin, and cruxhalorhodopsin.

Additional background art includes:

Isoldi, M. C., et al. (2005) Proceedings of the National Academy of Sciences of the United States of America 102, 1217-1221;

Koyanagi, M., et al. (2013) Proc Natl Acad Sci USA 110, 4998-5003;

Koyanagi, M., et al. (2017) Front. Ecol. Evol., 5, article 23;

Tsukamoto et al. J. Biol. Chem. (2017) doi: 10.1074/jbc.M117.793539;

Eickelbeck et al. ChemBioChem (2020) 21: 612-617;

Sakai K. et al. PLoS ONE (2015) 10(10): e0141238;

Kawano-Yamashita E. et al. PLoS ONE (2015) 10(10): e0141280;

US Patent Application Publication No. US20130347137; and

U.S. Pat. Nos. 9,505,817, 9,757,587, 8,716,447 and 9,175,095.

SUMMARY OF THE INVENTION

According to an aspect of some embodiments of the present invention there is provided a polypeptide comprising a bistable type II opsin and a heterologous ER export signal and/or membrane trafficking signal.

According to some embodiments of the invention, the bistable type II opsin is selected from the group consisting of OPN3, OPN4, OPN5, parapinopsin, PdCO, TMT and peropsin.

According to some embodiments of the invention, the bistable type II opsin is selected from the group consisting of OPN3, OPN4, OPN5, LcPP, DrPP2, TrPP2, PdCO and peropsin.

According to some embodiments of the invention, the bistable type II opsin is selected from the group consisting of OPN3, parapinopsin, PdCO and TMT.

According to some embodiments of the invention, the bistable type II opsin is OPN3.

According to some embodiments of the invention, the bistable type II opsin is selected form the group consisting of pufferfish teleost multiple tissue opsin (PufTMT) and mosquito OPN3 (MosOpn3).

According to some embodiments of the invention, the OPN3 is mosquito OPN3 (MosOpn3).

According to some embodiments of the invention, the parapinopsin is selected from the group consisting of Lethenteron camtschaticum parapinopsin (LcPP), zebra fish parapinopsin (zPP1) and pufferfish parapinopsin (pPP2).

According to some embodiments of the invention, the TMT is selected from the group consisting of pufferfish teleost multiple tissue opsin (PufTMT) and medaka teleost multiple tissue opsin 1A (medakaTMT1A).

According to some embodiments of the invention, the PdCO is PdCO2.

According to some embodiments of the invention, the ER export signal and/or the membrane trafficking signal is of a protein expressed in neuronal cells.

According to some embodiments of the invention, ER export signal and/or the membrane trafficking signal enables trafficking to axonal presynaptic terminals.

According to some embodiments of the invention, the ER export signal and/or the membrane trafficking signal is of a Kir2.1 polypeptide.

According to some embodiments of the invention, the ER export signal comprises SEQ ID NO: 2.

According to some embodiments of the invention, the membrane trafficking signal comprises SEQ ID NO: 1.

According to an aspect of some embodiments of the present invention there is provided a polynucleotide encoding the polypeptide.

According to some embodiments of the invention, a nucleic acid sequence encoding the bistable type II opsin is codon optimized to heterologous expression.

According to some embodiments of the invention, the codon optimized to heterologous expression is codon optimized to mammalian expression.

According to an aspect of some embodiments of the present invention there is provided a nucleic acid construct comprising the polynucleotide, and a regulatory element for directing expression of the polynucleotide in a cell.

According to an aspect of some embodiments of the present invention there is provided a cell expressing the polypeptide, the polynucleotide or the nucleic acid construct.

According to an aspect of some embodiments of the present invention there is provided a method of generating a G-protein signaling in a cell, the method comprising exposing the cell to light in a wavelength that activates the polypeptide.

According to some embodiments of the invention, the method is effected in-vitro or ex-vivo.

According to some embodiments of the invention, the method is effected in-vivo.

According to an aspect of some embodiments of the present invention there is provided a method of generating a G-protein signaling in a cell in a subject in need thereof, the method comprising:

(a) administering to the subject the polypeptide, the polynucleotide, the nucleic acid construct, or the cell; and (b) exposing a tissue region of the subject comprising the polypeptide, the polynucleotide, the nucleic acid construct or the cell to light in a wavelength that activates the polypeptide.

According to an aspect of some embodiments of the present invention there is provided a method of treating a disease that can be alleviated by this therapy in a subject in need thereof, the method comprising:

(a) administering to the subject a therapeutically effective amount of the polypeptide, the polynucleotide, the nucleic acid construct, or the cell; and (b) exposing a tissue region of the subject comprising the polypeptide, the polynucleotide, the nucleic acid construct or the cell to light in a wavelength that activates the polypeptide, thereby treating the disease in the subject.

According to an aspect of some embodiments of the present invention there is provided a composition comprising the polypeptide, the polynucleotide, the nucleic acid construct, or the cell, for use in treating a disease that can be alleviated by this therapy.

According to some embodiments of the invention, the cell is a mammalian cell.

According to some embodiments of the invention, the cell is a human cell.

According to some embodiments of the invention, the cell is selected from the group consisting of a neuron, an exocrine pancreatic cell and an exocrine adrenal cell, a myocardial cell, a salivary gland cell and a lacrimal cell.

According to some embodiments of the invention, the cell is a neuron.

According to some embodiments of the invention, the disease is associated with excitability of excitable tissues.

According to some embodiments of the invention, the disease is a neurological disease.

According to some embodiments of the invention, the neurological disease is selected from the group consisting of Parkinson, pain, epilepsy, depression, essential tremor, motor neuron disease, dystonia, obsessive compulsive disorder, addiction, schizophrenia, post-traumatic stress disorder, panic disorder and anxiety.

According to some embodiments of the invention, the neurological disease is selected from the group consisting of Parkinson, pain, epilepsy, depression, essential tremor, dystonia, obsessive compulsive disorder, addiction, schizophrenia, post-traumatic stress disorder, panic disorder and anxiety.

According to some embodiments of the invention, the disease is selected from the group consisting of stress, anxiety, hypertension, hyperaldosteronism, congenital adrenal hyperplasia and hyperinsulinemia.

According to some embodiments of the invention, the G-protein signaling is a Gi/o signaling.

According to some embodiments of the invention, the wavelength is 450-650 nm.

According to some embodiments of the invention, the wavelength is 350-650 nm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B show multiple sequence alignment of vertebrate visual and non-visual rhodopsins. FIG. 1A shows alignment of the sequences of the bovine rhodopsin (bRho), the mouse short-wavelength opsin (vSWO), the teleost multiple tissue opsin from pufferfish (PufTMT), the mosquito OPN3 opsin (MosOPN3) and the chicken OPN5 (cOPN5). FIG. 1B shows alignment of the sequences of the bovine rhodopsin (bRho), the mouse short-wavelength opsin (vSWO), the teleost multiple tissue opsin from pufferfish (PufTMT), the mosquito OPN3 opsin (MosOPN3), the chicken OPN5 (cOPN5), the *Platynereis dumerilii* ciliary opsin 2 (PdCO2), the medaka teleost multi-tissue opsin 1a (medakaTMT1a), the Lethenteron camtschaticum parapinopsin (LcPP), the zebrafish parapinopsin-1 (zPP1), and the pufferfish parapinopsin-2 (pPP2), Intracellular domains are labeled with a green background, extracellular domains are labeled with a blue background and the transmembrane domains are in gray.

Figure 2:
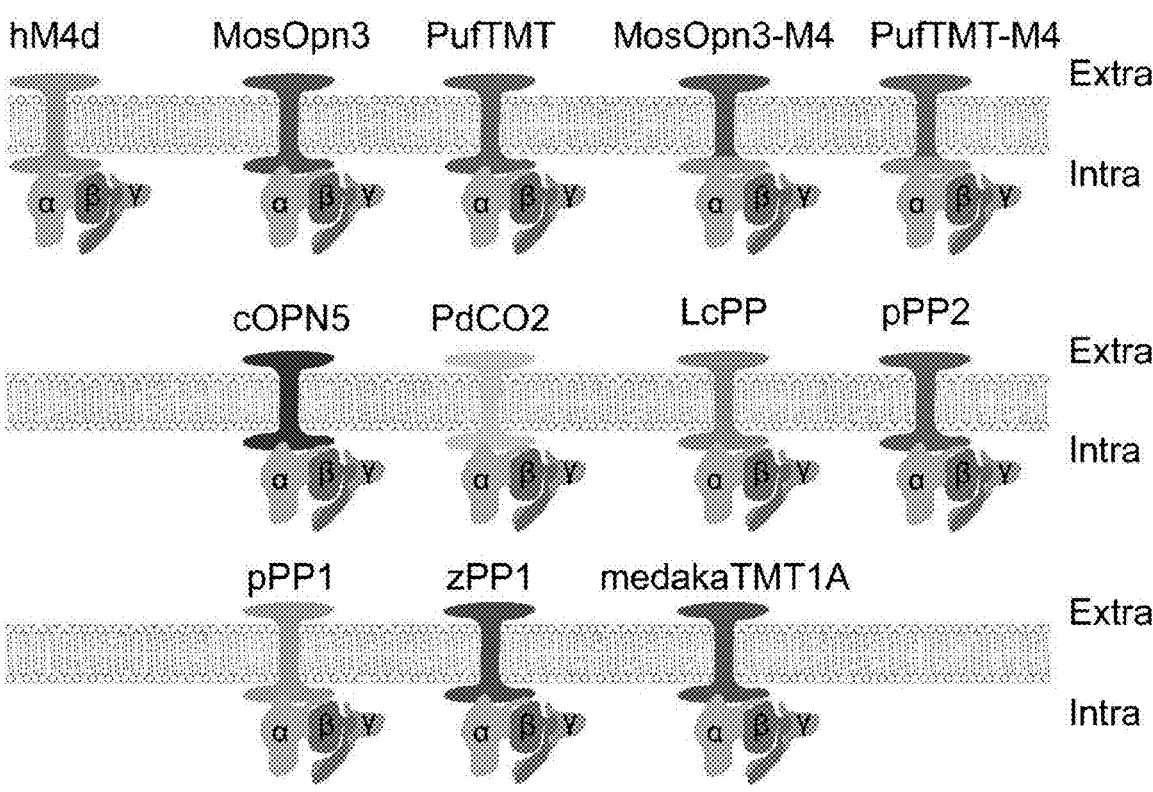

FIG. 2 is a schematic presentation of the rhodopsin proteins tested in this study. The engineered DREADD actuator hM4d, and several naturally occurring rhodopsins and engineered M4-rhodopsin chimeras, consisting of the extracellular and transmembrane domains of the rhodopsins shown on the left, each modified to contain the intracellular domains of the M4 muscarinic acetylcholine receptor (identical to the intracellular domain of hM4d).

Figures 3A, 3B, 3C:
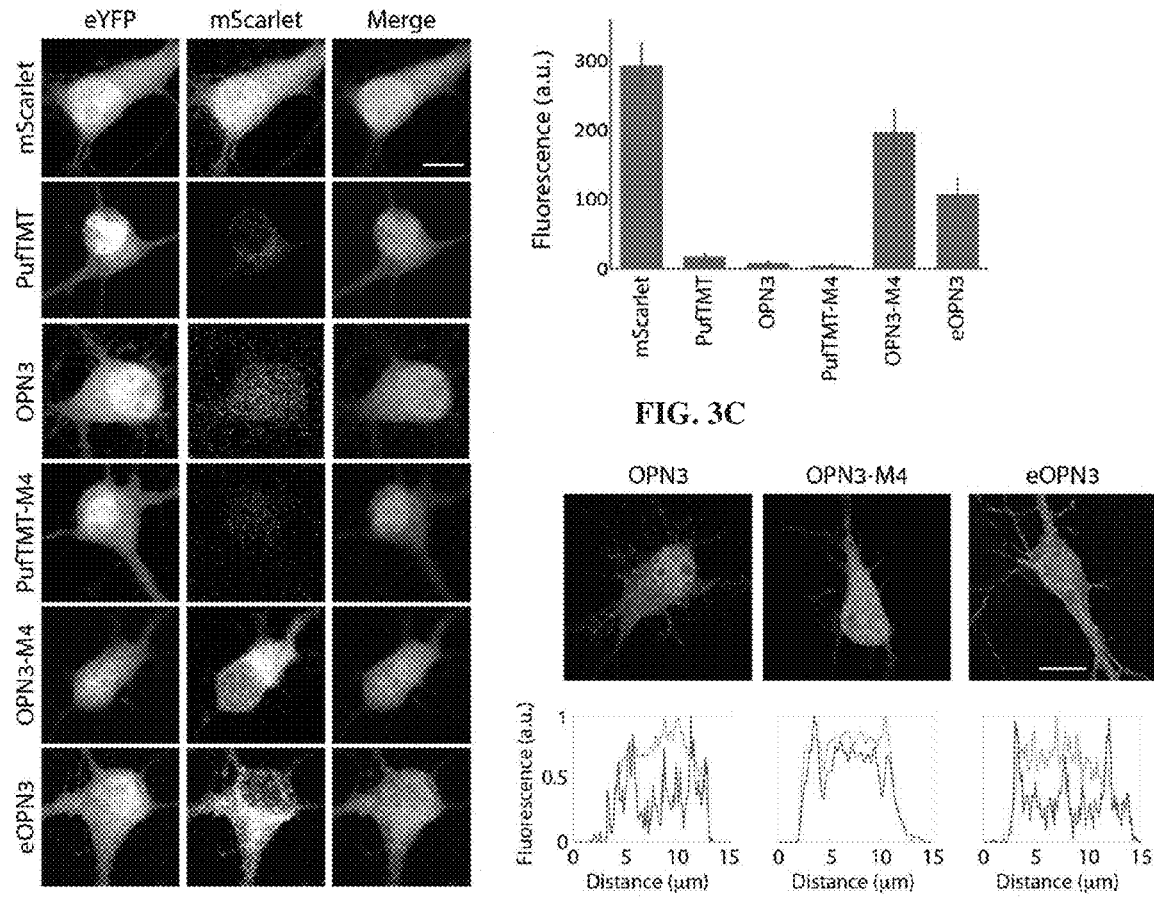

FIGS. 3A-C demonstrate exogenous expression of the indicated bistable type II opsins in cultured mammalian neurons. FIG. 3A shows representative confocal images of neurons co-transfected with expression vectors for EYFP and the indicated rhodopsin variants. Images show fluorescence in the EYFP channel (left), the mScarlet channel (center) and the merged images (right). Scale bar, 12 μm. FIG. 3B is a graph demonstrating expression level of each one of the rhodopsin-mScarlet constructs displayed in FIG. 3A, quantified as the average pixel intensity in n=13 neurons for each construct. FIG. 3C shows high-magnification maximum projection confocal images of cultured hippocampal neurons co-expressing OPN3 (left), OPN3-M4 (middle) or eOPN3 (right) and EYFP. Bottom plots depict representative line-scans through a single confocal slice from the same neurons, demonstrating the intracellular and membrane-localized fluorescence in these three constructs. Note that eOPN3 shows enhanced membrane localization compared with both OPN3 and OPN3-M4.

Figure 4A:
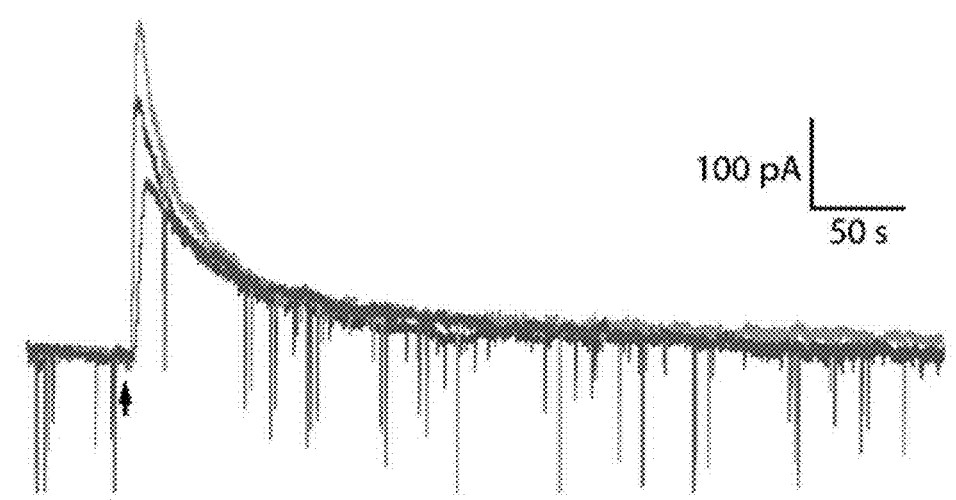
Figure 4A:
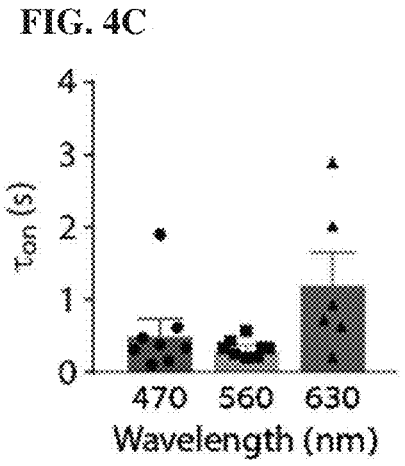

FIGS. 4A-C demonstrate light-triggered G protein-coupled inwardly-rectifying potassium channel (GIRK) currents in neurons co-expressing eOPN3 and GIRK2.1 as demonstration of the light gated activation of Gi/o signaling using bistable rhodopsins. FIG. 4A shows representative current recordings from a hippocampal neuron expressing eOPN3 and GIRK2.1, following illumination with a 500 ms pulse of blue, green or red light (470 nm, 560 nm and 630 nm, respectively, marked by a black arrow). FIG. 4B is a graph demonstrating the amplitude of GIRK-mediated currents evoked by light pulses at the indicated wavelengths, consistent with a green light absorption maximum of the dark-adapted state of this opsin. Individual recordings are shown as black markers, average and s.e.m. are indicated by the bar graph. FIG. 4C is a graph demonstrating time constant of GIRK current onset ($\tau_{on}$) calculated from GIRK currents evoked with light at the indicated wavelengths. Individual recordings are shown as black markers, average and s.e.m. are indicated by the bar graph.

Figures 5A, 5B:
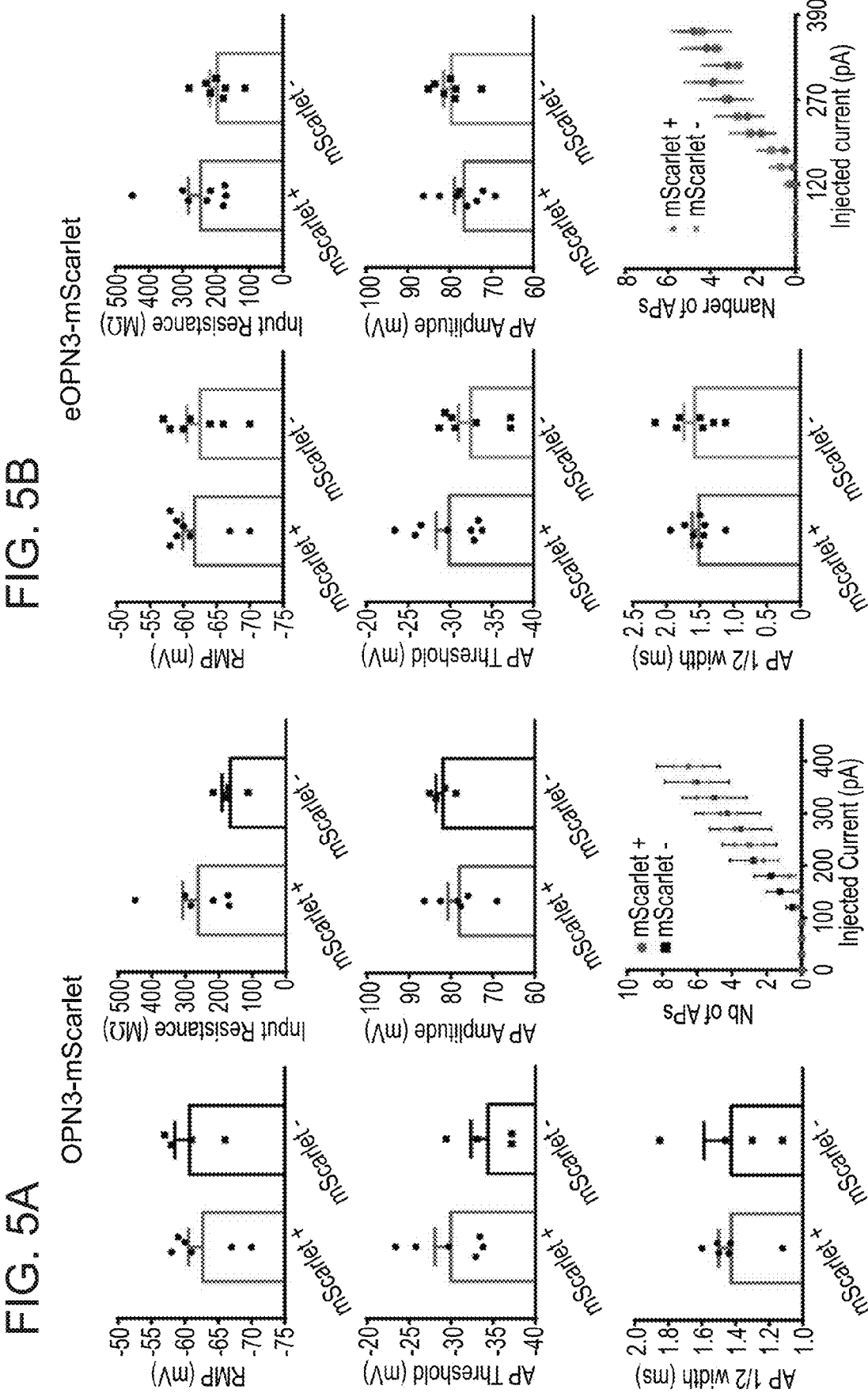

FIGS. 5A-B demonstrate no change in the intrinsic excitability of neurons expressing OPN3-mScarlet or eOPN3-mScarlet in the absence of light, indicative of construct expression without detrimental effects on cell health. FIG. 5A shows the intrinsic electrophysiological properties of cultured hippocampal neurons expressing OPN3-mScarlet (n=6) compared with those of neighboring untransfected neurons (n=4). FIG. 5B shows the intrinsic electrophysiological properties of cultured hippocampal neurons expressing eOPN3-mScarlet (n=8) compared with those of neighboring untransfected control neurons (n=7). These experiments demonstrate no significant change in the resting membrane potential, input resistance, action potential threshold, amplitude and half-width, and the number of action potentials evoked by increasing amounts of injected current.

Figures 6A, 6B:
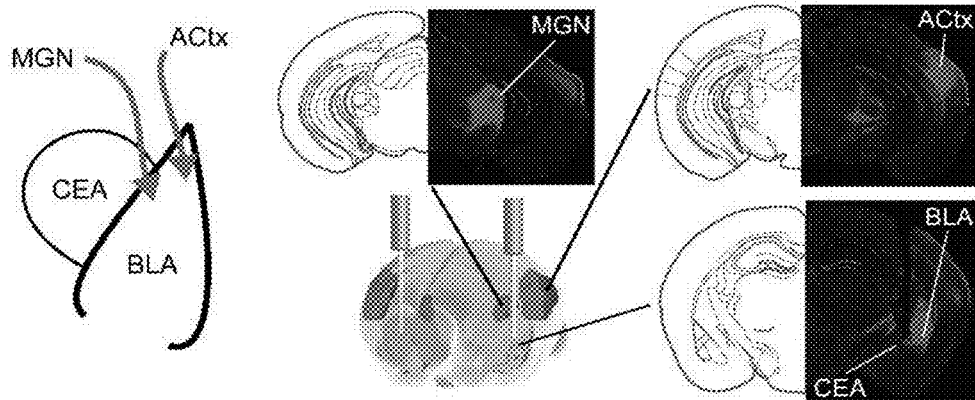
Figure 6C:
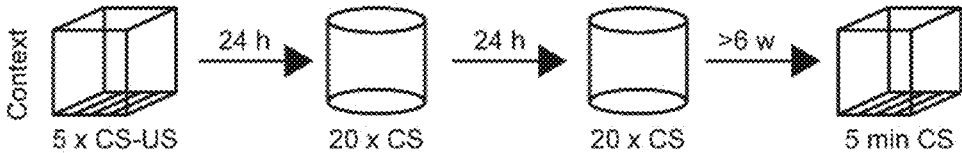
Figure 6D:
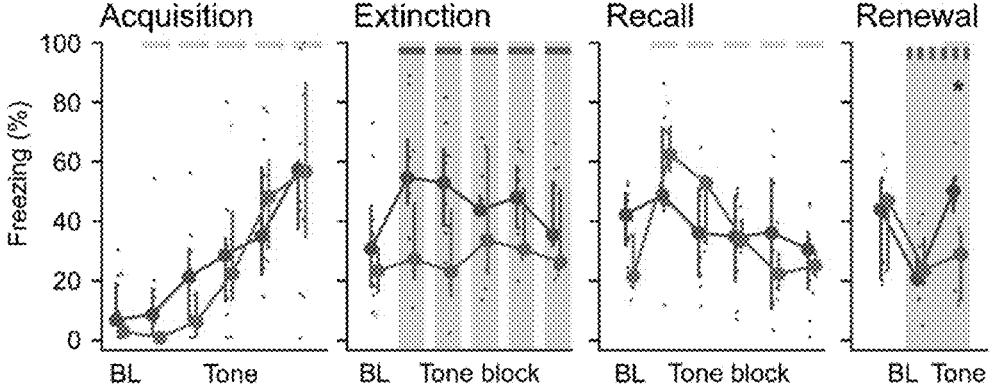
Figure 6E:
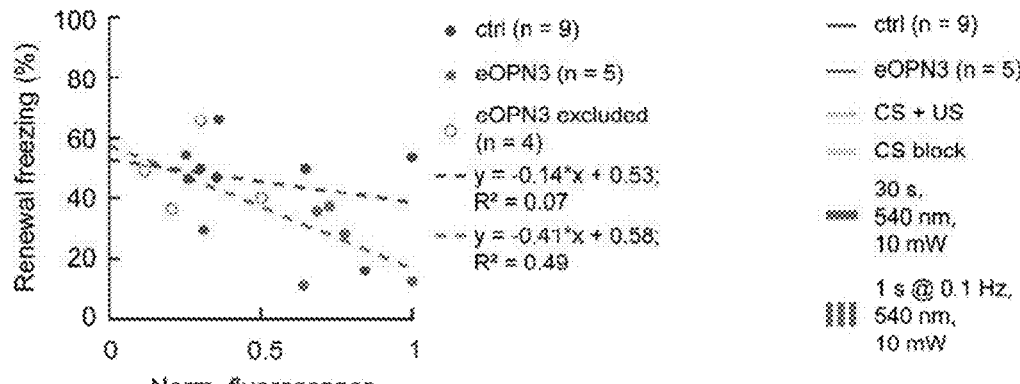

FIGS. 6A-E demonstrate in-vivo reduced tone-evoked freezing during fear renewal by eOPN3-mediated inhibition of MGN and ACtx terminals in the amygdala. FIG. 6A shows a schematic diagram of auditory inputs to the amygdala. Auditory cortex (ACtx) and medial *geniculate* nucleus (MGN) project to the basolateral amygdala (BLA). FIG. 6B shows a schematic representation of the experimental setup. Virus encoding eOPN3-mScarlet (eOPN3, n=9) or eYFP (ctrl, n=9) was injected bilaterally into the ACtx and MGN (red structures), while optic fibers were targeted bilaterally at the amygdala (cyan). Representative images of eOPN3 expression (red) in DAPI-stained (blue) brain sections. FIG. 6C shows a schematic representation of the auditory fear conditioning paradigm. FIG. 6D demonstrates freezing scoring during the behavioral paradigm shown in FIG. 6C. Tone evoked freezing was averaged in blocks of 4 consecutive tones during the extinction and recall sessions. eOPN3 mice showed a trend to reduced freezing during the extinction session (unpaired two-sample Wilcoxon test, p=0.08). During renewal, while the amount of freezing did not differ between the two groups in the pre-tone period (unpaired two-sample Wilcoxon test, p=0.43), tone evoked freezing was lower in eOPN3 expressing mice compared to control mice (unpaired two-sample Wilcoxon test, Bonferroni corrected p=$3.8 \cdot 10^{-2}$). The plot depicts the median and interquartile range, single trials are depicted as small points. FIG. 6E demonstrates that tone induced freezing during the renewal session was correlated with protein expression level in the case of eOPN3, but not in control mice (ctrl: $F_{(1,7)}$=0.54, p=0.48; eOPN3: $F_{(1,7)}$=6.77, p=$3.5 \cdot 10^{-2}$). eOPN3 mice showing an expression level of less than 60% of the maximal observed expression (open circles, n=4) were excluded from the analysis shown in FIG. 6D.

Figure 7A:
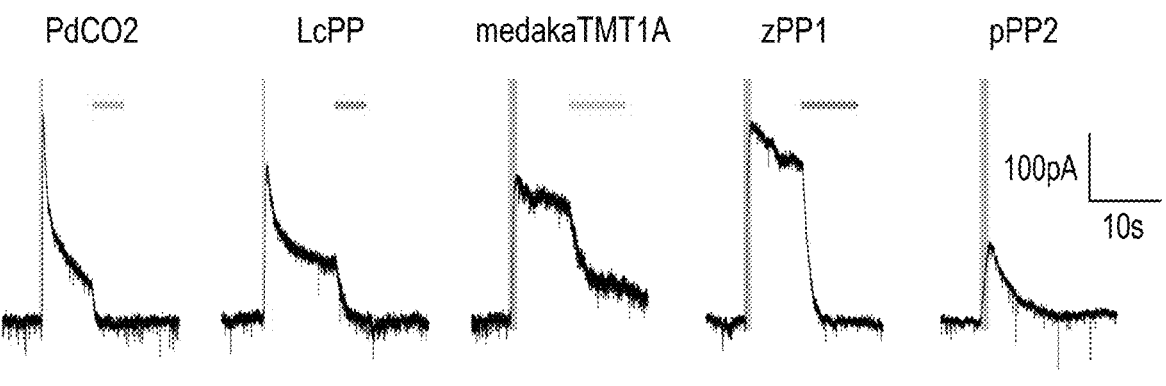

FIG. 7A demonstrates light-triggered bistable G protein-coupled inwardly-rectifying potassium channel (GIRK) currents in neurons expressing the following opsins: PdCO2, LcPP, medakaTMT1A, zPP1 or pPP2 in combination with co-expressed GIRK2.1.

Figure 7B:
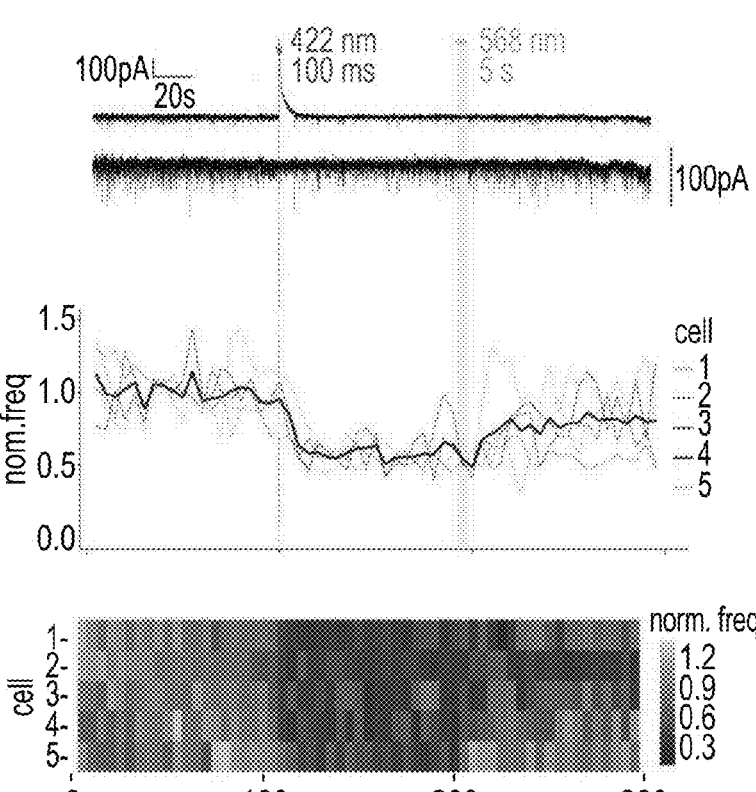

FIG. 7B demonstrates light triggered bistable inhibition of synaptic transmission in neurons transduced with PdCO2. Following 100s in the dark, 422 nm light was applied for 100 ms followed by light application of 568 nm for 5 s. Upper traces show light mediated GIRK currents activated upon illumination with 422 nm. In the lower trace, GIRK currents were subtracted, revealing reduction and recovery of mEPSC frequency upon 422 and 568 nm illumination, respectively. The middle figure in FIG. 7B demonstrates mEPSC frequency reduction and recovery for multiple cells (colored lines). Data shows 5 s binned mEPSC frequency normalized to the mean frequency during 100 s pre-illumination. Mean frequency of all cells is shown in black. Below the traces, the bottom figure displays normalized mEPSC frequency for each cell as shown in FIG. 7B as a heat map.

Figure 7C:
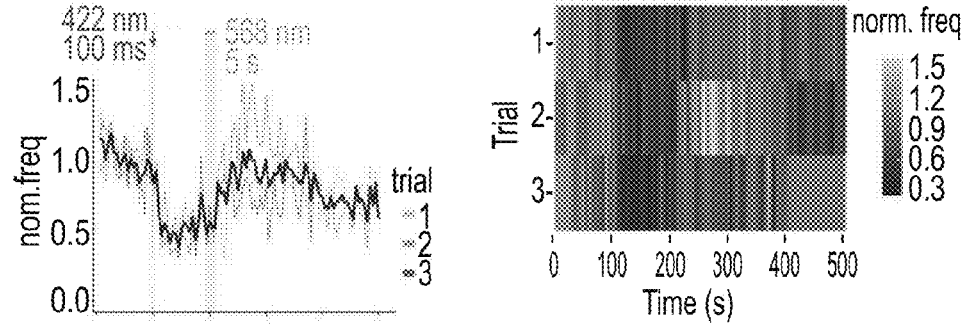

FIG. 7C (top) demonstrates repetitive PdCO2 activation and inactivation and resulting mEPSC frequency for three successive trials on a single neuron. Single trials are shown in color, while mean frequency of all trials is shown in black. FIG. 7C (bottom) displays normalized mEPSC frequency for each trial as a heat map. Data shows 5 s binned mEPSC frequency normalized to the mean frequency during 100 s pre-illumination for each trial.

DESCRIPTION OF SPECIFIC EMBODIMENTS OF THE INVENTION

The present invention, in some embodiments thereof, relates to bistable type II opsins and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Opsins are light-sensitive membrane proteins that can be found across all kingdoms of life.

Whilst reducing the present invention to practice, the present inventors have now uncovered that bistable type II opsins can be expressed on the cell surface of mammalian neurons and specifically in axonal presynaptic terminals by the addition of an ER export signal and/or membrane trafficking signal.

As is illustrated hereinunder and in the examples section, which follows, the present inventors show that the mosquito (*Anopheles stephensi*)-derived homolog of the human encephalopsin protein (OPN3) can be expressed on membranes of rat hippocampal neurons and most importantly in distal axonal presynaptic terminals by the addition of an ER export signal and membrane trafficking signal of a Kir2.1 protein (Examples 1-2, FIGS. 1A-3C). Following, the present inventors demonstrate that that the modified opsins activated the $G_{i/o}$ pathway in neurons in response to light, leading to suppression of presynaptic release (Example 2, FIGS. 4A-5B). Furthermore, the modified mosquito OPN3 mediated in-vivo suppression of auditory afferents to the amygdala in mice, leading to impaired recall of auditory-cued fear (Example 3, FIGS. 6A-E). Furthermore, the inventors show that additional modified bistable opsins (PdCO2, LcPP, medakaTMT1A, zPP1 and pPP2) can be expressed in neurons and activate G pathway signaling in response to light and thereby reduce synaptic events (Example 4, FIGS. 7A-C). Moreover, several opsins in this group can also be switched back to the inactive state upon illumination with red-shifted wavelengths, enabling bimodal control over the opsins by light.

Consequently, the specific embodiments of the present teachings suggest polypeptides comprising a bistable type II opsin and a heterologous ER export signal and/or membrane trafficking signal, polynucleotides encoding same and method of use thereof.

Thus, according to a first aspect of the present invention, there is provided a polypeptide comprising a bistable type II opsin and a heterologous ER export signal and/or membrane trafficking signal.

A Type II opsin is a G-coupled protein receptor (GPCR) which is made light-sensitive with an attached chromophore molecule that allows it to absorb light. Most type II opsins bind 11-cis retinal as a chromophore to form a photosensitive pigment (opsin-based pigment). The isomerization of the chromophore (e.g. 11-cis to all-trans) in an opsin-based pigment upon light absorption triggers G protein activation.

According to specific embodiments, the Type II opsin activates $G_i$-type and $G_o$-type G protein in a light dependent manner.

According to specific embodiments, the Type II opsin activates $G_z$-type G protein in a light dependent manner.

Type II opsins do not comprise an ion channel or a proton/ion pump.

As used herein, the phrase "bistable type II opsin" refers to a type II opsin which remains bound to the chromophore (e.g. retinal) following illumination (i.e. does not undergo bleaching).

Hence, a bistable type II opsin displays prolonged signal transduction following a single illumination pulse. Typically, the bistable type II opsin reverts to an original dark state through thermal relaxation after minutes in the dark or by illumination with light at a different wavelength. Methods of determining bistability of the opsin are well known in the art and include spectroscopic measurements.

According to specific embodiments, the bistable type II opsin is a naturally occurring bistable type II opsin. Such naturally occurring bistable type II opsins are known in the art and include, but are not limited to OPN3 (e.g. MosOpn3), OPN4, OPN5, parapinopsin (e.g. LcPP, zPP1, pPP2, zPP2/DrPP2, pPP2/TrPP2), PdCO (e.g. PdCO2), TMT (e.g. PufTMT, medakaTMT1A), peropsin.

According to specific embodiments, the bistable type II opsin is selected from the group consisting of OPN3, OPN4, OPN5, parapinopsin, zPP2, pPP2, PdCO, TMT and peropsin According to specific embodiments, the bistable type II opsin is selected from the group consisting of OPN3, OPN4, OPN5, parapinopsin, PdCO and peropsin.

According to specific embodiments, the bistable type II opsin is selected from the group consisting of OPN3, parapinopsin, PdCO and TMT.

According to specific embodiments, the bistable type II opsin is selected from the group consisting of OPN3, parapinopsin and PdCO.

According to specific embodiments, the bistable type II opsin activates $G_{i/o}$ signaling in a cell expressing same following exposure to light in a wavelength that activates it, as determined by e.g. GsX assay (Ballister, et al., 2018); or the ability to evoke G protein-coupled inwardly-rectifying potassium channel-mediated (GIRK) currents in neurons expressing a GIRK2-1 channel, as described in details in the Examples section which follows.

According to specific embodiments, the bistable type II opsin activates Gz signaling in a cell expressing same following exposure to light in a wavelength that activates it, as determined by e.g. GsX assay (Ballister, et al., 2018).

According to specific embodiments, the bistable type II opsin is OPN3.

As used herein, the term "OPN3" refers to the vertebrate Opsin-3, also known as encephalopsin or panopsin, and any homolog thereof.

According to specific embodiments, the OPN3 is the mosquito (*Anopheles stephensi*) OPN3 (MosOpn3), such as provided in the following Accession Number: BAN05625.

According to specific embodiments, the MosOpn3 amino acid sequence comprises SEQ ID NO: 8.

According to specific embodiments, the MosOpn3 amino acid sequence consists of SEQ ID NO: 8.

According to specific embodiments, the MosOpn3 amino acid sequence is the amino acid sequence described in Koyanagi et al. (Proc Natl Acad Sci USA. 2013 Mar. 26; 110(13): 4998-5003), the content of which are fully incorporated herein by reference.

According to other specific embodiments, the MosOpn3 amino acid sequence is not the amino acid sequence described in Koyanagi et al. (Proc Natl Acad Sci USA. 2013 Mar. 26; 110(13): 4998-5003).

According to specific embodiments, the MosOpn3 amino acid sequence comprises SEQ ID NO: 9.

According to specific embodiments, the MosOpn3 amino acid sequence consists of SEQ ID NO: 9.

According to specific embodiments, the MosOpn3 amino acid sequence does not consist of SEQ ID NO: 9.

The term "MosOpn3" also encompasses functional homologues (naturally occurring or synthetically/recombinantly produced), which exhibit the desired activity (i.e., bistable type II opsin). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID No: 8; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

Sequence identity or homology can be determined using any protein or nucleic acid sequence alignment algorithm such as Blast, ClustalW, and MUSCLE.

The homolog may also refer to an ortholog, a deletion, insertion, or substitution variant, including an amino acid substitution, as further described hereinbelow.

According to specific embodiments, the MosOpn3 may comprise conservative and non-conservative amino acid substitutions.

According to specific embodiments, the bistable type II opsin is TMT, also known as Teleost multiple tissue.

According to other specific embodiments, the bistable type II opsin is not TMT.

According to specific embodiments, the TMT is the pufferfish teleost multiple tissue opsin (PufTMT) such as provided in the following Accession Number: AAM90677.

According to other specific embodiments, the bistable opsin II is not the pufferfish teleost multiple tissue opsin (PufTMT).

According to specific embodiments, the PufTMT amino acid sequence comprises SEQ ID NO: 10.

According to specific embodiments, the PufTMT amino acid sequence consists of SEQ ID NO: 10.

According to specific embodiments, the TMT is TMT1A such as the medaka teleost multiple tissue opsin 1A (medakaTMT1A) such as provided in the following Accession Number: AGK24990.

According to specific embodiments, the medakaTMT1A amino acid sequence comprises SEQ ID NO: 33.

According to specific embodiments, the medakaTMT1A T amino acid sequence consists of SEQ ID NO: 33.

According to specific embodiments, the PufTMT or medakaTMT1A amino acid sequence is the amino acid sequence described in Sakai K. et al. [PLoS ONE (2015) 10(10): e0141238], the content of which are fully incorporated herein by reference.

The terms "PufTMT", "medakaTMT1A" also encompass functional homologues (naturally occurring or synthetically/recombinantly produced), which exhibit the desired activity (i.e., bistable type II opsin). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID No: 10, 33, respectively; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

According to specific embodiments, the TMT (e.g. PufTMT, medaka TMT1A) may comprise conservative and non-conservative amino acid substitutions.

According to specific embodiments, the bistable type II opsin is parapinopsin. Non-limiting examples of parapinopsins include Lethenteron camtschaticum parapinopsin (LcPP), zebrafish parapinopsin 1 (zPP1), zebrafish parapinopsin 2 [zPP2, also known as *Danio rerio* parapinopsin2 (drPP2)], pufferfish parapinopsin (pPP2, also known as TrPP2).

According to specific embodiments, the parapinopsin is the Lethenteron camtschaticum (Lamprey) parapinopsin (LcPP) such as provided in the following Accession Number: BAD13381.

According to specific embodiments, the LcPP amino acid sequence comprises SEQ ID NO: 29.

According to specific embodiments, the LcPP amino acid sequence consists of SEQ ID NO: 29.

According to specific embodiments, the LcPP amino acid sequence is the amino acid sequence described in Eickelbeck et al. [ChemBioChem (2020) 21: 612-617], the content of which are fully incorporated herein by reference.

According to specific embodiments, the parapinopsin is the zebra fish parapinopsin 1 (zPP1) such as provided in the following Accession Number: AB626966.

According to specific embodiments, the zPP1 amino acid sequence comprises SEQ ID NO: 37.

According to specific embodiments, the zPP1 amino acid sequence consists of SEQ ID NO: 37.

According to specific embodiments, the zPP1amino acid sequence is the amino acid sequence described in Kawano-Yamashita E. et al. [PLoS ONE (2015) 10(10): e0141280], the content of which are fully incorporated herein by reference.

According to specific embodiments, the parapinop sin is the pufferfish parapinopsin (pPP2) such as provided in the following Accession Number: AB626965.

According to specific embodiments, the pPP2 amino acid sequence comprises SEQ ID NO: 41.

According to specific embodiments, the pPP2 amino acid sequence consists of SEQ ID NO: 41.

The terms "LcPP", "zPP1", "pPP2" also encompass functional homologues (naturally occurring or synthetically/recombinantly produced), which exhibit the desired activity (i.e., bistable type II opsin). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID No: 29, 37, 41, respectively; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

According to specific embodiments, the parapinopsin (e.g. LcPP, zPP1, pPP2) may comprise conservative and non-conservative amino acid substitutions. According to specific embodiments, the bistable type II opsin is PdCO, also known as *Platynereis dumerilii* ciliary opsin.

According to specific embodiments, the PdCO is the PdCO2 such as provided in the following Accession Number: AY692353.

According to specific embodiments, the PdCO2 amino acid sequence comprises SEQ ID NO: 25.

According to specific embodiments, the PdCO2 amino acid sequence consists of SEQ ID NO: 25.

According to specific embodiments, the PdCO amino acid sequence is the amino acid sequence described in Tsukamoto et al. [J. Biol. Chem. (2017) doi: 10.1074/jbc.M117.793539], the content of which are fully incorporated herein by reference.

The term "PdCO2" also encompasses functional homologues (naturally occurring or synthetically/recombinantly produced), which exhibit the desired activity (i.e., bistable type II opsin). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID No: 25; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

According to specific embodiments, the PdCO2 may comprise conservative and non-conservative amino acid substitutions.

According to specific embodiments, the bistable type II opsin is selected from the group consisting of MosOpn3, LcPP, zPP1, pPP2, PdCO2, PufTMT and medakaTMT1A.

According to specific embodiments, the bistable type II opsin is selected from the group consisting of MosOpn3, LcPP, zPP1, pPP2, PdCO2 and medakaTMT1A.

The polypeptides disclosed herein comprises an ER export signal and/or a membrane trafficking signal heterologous to the bistable type II opsin.

As used herein, the term "heterologous" refers to a sequence which is not native to the bistable type II opsin at least in localization or is completely absent from the native sequence of the polypeptide. The heterologous moiety forms a chimeric or a fusion polypeptide.

According to specific embodiments, the heterologous ER export signal and/or membrane trafficking signal is located C-terminally to the bistable type II opsin.

According to specific embodiments, the heterologous ER export signal and/or membrane trafficking signal enables trafficking to axonal presynaptic terminals.

ER export signals are known in the art, and disclosed e.g. in Stockklausner et al., FEBS Lett.; 493 (2-3):129-133 March, 2001; Ma et al., Science Vol. 291. no. 5502:316-319, 2001); Paulhe et al., J. Biol. Chem., Vol. 279, Issue 53, 55545-55555, Dec. 31, 2004); Farhan et al., J. Cell Sci. 121:753-761, Feb. 19, 2008; the contents of each are incorporated herein by reference in their entirety.

According to specific embodiments, the ER export signal is of a protein expressed in neuronal cells.

According to specific embodiments, the ER export signal is of a protein expressed in the axons or the presynaptic terminals of neuronal cells.

Non-limiting examples ER export signals can be the signals of the inward rectifier potassium channel Kir2.1, NgCAM, VAMP2, Neurexin, Synapsin, Synaptophysin, Synaptotagmin, SynCAM, Piccolo or Basoon.

According to specific embodiments, the ER signal is of the inward rectifier potassium channel Kir2.1.

Non-limiting examples of ER export signals that can be used with specific embodiments of the invention include, FXYENE (SEQ ID NO: 11, where X is any amino acid), e.g. FCYENEV (SEQ ID NO: 2); VXXSL (SEQ ID NO: 12, where X is any amino acid), e.g. VKESL (SEQ ID NO: 13); VLGSL (SEQ ID NO: 14); NANSFCYENEVALTSK (SEQ ID NO: 15); C-terminal valine residue; and VMI.

According to specific embodiments, the ER export signal comprises SEQ ID NO: 2.

According to specific embodiments, the ER export signal consists of SEQ ID NO: 2.

According to specific embodiments, the ER export signal amino acid sequence is 5-25 amino acids in length, e.g. 5-10, 10-15, 15-20, 20-25 amino acids in length.

Membrane trafficking signals are known in the art, and include, but are not limited to membrane trafficking signals of a protein expressed on the membranes of neuronal cells.

According to specific embodiments, the membrane trafficking signal is of a protein expressed in neuronal cells.

According to specific embodiments, the membrane trafficking signal is of a protein expressed in the axons or the presynaptic terminals of neuronal cells.

Non-limiting examples of membrane trafficking signals can be the signals of the inward rectifier potassium channel Kir2.1, the hChR2, the neuronal nicotinic acetylcholine receptor, NgCAM, VAMP2, Neurexin, Synapsin, Synaptophysin, Synaptotagmin, SynCAM, Piccolo or Basoon.

According to specific embodiments, the trafficking signal is of a Kir2.1 polypeptide. Trafficking sequences that are suitable for use with specific embodiments include, but are not limited to KSRITSEGEYIPLDQIDINV (SEQ ID NO: 1), MDYGGALSAVGRELLFVTNPVVVNGS (SEQ ID NO: 16), MAGHSNSMALFSFSLLWLCSGVLGTEF (SEQ ID NO: 17), MGLRALMLWLLAAAGLVRESLQG (SEQ ID NO: 18), MRGTPLLLVVSLFSLLQD (SEQ ID NO: 19).

According to specific embodiments, the membrane trafficking signal comprises SEQ ID NO: 1.

According to specific embodiments, the membrane trafficking signal consisting of SEQ ID NO: 1.

According to specific embodiments, the membrane trafficking signal amino acid sequence is 10-50 amino acids in length, e.g. 10-20, 20-30, 30-40, 40-50 amino acids in length.

Any of the components comprised in the polypeptide as described herein may be linked to each other directly of via a linker, each possibility represents a separate embodiment of the present invention.

Any linker known in the art can be used with specific embodiments of the invention.

According to specific embodiments, the linker may be derived from naturally-occurring multi-domain proteins or is an empirical linker as described, for example, in Chichili et al., (2013), Protein Sci. 22(2): 153-167, Chen et al, (2013), Adv Drug Deliv Rev. 65(10): 1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et al., (2000), Protein Eng. 13(5):309-312, the entire contents of which are hereby incorporated by reference.

According to specific embodiments, the linker is a synthetic linker such as PEG.

According to specific embodiments, the linker is a polypeptide.

According to specific embodiments, the linker is selected from the group consisting of PRARDP (SEQ ID NO: 4), $(Gly)_n$ (where n indicates variable copy numbers), $(G_nS_n)_n$ (where n indicates variable copy numbers), $((G_nS_n)_nP_n)_n$ (where n indicates variable copy numbers) and $(EAAAK)_n$ (where n indicates variable copy numbers, SEQ ID NO: 24).

The term "polypeptide" or "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

According to specific embodiments, the polypeptide may comprise epitope tags, fluorescent proteins, peptides that provide for ease of purification; cleavable linker peptides; a cell penetrating moiety, targeting moieties and the like.

According to specific embodiments, the polypeptide comprises an amino acid sequence for directing the polypeptide to a specific membrane location e.g. the axon or the presynaptic terminal.

According to specific embodiments, the polypeptide comprises a targeting moiety for directing the polypeptide to a specific cell type e.g. neuron.

According to specific embodiments, the polypeptide comprises a cell penetrating moiety, as further described hereinbelow.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (~CH2-NH—), sulfide bonds (~CH2-S—), ethylene bonds (~CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of some embodiments of the invention are utilized in a linear form, although it will be appreciated that in cases where cyclicization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

According to specific embodiments, the peptide is provided in a formulation suitable for cell penetration that enhances intracellular delivery of the polypeptide.

For example, the polypeptide may be incorporated into a particulated delivery vehicle, e.g., a liposome, or a nano- or microparticle, by any of the methods known in the art [e.g. Liposome Technology, Vol. II, Incorporation of Drugs, Proteins, and Genetic Material, CRC Press; Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43].

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. Liposomes can be of different sizes, may contain a low or a high pH and may be of different charge.

According to specific embodiments, cell penetrating peptides (CPP) are used to transport the polypeptide to the interior of the cells. Cell-Penetrating Peptides (CPPs) are short peptides (≤40 amino acids), with the ability to gain access to the interior of almost any cell. They are highly cationic and usually rich in arginine and lysine amino acids. They have the exceptional property of carrying into the cells a wide variety of covalently and noncovalently conjugated cargoes such as proteins, oligonucleotides, and even 200 nm liposomes. TAT (transcription activator from HIV-1), pAntp (also named penetratin, *Drosophila* antennapedia homeodomain transcription factor) and VP22 (from Herpes Simplex virus) are examples of CPPs that can enter cells in a non-toxic and efficient manner and may be suitable for use with some embodiments of the invention. Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research. (2007) 100: 1626-1633].

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50. According to specific embodiments, the peptide is produced by recombinant DNA technology. A "recombinant" peptide, or protein refers to a peptide, or protein produced by recombinant DNA techniques; i.e., produced from cells transformed by an exogenous DNA construct encoding the desired peptide or protein.

Thus, according to another aspect of the present invention, there is provided a polynucleotide comprising a nucleic acid sequence encoding any of the above described polypeptides.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

According to specific embodiments, any of the polynucleotides and nucleic acid sequences disclosed herein may comprise conservative nucleic acid substitutions. Conservatively modified polynucleotides refer to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified polynucleotides. According to specific embodiments, any polynucleotide and nucleic acid sequence described herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a polynucleotide which encodes a polypeptide is implicit in a described sequence with respect to the expression product.

According to specific embodiments, the nucleic acid sequences disclosed herein are codon optimized to heterologous (e.g. mammalian) expression.

Methods of codon optimization are known in the art and disclosed e.g. in Grote et al. (Nucleic Acid Res. Nucleic Acids Res. (2005) July 1; 33 (Web Server issue): W526-W531) and include e.g. mouse codon usage optimized or human codon usage optimized versions.

Hence, according to specific embodiments, the nucleic acid sequence of the MosOpn3 comprises SEQ ID NO: 20.

According to specific embodiments, the nucleic acid sequence of the MosOpn3 consists of SEQ ID NO: 20.

According to specific embodiments, the nucleic acid sequence of the MosOpn3 comprises SEQ ID NO: 21.

According to specific embodiments, the nucleic acid sequence of the MosOpn3 consists of SEQ ID NO: 21.

According to specific embodiments, the nucleic acid sequence of the PufTMT comprises SEQ ID NO: 22.

According to specific embodiments, the nucleic acid sequence of the PufTMT consists of SEQ ID NO: 22.

According to specific embodiments, the nucleic acid sequence of the PufTMT comprises SEQ ID NO: 23.

According to specific embodiments, the nucleic acid sequence of the PufTMT consists of SEQ ID NO: 23.

According to specific embodiments, the nucleic acid sequence of the medakaTMT1A comprises SEQ ID NO: 34.

According to specific embodiments, the nucleic acid sequence of the medakaTMT1A consists of SEQ ID NO: 34.

According to specific embodiments, the nucleic acid sequence of the LcPP comprises SEQ ID NO: 30.

According to specific embodiments, the nucleic acid sequence of the LcPP consists of SEQ ID NO: 30.

According to specific embodiments, the nucleic acid sequence of the zPP1 comprises SEQ ID NO: 38.

According to specific embodiments, the nucleic acid sequence of the zPP1 consists of SEQ ID NO: 38.

According to specific embodiments, the nucleic acid sequence of the pPP2 comprises SEQ ID NO: 42.

According to specific embodiments, the nucleic acid sequence of the pPP2 consists of SEQ ID NO: 42.

According to specific embodiments, the nucleic acid sequence of the PdCO2 comprises SEQ ID NO: 26.

According to specific embodiments, the nucleic acid sequence of the PdCO2 consists of SEQ ID NO: 26.

To express an exogenous polypeptide in mammalian cells, a polynucleotide sequence encoding the polypeptide is preferably ligated into a nucleic acid construct suitable for mammalian cell expression. Such a nucleic acid construct includes a promoter sequence for directing transcription of the polynucleotide sequence in the cell in a constitutive or inducible manner.

Hence, according to specific embodiments, there is provided nucleic acid construct comprising the polynucleotide and a regulatory element for directing expression of said polynucleotide in a cell.

According to specific embodiments, the regulatory element is a heterologous regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], pancreas-specific promoters [Edlunch et al. (1985) Science 230:912-916] or mammary gland-specific promoters such as the milk whey promoter (U.S. Pat. No. 4,873,316 and European Application Publication No. 264,166).

According to specific embodiments, promoter is a neuron specific promoter. Non-limiting examples of neuron-specific promoters include the neurofilament promoter [Byrne et al. (1989) Proc. Natl. Acad. Sci. USA 86:5473-5477; or GenBank HUMNFL, L04147], neuron-specific enolase (NSE) promoter (see, e.g., EMBL HSENO2, X51956; see also, e.g., U.S. Pat. Nos. 6,649,811, 5,387,742); aromatic amino acid decarboxylase (AADC) promoter; synapsin promoter (see, e.g., GenBank HUMSYNIB, M55301); thy-1 promoter (see, e.g., Chen et al. (1987) Cell 51:7-19; and Llewellyn et al. (2010) Nat. Med. 16:1161); serotonin receptor promoter (see, e.g., GenBank S62283); tyrosine hydroxylase promoter (TH) (see, e.g., Nucl. Acids. Res. 15:2363-2384 (1987) and Neuron 6:583-594 (1991)); GnRH promoter (see, e.g., Radovick et al., Proc. Natl. Acad. Sci. USA 88:3402-3406 (1991)); L7 promoter (see, e.g., Oberdick et al., Science 248:223-226 (1990)); DNMT promoter (see, e.g., Bartge et al., Proc. Natl. Acad. Sci. USA 85:3648-3652 (1988)); enkephalin promoter (see, e.g., Comb et al., EMBO J. 17:3793-3805 (1988)); a myelin basic protein (MBP) promoter; CMV enhancer/platelet-derived growth factor-$\beta$ promoter (see, e.g., Liu et al. (2004) Gene Therapy 11:52-60); motor neuron-specific gene Hb9 promoter (see, e.g., U.S. Pat. No. 7,632,679; and Lee et al. (2004) Development 131:3295-3306); and alpha subunit of Ca($^{2+}$)-calmodulin-dependent protein kinase II (CaMKIIα) promoter (see, e.g., Mayford et al. (1996) Proc. Natl. Acad. Sci. USA 93:13250).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long terminal repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference. Enhancers specific for distinct neuronal cell types that can be included in AAV expression vectors to gain specificity without a Cre-driver line have also been described in the arts and described e.g. in Hrvatin et al. (doi: www://doi(dot)org/10.1101/570895), which is incorporated herein by reference. Cell-type specific enhancers, such as described in e.g. Milner e al. [Nature Neuroscience volume 22, pages 1345-1356 (2019)] or Dimidschstein et al. (Nature Neuroscience volume 19, pages 1743-1749 (2016)], the contents of which are incorporated herein by reference, for expression in inhibitory interneurons.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

Recombinant viral vectors are useful for in vivo expression of the polypeptides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the polypeptide of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the polypeptide and the heterologous protein, the polypeptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

The present invention also contemplates cells comprising the composition described herein.

Thus, according to an aspect of the present invention, there is provided a cell expressing the polypeptide, the polynucleotide encoding same or the nucleic acid construct encoding same.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

According to specific embodiments, the cell is a human cell.

Suitable mammalian cells include primary cells and immortalized cell lines.

According to specific embodiment, the mammalian cell is a neuron, e.g., a non-immortalized (primary) neuron.

According to other specific embodiments, the mammalian cell is an immortalized cell line.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

According to specific embodiments, the cell is a cell of an excitable tissue, e.g. a neuron, an exocrine pancreatic cell, an exocrine adrenal cell, a myocardial cell, a salivary gland cell, a lacrimal cell.

According to specific embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S(ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

According to specific embodiments, the cell is not a visual cell.

According to specific embodiments, the cell is not a retinal cell.

According to specific embodiments, the cell does not express a G protein transducin (Gt).

According to specific embodiments, the cell expresses a Gi/o protein.

According to specific embodiments, recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The present invention also contemplates uses of the polypeptides, polynucleotides, nucleic acid constructs and cells disclosed herein in e.g. therapeutic, research and diagnostic applications.

Thus, according to an aspect of the present invention, there is provided a method of generating a G-protein signaling in a cell, the method comprising exposing a cell expressing the polypeptide, the nucleic acid or the nucleic acid construct disclosed herein to light in a wavelength that activates the polypeptide.

According to an additional or an alternative aspect of the present invention there is provided a method of determining the effect of generating a G-protein signaling in a cell, the method comprising:

(a) exposing a cell expressing the polypeptide, the nucleic acid or the nucleic acid construct disclosed herein to light in a wavelength that activates the polypeptide; and (b) determining a biological outcome following the exposing.

The method of some embodiments of the invention can be effected in-vitro, ex-vivo or in-vivo.

According to specific embodiments, the method is effected in-vitro or ex-vivo.

According to specific embodiments, the method is effected in-vivo.

According to an additional or an alternative aspect of the present invention, there is provided a method of generating a G-protein signaling in a cell in a subject in need thereof, the method comprising:

(a) administering to the subject the polypeptide, the polynucleotide, the nucleic acid construct or the cell; and (b) exposing a tissue region of said subject comprising said polypeptide, said polynucleotide, said nucleic acid construct or said cell to light in a wavelength that activates said polypeptide.

According to specific embodiments, following administering the polypeptide, the polynucleotide or the nucleic acid construct is expressed in a cell(s) of the subject.

According to specific embodiments, the G-protein signaling is a Gi/o signaling (e.g. inhibits the production of cAMP from ATP through the $G\alpha$ subunit and/or inhibits activity of calcium channels and/or SNARE proteins through the $G\beta\gamma$ subunit in e.g. neuron).

According to specific embodiments, the G-protein signaling is a Gz signaling.

According to specific embodiments, when the cell is a neuronal cell, the G-protein signaling is generated in axonal presynaptic terminals. Methods of determining changes effected in axonal presynaptic terminals such as presynaptic vesicle release are known in the art and described for example in Wiegert et al. Proc Natl Acad Sci USA. 2013 Nov. 19; 110(47):E4510-9; and Rost et al. Nat Neurosci. 2015 December; 18(12):1845-1852, the contents of which are fully incorporated herein by reference.

According to specific embodiments, it is possible to reverse activation of the expressed polypeptide using light in a wavelength different than the one that activates the polypeptide, enabling easier regulation of the amount and duration of activation. Thus, according to specific embodiments, the method comprising exposing the cell expressing the polypeptide, the nucleic acid or the nucleic acid construct disclosed, or a tissue region comprising the polypeptide, the nucleic acid, the nucleic acid construct or the cell disclosed herein, to light in a wavelength that inhibits activation of the polypeptide.

According to an additional or an alternative aspect of the present invention, there is provided a method of treating a disease that can be alleviated by this therapy in a subject in need thereof, the method comprising:

(a) administering to the subject a therapeutically effective amount of the polypeptide, the polynucleotide, the nucleic acid construct, or the cell; and (b) exposing a tissue region of said subject comprising said polypeptide, said polynucleotide, said nucleic acid construct or said cell to light in a wavelength that activates said polypeptide, thereby treating the disease in the subject.

According to an additional or an alternative aspect of the present invention, there is provided a composition comprising the polypeptide, the polynucleotide, the nucleic acid construct, or the cell, for use in treating a disease that can be alleviated by this therapy.

The term "treating" or "treatment" refers to inhibiting, preventing or arresting the development of a pathology (disease, disorder or medical condition) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, e.g., human beings at any age and of any gender. According to specific embodiments, the term "subject" refers to a subject who suffers from the pathology (disease, disorder or medical condition). According to specific embodiments, this term encompasses individuals who are at risk to develop the pathology.

As used herein, the term "disease is associated with excitability of excitable tissues" refers to a disease or disorder that can be ameliorated by activating a G-protein signaling in excitable cells.

According to specific embodiments, the disease can benefit from activating a Gi/o signaling in excitable cells.

According to specific embodiments, the disease can benefit from activating a Gz signaling in excitable cells.

Such excitable cell and tissues include neurons, myocardial cells, glandular tissues, salivary glands and lacrimal glands.

Thus, according to specific embodiments, the disease is a neurological disease.

As used herein, the term "neurological disease" refers to a disease that can benefit from activating G-protein signaling in neuronal cells (and specifically in axonal presynaptic terminals) or in synaptic projection pathways.

According to specific embodiments, the neurological disease can benefit from suppressing presynaptic transmission of neurons.

Non-limiting examples of such neurological diseases include, Parkinson, pain (e.g. chronic pain), epilepsy, depression, essential tremor, motor neuron disease, dystonia, obsessive compulsive disorder, addiction, schizophrenia, post-traumatic stress disorder, panic disorder, anxiety disorders.

According to specific embodiments, the disease is a motor neuron disease. Non-limiting examples of motor neuron diseases include monomelic amyotrophy (MMA), progressive muscular atrophy (PMA), sporadic amyotrophic lateral sclerosis (ALS), pseudobulbar palsy primary lateral sclerosis (PLS), progressive bulbary palsy (PBP).

As secretion of glandular factors, such as hormones is in some cases effected by the excitation of secreting cells or tissues, according to other specific embodiments, the disease is associated with cells of glandular tissues such as pancreatic exocrine cells and adrenal exocrine cells.

A non-limiting example of such diseases associated with pancreatic exocrine cells is hyperinsulinemia.

Non-limiting examples of such diseases associated with adrenal exocrine cells include stress, anxiety, hypertension, hyperaldosteronism, congenital adrenal hyperplasia.

Myocardial contraction depends on the opening and closing of a complex series of ion channels in myocardial cell membranes, the end result of this depolarization-repolarization is that the contractile filaments in the cell engage, and the cell contracts.

Hence, according to specific embodiments, the disease is associated with myocardial cells such as, but not limited to cardiac arrhythmia.

According to specific embodiments, the disease is associated with lacrimal and/or salivary secreting cells such as, but not limited to Sjorgen's syndrome.

The polypeptide, polynucleotides, nucleic acid constructs and cell of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the polypeptide, polynucleotides, nucleic acid constructs and cells accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The methods of some embodiments of the present invention comprise exposing a cell or a tissue region to a light in a wavelength that activates the polypeptide.

Such a wavelength typically depends on the type of the bistable type II opsin. Determining the suitable wavelength is well within the capabilities of the skilled in the art. According to specific embodiments, the light is an ultraviolet, blue, green or red light.

According to specific embodiments, the wavelength is 350-650 nm.

According to specific embodiments, the wavelength is 450-650 nm.

According to specific embodiments, the wavelength is 450-490 nm.

According to specific embodiments, the wavelength is about 470 nm.

According to specific embodiments, the wavelength is 540-580 nm.

According to specific embodiments, the wavelength is about 560 nm.

According to specific embodiments, the wavelength is 610-650 nm.

According to specific embodiments, the wavelength is about 630 nm.

According to specific embodiments, exposing the cell or the tissue region to light is effected by light pulses that can have a duration for any of at least 1 millisecond (ms), at least 5 ms, at least 10 ms, at least 50 ms, at least 100 ms, at least 500 ms, at least 1 sec.

According to specific embodiments, exposing the cell or the tissue region to light is effected by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 sec, about 1.25 sec, about 1.5 sec, or about 2 sec.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Animals—Animal experiments were carried out according to the guidelines stated in directive 2010/63/EU of the European Parliament on the protection of animals used for scientific purposes. Animal experiments at the Weizmann Institute were approved by the Weizmann Institute Institutional Animal Care and Use Committee (IACUC).

Molecular cloning of bistable rhodopsin constructs—The genes encoding mScarlet, and the following opsins: OPN3, PufTMT, OPN3-M4, PufTMT-M4, PdCO2, LcPP, medakaTMT1A, zPP1 and pPP2 were synthesized using the Twist gene synthesis service (Twist Bioscience, USA). All genes were subcloned into pAAV vectors under the CamKIIα promoter and in-frame with mScarlet at the C-terminus. The enhanced expression plasmids (eOPN3, PdCO2, LcPP, medakaTMT1A, zPP1 and pPP2) were generated by adding the Kir2.1 membrane trafficking signal (KSRIT-SEGEYIPLDQIDINV, SEQ ID NO: 1) between the opsin and the mScarlet coding sequences and the Kir2.1 ER export signal (FCYENEV, SEQ ID NO: 2) following the C-terminus of mScarlet. The sequences of the eOPN3-mScarlet, PdCO2-mScarlet, LcPP-mScarlet, medakaTMT1A-mScarlet, zPP1-mScarlet and pPP2-mScarlet open reading frames are provided in SEQ ID NOs: 5-6, 27-28, 31-32, 35-36, 39-40 and 43-44 (the mScarlet nucleic acid sequence is provided in SEQ ID NO: 7).

Production of recombinant AAV vectors—HEK293 cells were seeded at 25-35% confluence. The cells were transfected 24 hours later with plasmids encoding AAV rep, cap of AAV1 and AAV2 and a vector plasmid for the rAAV cassette expressing the relevant DNA using the PEI method [Grimm, D., Kay, M. A. & Kleinschmidt, J. A. *Mol. Ther.:*

*J. Am. Soc. Gene Ther.* 839-850 (2003)]. Cells and medium were harvested 72 hours following transfection, pelleted by centrifugation (300 g), resuspended in lysis solution ([mM]: 150 NaCl, 50 Tris-HCl; pH 8.5 with NaOH) and lysed by three freeze-thaw cycles. The crude lysate was treated with 250 U benzonase (Sigma) per 1 ml of lysate at 37° C. for 1.5 hours to degrade genomic and unpackaged AAV DNA before centrifugation at 3,000 g for 15 minutes to pellet cell debris. The virus particles in the supernatant (crude virus) were purified using heparin-agarose columns, eluted with soluble heparin, washed with phosphate buffered saline (PBS) and concentrated by Amicon columns. Viral suspension was aliquoted and stored at –80° C. Viral titers were measured using real-time PCR. In experiments that compared between different constructs, viral titers were matched by dilution to the lowest concentration. AAV vectors used for neuronal culture transduction were added 4 days following cell seeding. Recordings were carried out between 4-10 days following viral transduction. The following viral vectors were used in this study: AAV2/1&2.CamKIIα.OPN3-mScarlet, AAV2/1&2.CamKIIα.eOPN3-mScarlet, AAV2/1&2.CamKIIα.mCherry.WPRE.

Primary hippocampal neuron culture—Primary cultured hippocampal neurons were prepared from male and female P0 Sprague-Dawley rat pups (Envigo). CA1 and CA3 were isolated, digested with 0.4 mg ml$^{-1}$ papain (Worthington), and plated onto glass coverslips pre-coated with 1:30 Matrigel (Corning). Cultured neurons were maintained in a 5% $CO_2$ humidified incubator with Neurobasal-A medium (Invitrogen) containing 1.25% fetal bovine serum (FBS, Biological Industries), 4% B-27 supplement (Gibco), 2 mM Glutamax (Gibco) and plated on coverslips in a 24-wells plate at a density of 65,000 cells per well. To inhibit glial overgrowth, 200 μM fluorodeoxyuridine (FUDR, Sigma) was added following 4 days of in vitro culture (DIV).

Neurons were transfected using the calcium phosphate method [Graham, F. L. & Eb, A. J. *A Virology* 52, 456-467 (1973)]. Briefly, the medium of primary hippocampal neurons cultured in a 24 wells plate was collected and replaced with 400 μl serum-free MEM medium (ThermoFisher scientific). 30 μl transfection mix (2 μg plasmid DNA and 250 μM $CaCl_2$ in HBS at pH 7.05) were added per well. Following a 1 hour incubation the cells were washed twice with MEM and the medium was changed back to the collected original medium. Cultured neurons were used between 14-21 DIV for experiments. The following plasmids were used in this study: pcDNA3.1-GIRK2.1 [Lesage F et al. FEBS Lett. (1994) October 10; 353(1):37-42], pAAV-CamKIIα-OPN3-mScarlet, pAAV-CamKIIα-eOPN3-mScarlet, pAAV-CamKIIα-PufTMT-mScarlet, pAAV-CamKIIα-OPN3-M4-mScarlet, pAAV-CamKIIα-PufTMT-M4-mScarlet, pAAV-CamKIIα-eYFP, pAAV-CamKIIα-PdCO2-mScarlet, pAAV-CamKIIα-LcPP-mScarlet, pAAV-CamKIIα-medakaTMT1A-mScarlet, pAAV-CamKIIα-zPP1-mScarlet, pAAV-CamKIIα-pPP2-mScarlet.

Confocal imaging and quantification—Primary cultured hippocampal neurons were transfected at 5 DIV with plasmids encoding a rhodopsin protein (mScarlet, OPN3, PufTMT, OPN3-M4, PufTMT-M4, eOPN3) along with pAAV-CamKIIα-eYFP. Four days following transfection, cells were fixed and permeabilized, washed 4 times with PBS and stained for 3 min with DAPI (5 mg/ml solution diluted 1:30,000 prior to staining). Coverslips were then mounted using PVA-DABCO (Sigma) and allowed to dry. Images of mScarlet and EYFP fluorescence were acquired using a Zeiss LSM 700 confocal microscope with a 20× magnification objective. Fluorescence was quantified using ImageJ {Schindelin:2012ir} by marking a region containing the somatic cytoplasm using the EYFP fluorescence and then measuring the average pixel intensity in the red imaging channel.

In vitro electrophysiology—Whole-cell patch clamp recordings were performed under visual control using differential interference contrast infrared (DIC-IR) illumination on an Olympus IX-71 microscope equipped with a monochrome scientific CMOS camera (Andor Neo). Borosilicate glass pipettes (Sutter Instrument BF100-58-10) with resistances ranging from 3-7 M1 were pulled using a laser micropipette puller (Sutter Instrument Model P-2000). For hippocampal neuron cultures, electrophysiological recordings from neurons were obtained in Tyrode's medium ([mM] 150 NaCl, 4 KCl, 2 $MgCl_2$, 2 $CaCl_2$, 10 D-glucose, 10 HEPES; 320 mOsm; pH adjusted to 7.35 with NaOH). The recording chamber was perfused at 0.5 ml $min^{-1}$ and maintained at 29-32° C. Pipettes were filled using a potassium gluconate-based intracellular solution ([mM] 135 K-gluconate, 4 KCl, 2 NaCl, 10 HEPES, 4 EGTA, 4 MgATP, 0.3 NaGTP; 280 mOsm $kg^{-1}$; pH adjusted to 7.3 with KOH). Whole-cell voltage clamp recordings were performed using a MultiClamp 700B amplifier, filtered at 8 kHz and digitized at 20 kHz using a Digidata 1440A digitizer (Molecular Devices). Light was delivered using a Lumencor SpecraX light engine, using band-pass filters at 475/28, 542/27 and 632/22 nm (peak wavelength/bandwidth). Light power was calibrated to be identical at all three wavelengths to allow comparison of activation efficiency. Remaining photon flux differences were less than 6%.

In vivo optogenetic silencing: AAV vectors encoding eOPN3 (AAV2/1&2.CamKIIα.eOPN3-mScarlet) or eYFP (AAV2/1&2.CamKIIα.eYFP.WPRE) were bilaterally injected into the auditory cortex (AP:−2.8 mm, ML: +/−4.15 mm DV:−2.8 mm) and medial *geniculate* nucleus/auditory thalamus (AP:−3.2 mm, ML: +/−1.8 mm DV:−3.65 mm). Optical fibers (200 μm diameter, NA 0.5) were bilaterally implanted above the amygdala complex (AP:−1.5 mm, ML: +/−3.0 mm DV:−4.3 mm). Mice were allowed to recover for 8-10 weeks to allow for viral expression. Prior to fear conditioning, mice were habituated to optical patch cord connection for 8 minutes on two consecutive days in the box used to transfer them from home cage to behavior room. Mice in both the eOPN3 and control group were placed in the fear conditioning chamber (Med Associates) in context A, allowed 10 minutes of habituation and then presented with five pairings of the CS (50 ms-long 5 kHz tones, delivered at 10 Hz for 30 s) and US (continuous 0.5 mA constant current foot shock for 1 second delivered with a standalone aversive stimulator, ENV-414S, Med Associates Inc., St. Albans, Vermont). Each CS co-terminated with a US, with a 60 seconds interval between CS-US pairings. On day 2 and 3, mice underwent a cued recall/extinction-learning test. These experiments were conducted in context B, which differed from context A in texture, odor and ambient light. Mice were presented with 20 repetitions of the CS, separated by 60 seconds intervals. During the extinction session, light (540 nm at 10 mW) was delivered during as well as 2 seconds prior and after CS representation. Six weeks following fear conditioning, mice were re-exposed to the fear-conditioning context for 15 minutes (renewal). Starting at minute 5, light pulses (1 s, 540 nm at 10 mW at 0.1 Hz) were delivered bilaterally through the fiber implants. Starting minute 10, a CS (50 ms-long 5 kHz tones, delivered at 10 Hz for 5 mins) was presented. Movies recorded at 40 frames per second were automatically scored for freezing by a custom written Fiji script (Schindelin, et al., 2012). To measure freezing bouts, for each frame the number of pixels with altered values compared to the previous frame were quantified. These values were temporally filtered by a Gaussian filter with 3 frames standard deviation. Only changed pixels around the mouse body were considered, to discard artifacts arising from patch-cord motion. A freezing threshold was set automatically per mouse and behavioral session by detection of the minimum in the distributions for freezing and motion peaks in the pixel change histogram. A mouse was considered to be freezing if 60 consecutive values (1.5 s) were below the freezing threshold.

Example 1

Exogenous Expression of Bistable Type II Opsins in Neurons

Recent work has identified a family of rhodopsins that exist in a wide range of organisms that are intrinsically bistable (FIG. 1A-B, PufTMT and MosOPN3), i.e. remain bound to the retinal chromophore after illumination and display prolonged signal transduction following a single illumination pulse (Koyanagi et al., 2013).

The present inventors tested several photoreceptors of this family for expression in mammalian neurons. To this end, primary cultured hippocampal neurons were transduced with mammalian codon-optimized version of PuffMT or MosOPN3. As shown in FIGS. 3A-B, the expression levels of both rhodopsins were low compared with a control vector comprising only the mScarlet fluorescent protein and mostly intracellular. In the next step, primary cultured hippocampal neurons were transduced with a chimeric photoreceptor composed of transmembrane and extracellular domains of bistable invertebrate rhodopsin and the intracellular domain of the M4 acetylcholine receptor, in order to recapitulate the M4 signaling pathway. The DREADD receptor hM4D in combination with its cognate ligand have been suggested as an attractive alternative to optogenesics for manipulation of presynaptic terminals. As shown in FIGS. 3A-B, the chimeric PuffMT-M4 did not show any detectable expression, while expression of the OPN3-M4 chimera was higher compared to the native OPN3 protein. However, expression of the OPN3-M4 was limited to the cytoplasm and almost no expression was detected on the membrane of the cells (FIG. 3C).

Following, in order to induce membrane expression of MosOPN3, primary cultured hippocampal neurons were transduced with a modified MosOPN3, referred to herein as eOPN3, which comprised an ER-export signal along with a membrane trafficking motif yielding (MosOPN3-ts-mScarlet-ER). Indeed, this modified eOPN3 was highly expressed in cultured hippocampal neurons compared with the native OPN3 and showed increased membrane targeting compared with the OPN3-M4 chimera (FIGS. 3A-C).

Example 2

Bistable Type II Opsins Exogenously Expressed in Neurons are Functional and Inhibit Presynaptic Transmission To test for functional activation of the G coupled Gi/o pathway by these novel engineered bistable rhodopsins, whole-cell recordings were conducted in neurons co-transfected with plasmids encoding eOPN3 with the G protein-gated potassium channel GIRK2.1. This configuration allowed quantification of $G_{i/o}$ pathway activity through the measurement of GIRK2-1-mediated hyperpolarizing $K^+$-currents. The endogenous expression of GIRK2-1 in neuronal cell types (Lüscher & Slesinger, 2010) and its ability to form functional homotetramers (Whorton & MacKinnon, 2011) make GIRK2-1 well suited as a reporter of $G_{i/o}$ pathway activation in neurons. In neurons expressing OPN3 and eOPN3 robust outward currents were recorded upon illumination with UV, blue, green and red light, with a maximum response at 560 nm (FIGS. 4A-B), consistent with previous characterization of light absorption of this rhodopsin.

Expression of exogenous proteins in mammalian neurons can lead to undesired consequences, from impaired cell health to light- or ligand-independent effects on the physiological activity or signal transduction pathways. To this end, changes in the intrinsic excitability of neurons expressing OPN3 or eOPN3 were evaluated. No significant difference between neurons expressing OPN3-mScarlet or eOPN3-mScarlet and neighboring non-expressing cells (FIGS. 5A-B). Hence, the eOPN3 variant is well-tolerated in mammalian neurons its expression does not trigger any light-independent physiological changes in neuronal excitability.

Example 3

Exogenous Expression of Bistable Type II Opsins Inhibits Presynaptic Transmission In-Vivo To verify that eOPN3-mediated presynaptic silencing can be utilized in a behavioral setting, eOPN3 was applied to suppress auditory input to the amygdala during recall and renewal of auditory-cued fear conditioning [FIG. 6A, (Tovote, et al., 2015)]. The amygdala plays a central role in the acquisition as well as the recall of the conditioned freezing response (LeDoux, 2000). Thus, inhibition of terminals from the medial geniculate nucleus (MGN) and the auditory cortex (ACtx) during the delivery of the conditioned stimulus (CS) should suppress the expression of the cue-triggered freezing response (Nabavi, et al., 2014; Kim & Cho, 2017). To this end, mice were bilaterally injected with AAV encoding eOPN3 or a fluorophore-only control vector into the MGN and the ACtx and 200 μm-diameter optical fibers were implanted above the amygdala (FIG. 6B). Following 8-10 weeks of recovery, mice underwent fear conditioning in context A (FIG. 6C), leading to similar freezing levels to the last tone as measured for control mice (FIG. 6D, "Acquisition"; unpaired two-sample Wilcoxon test, p=0.90). During the extinction session, photoactivation of eOPN3 led to a trend of reduced tone-evoked freezing during the first tone block compared with the control group (FIG. 6D, "Extinction"). In contrast, freezing levels were similar between the two groups during a cued recall experiment when no light was delivered (FIG. 6D, "Recall"). To further test the impact of eOPN3 activation in auditory afferents to the BLA on cue-evoked freezing responses, a fear renewal experiment was performed (FIG. 6D, "Renewal"). In this experimental session, the mice were allowed to habituate for 10 minutes in context A. Following 10 minutes in context A, both eOPN3-expressing as well as control mice showed low freezing rates (22.9% and 23.1% for eOPN3- and ctrl-mice, respectively). All mice were then exposed to the CS for 5 additional minutes. Activation of eOPN3 in auditory afferents to the amygdala was initiated 5 minutes after the beginning of the experiment and persisted throughout the 5 minutes of tone presentation, allowing assessing the effects of this manipulation both on contextual and cued freezing.

To activate eOPN3, 1 s light pulses (10 mW) were bilaterally delivered every 10 seconds. Activation of eOPN3 had no effect on context-evoked freezing. However, eOPN3-expressing mice showed reduced CS-evoked freezing during the 5 minutes of CS presentation (FIG. 6D, "Renewal"), indicating that eOPN3 can effectively suppress the activity of MGN and ACtx terminals in the amygdala. Across individual mice, freezing responses were negatively correlated with eOPN3-mScarlet expression levels in the experimental group but showed no correlation with eYFP expression levels in the control group (FIG. 6E).

Taken together, the results demonstrate that eOPN3 can be used for synaptic terminal inhibition in behaving animals, with a high light-sensitivity and a precise timed onset.

Example 4

Exogenous Expression of Bistable Type II Opsins and Switchable Control of Presynaptic Transmission As shown for OPN3, cloning of the opsin-mScarlet in frame with an ER-export signal and a membrane trafficking sequence (yielding eOPN3) increased exogenous expression and membrane targeting in cultured hippocampal neurons. Hence, other bistable type-II opsins were cloned with the same strategy to test for functional activation of the G coupled Gi/o pathway. As with the eOPN3, the ability to evoke GIRK mediated photocurrents, when co-transfected with the G protein-gated potassium channel GIRK2.1, was tested. PdCO2, LcPP, medakaTMT1A, zPP1 and pPP2 where well tolerated and coupling to GIRK was achieved by ultraviolet to blue light (FIG. 7A). Moreover, most bi-stable opsins could be completely deactivated with application of red shifted light for 5-10 seconds, enabling bimodal control over the opsins by light (FIG. 7A, green and yellow bars).

For neuronal cultures expressing PdCO2, blue light activation led to GIRK mediated photocurrents as well (FIG. 7B, upper trace), demonstrating the ability to also activate endogenous GIRK channels by PdCO2 activation. In addition, the normalized mEPSC frequency was reduced to about 50% when PdCO2 was once activated and only returned to the baseline frequency when PdCO2 was inactivated with green light, 100s post activation (FIG. 7B, lower trace and plots). Notably, mEPSC frequency reduction duration exceeded the occurrence of GIRK mediated photocurrents, demonstrating the ability for long term inhibition of synaptic transmission that is not coupled to GIRK activity.

Due to the bi-stable nature of these opsins, they can be activated, inactivated and reactivated again. As shown before (FIGS. 7A-B), blue and green light were successively applied for activation and deactivation, respectively (FIG. 7C, upper panel). In successive trials, PdCO2 could reversibly and repetitively inhibit synaptic transmission (FIG. 7C).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited Throughout the Application

Airan, R. D., Thompson, K. R., Fenno, L. E., Bernstein, H., Deisseroth, K., 2009. Temporally precise in vivo control of intracellular signalling. Nature 458, 1025-1029. doi:10.1038/nature07926

Basu, J., Zaremba, J. D., Cheung, S. K., Hitti, F. L., Zemelman, B. V., Losonczy, A., Siegelbaum, S. A., 2016. Gating of hippocampal activity, plasticity, and memory by entorhinal cortex long-range inhibition. Science (New York, N. Y 351, aaa5694-aaa5694. doi:10.1126/science.aaa5694

Creed, M., Pascoli, V. J., Luscher, C., 2015. Addiction therapy. Refining deep brain stimulation to emulate optogenetic treatment of synaptic pathology. Science (New York, N.Y 347, 659-664. doi:10.1126/science.1260776

Dobrunz, L. E., Huang, E. P., Stevens, C. F., 1997. Very short-term plasticity in hippocampal synapses. Proceedings of the National Academy of Sciences of the United States of America 94, 14843-14847.

Isoldi, M. C., Rollag, M. D., Castrucci, A. M. de L., Provencio, I., 2005. Rhabdomeric phototransduction initiated by the vertebrate photopigment melanopsin. Proceedings of the National Academy of Sciences of the United States of America 102, 1217-1221. doi:10.1073/pnas.0.0409252102

Klavir, O., Prigge, M., Sarel, A., Paz, R., Yizhar, O., 2017. Manipulating fear associations via optogenetic modulation of amygdala inputs to prefrontal cortex. Nat. Neurosci. 20, 836-844. doi:10.1038/nn.4523

Koyanagi, M., Takada, E., Nagata, T., Tsukamoto, H., Terakita, A., 2013. Homologs of vertebrate Opn3 potentially serve as a light sensor in nonphotoreceptive tissue. Proc Natl Acad Sci USA 110, 4998-5003. doi:10.1073/pnas.1219416110

Mahn, M., Gibor, L., Patil, P., Cohen-Kashi Malina, K., Oring, S., Printz, Y., Levy, R., Lampl, I., Yizhar, O., 2018. High-efficiency optogenetic silencing with soma-targeted anion-conducting channelrhodopsins. Nat Commun 9, 4125. doi:10.1038/s41467-018-06511-8

Mahn, M., Prigge, M., Ron, S., Levy, R., Yizhar, O., 2016. Biophysical constraints of optogenetic inhibition at presynaptic terminals. Nat. Neurosci. 19, 554-556. doi:10.1038/nn.4266 Nabavi, S., Fox, R., Proulx, C. D., Lin, J. Y., Tsien, R. Y., Malinow, R., 2014. Engineering a memory with LTD and LTP. Nature 511, 348-352.

Segal, M. M., 1991. Epileptiform activity in microcultures containing one excitatory hippocampal neuron. J Neurophysiol 65, 761-770. doi:10.1152/jn.1991.65.4.761

Stachniak, T. J., Ghosh, A., Sternson, S. M., 2014. Chemogenetic synaptic silencing of neural circuits localizes a hypothalamus→midbrain pathway for feeding behavior. Neuron 82, 797-808. doi:10.1016/j.neuron.2014.04.008 Sternson, S. M., Roth, B. L., 2014. Chemogenetic tools to interrogate brain functions. Annu. Rev.

Neurosci. 37, 387-407. doi:10.1146/annurev-neuro-071013-014048

Wiegert, J. S., Mahn, M., Prigge, M., Printz, Y., Yizhar, O., 2017. Silencing Neurons: Tools, Applications, and Experimental Constraints. Neuron 95, 504-529. doi:10.1016/j.neuron.2017.06.050

Wu, L. G., Saggau, P., 1994. Adenosine inhibits evoked synaptic transmission primarily by reducing presynaptic calcium influx in area CA1 of hippocampus. Neuron 12, 1139-1148.

Yizhar, O., Fenno, L. E., Davidson, T. J., Mogri, M., Deisseroth, K., 2011. Optogenetics in neural systems. Neuron 71, 9-34. doi:10.1016/j.neuron.2011.06.004

Zhu, H., Roth, B. L., 2014. Silencing synapses with DREADDs. Neuron 82, 723-725. doi:10.1016/j.neuron.2014.05.002

Zurawski, Z., Yim, Y. Y., Alford, S., Hamm, H. E., 2019. The expanding roles and mechanisms of G protein-mediated presynaptic inhibition. J. Biol. Chem. 294, 1661-1670. doi:10.1074/jbc.TM118.004163

What is claimed is:

1. A polynucleotide encoding a polypeptide comprising an OPN3 bistable type II opsin and ER export and membrane trafficking signals of a protein expressed in neuronal cells, said signals being heterologous to said OPN3 bistable type II opsin, wherein said ER export signal comprises SEQ ID NO: 2 and said membrane trafficking signal comprises SEQ ID NO: 1.

2. The polynucleotide of claim 1, wherein a nucleic acid sequence encoding said bistable type II opsin is codon optimized to heterologous expression.

3. The polynucleotide of claim 1, wherein said OPN3 is mosquito OPN3 (MosOpn3).

4. A nucleic acid construct comprising the polynucleotide of claim 1, and a regulatory element for directing expression of said polynucleotide in a cell.

5. A cell comprising the polynucleotide of claim 1.

* * * * *

SEQUENCE LISTING

```
<160> NUMBER OF SEQ ID NOS: 44

<210> SEQ ID NO 1
<211> LENGTH: 20
<212> TYPE: PRT
<213> ORGANISM: Artificial sequence
<220> FEATURE:
<223> OTHER INFORMATION: Membrane trafficking signal

<400> SEQUENCE: 1

Lys Ser Arg Ile Thr Ser Glu Gly Glu Tyr Ile Pro Leu Asp Gln Ile
1               5                   10                  15

Asp Ile Asn Val
            20

<210> SEQ ID NO 2
<211> LENGTH: 7
<212> TYPE: PRT
<213> ORGANISM: Artificial sequence
<220> FEATURE:
```

<223> OTHER INFORMATION: ER EXPORT SIGNAL

<400> SEQUENCE: 2

Phe Cys Tyr Glu Asn Glu Val
1               5

<210> SEQ ID NO 3
<211> LENGTH: 9
<212> TYPE: PRT
<213> ORGANISM: Artificial sequence
<220> FEATURE:
<223> OTHER INFORMATION: Rhodopsin epitope tag

<400> SEQUENCE: 3

Thr Glu Thr Ser Gln Val Ala Pro Ala
1               5

<210> SEQ ID NO 4
<211> LENGTH: 6
<212> TYPE: PRT
<213> ORGANISM: Artificial sequence
<220> FEATURE:
<223> OTHER INFORMATION: Linker sequence

<400> SEQUENCE: 4

Pro Arg Ala Arg Asp Pro
1               5

<210> SEQ ID NO 5
<211> LENGTH: 607
<212> TYPE: PRT
<213> ORGANISM: Artificial sequence
<220> FEATURE:
<223> OTHER INFORMATION: eOPN3-mScarlet open reading frame AA sequence

<400> SEQUENCE: 5

Met Tyr Asp Ala Pro Asn Asp Val Ala Ser Ser Val Ala Asp Tyr Glu
1               5                   10                  15

Asp Leu Met Ala Pro Trp Ala Tyr Asn Ala Ala Ala Ile Thr Leu Phe
            20                  25                  30

Phe Ile Gly Phe Phe Gly Phe Phe Leu Asn Leu Phe Val Ile Ala Leu
        35                  40                  45

Met Ser Lys Asp Met Gln Leu Trp Thr Pro Met Asn Ile Ile Leu Phe
    50                  55                  60

Asn Leu Val Cys Ser Asp Phe Ser Val Ser Ile Ile Gly Asn Pro Leu
65                  70                  75                  80

Thr Leu Thr Ser Ala Ile Ser His Arg Trp Ile Phe Gly Arg Thr Leu
                85                  90                  95

Cys Val Ala Tyr Gly Phe Phe Met Ser Leu Leu Gly Ile Thr Ser Ile
                100                 105                 110

Thr Thr Leu Thr Val Leu Ser Tyr Glu Arg Tyr Cys Leu Ile Ser Arg
        115                 120                 125

Pro Phe Ser Ser Arg Asn Leu Ser Arg Lys Gly Ala Phe Leu Ala Ile
        130                 135                 140

Phe Phe Ile Trp Gly Tyr Ser Phe Ala Leu Thr Ser Pro Pro Leu Phe
145                 150                 155                 160

Gly Trp Gly Ala Tyr Val Gln Glu Ala Ala Asn Ile Ser Cys Ser Val
                165                 170                 175

Asn Trp Glu Ser Gln Thr Lys Asn Ala Thr Thr Tyr Ile Ile Phe Leu
            180                 185                 190

-continued

```
Phe Val Phe Gly Leu Val Val Pro Leu Ile Val Ile Val Tyr Ser Tyr
        195                 200                 205

Thr Asn Ile Ile Val Tyr Met Arg Arg Asn Ser Ala Arg Val Gly Arg
        210                 215                 220

Ile Asn Arg Ala Glu Gln Arg Val Thr Ser Met Val Ala Val Met Ile
225                 230                 235                 240

Val Ala Phe Met Val Ala Trp Thr Pro Tyr Ala Ile Phe Ala Leu Ile
                245                 250                 255

Glu Gln Phe Gly Pro Pro Glu Leu Ile Gly Pro Gly Leu Ala Val Leu
                260                 265                 270

Pro Ala Leu Ile Ala Lys Ser Ser Ile Cys Tyr Asn Pro Ile Ile Tyr
                275                 280                 285

Val Gly Met Asn Thr Gln Phe Arg Ala Ala Phe Thr Arg Val Arg Asn
        290                 295                 300

Lys Gly Gly Val Pro Thr Ala Asp Gln Asn Thr Thr Thr Met Gln Arg
305                 310                 315                 320

Glu Leu Thr Lys Ser Ser Arg Asp Met Val Thr Glu Thr Ser Gln Val
                325                 330                 335

Ala Pro Ala Pro Arg Ala Arg Asp Pro Thr Gly Lys Ser Arg Ile Thr
                340                 345                 350

Ser Glu Gly Glu Tyr Ile Pro Leu Asp Gln Ile Asp Ile Asn Val Val
        355                 360                 365

Met Val Ser Lys Gly Glu Ala Val Ile Lys Glu Phe Met Arg Phe Lys
        370                 375                 380

Val His Met Glu Gly Ser Met Asn Gly His Glu Phe Glu Ile Glu Gly
385                 390                 395                 400

Glu Gly Glu Gly Arg Pro Tyr Glu Gly Thr Gln Thr Ala Lys Leu Lys
                405                 410                 415

Val Thr Lys Gly Gly Pro Leu Pro Phe Ser Trp Asp Ile Leu Ser Pro
                420                 425                 430

Gln Phe Met Tyr Gly Ser Arg Ala Phe Thr Lys His Pro Ala Asp Ile
                435                 440                 445

Pro Asp Tyr Tyr Lys Gln Ser Phe Pro Glu Gly Phe Lys Trp Glu Arg
        450                 455                 460

Val Met Asn Phe Glu Asp Gly Gly Ala Val Thr Val Thr Gln Asp Thr
465                 470                 475                 480

Ser Leu Glu Asp Gly Thr Leu Ile Tyr Lys Val Lys Leu Arg Gly Thr
                485                 490                 495

Asn Phe Pro Pro Asp Gly Pro Val Met Gln Lys Lys Thr Met Gly Trp
                500                 505                 510

Glu Ala Ser Thr Glu Arg Leu Tyr Pro Glu Asp Gly Val Leu Lys Gly
                515                 520                 525

Asp Ile Lys Met Ala Leu Arg Leu Lys Asp Gly Gly Arg Tyr Leu Ala
        530                 535                 540

Asp Phe Lys Thr Thr Tyr Lys Ala Lys Lys Pro Val Gln Met Pro Gly
545                 550                 555                 560

Ala Tyr Asn Val Asp Arg Lys Leu Asp Ile Thr Ser His Asn Glu Asp
                565                 570                 575

Tyr Thr Val Val Glu Gln Tyr Glu Arg Ser Glu Gly Arg His Ser Thr
        580                 585                 590

Gly Gly Met Asp Glu Leu Tyr Lys Phe Cys Tyr Glu Asn Glu Val
        595                 600                 605
```

<210> SEQ ID NO 6
<211> LENGTH: 1824
<212> TYPE: DNA
<213> ORGANISM: Artificial sequence
<220> FEATURE:
<223> OTHER INFORMATION: eOPN3 nucleic acid sequence

<400> SEQUENCE: 6

```
atgtacgacg ccccccaacga cgtggccagc agcgtggccg actacgagga cctgatggcc      60
ccctgggcct acaacgccgc cgccatcacc ctgttcttca tcggcttctt cggcttcttc     120
ctgaacctgt tcgtgatcgc cctgatgagc aaggacatgc agctgtggac ccccatgaac     180
atcatcctgt tcaacctggt gtgcagcgac ttcagcgtga gcatcatcgg caacccccctg     240 accctgacca gcgccatcag ccacaggtgg atcttcggca ggaccctgtg cgtggcctac     300
ggcttcttca tgagcctgct gggcatcacc agcatcacca ccctgaccgt gctgagctac     360
gagaggtact gcctgatcag caggcccttc agcagcagga acctgagcag gaagggcgcc     420
ttcctggcca tcttcttcat ctggggctac agcttcgccc tgaccagccc ccccctgttc     480
ggctggggcg cctacgtgca ggaggccgcc aacatcagct gcagcgtgaa ctgggagagc     540
cagaccaaga cgccaccac ctacatcatc ttcctgttcg tgttcggcct ggtggtgccc     600
ctgatcgtga tcgtgtacag ctacaccaac atcatcgtgt acatgaggag gaacagcgcc     660
agggtgggca ggatcaacag ggccgagcag agggtgacca gcatggtggc cgtgatgatc     720
gtggccttca tggtggcctg gacccccctac gccatcttcg ccctgatcga gcagttcggc     780 cccccccgagc tgatcggccc tggactggct gtgctgcctg ctctgatcgc caagagcagc     840
atctgctaca accccatcat ctacgtgggc atgaacaccc agttcagggc cgccttcacc     900
agggtgagga caaagggcgg cgtgcccacc gccgaccaga acaccaccac catgcagagg     960
gagctgacca agagcagcag ggacatggtg accgagacca gccaggtggc tcctgctccg    1020
cgagcccgag atccaaccgg taagagcagg atcaccagcg agggcgagta catcccccctg    1080 gaccagatcg acatcaacgt ggtgatggtg agcaagggcg aggcagtgat caaggagttc    1140
atgcggttca aggtgcacat ggagggctcc atgaacggcc acgagttcga gatcgagggc    1200
gagggcgagg ccgcccccta cgagggcacc cagaccgcca agctgaaggt gaccaagggt    1260
ggccccctgc ccttctcctg ggacatcctg tcccctcagt tcatgtacgg ctccagggcc    1320
ttcaccaagc accccgccga catccccgac tactataagc agtccttccc cgagggcttc    1380
aagtgggagc gcgtgatgaa cttcgaggac ggcggcgccg tgaccgtgac ccaggacacc    1440
tccctggagg acggcaccct gatctacaag gtgaagctcc gcggcaccaa cttccctcct    1500
gacggccccg taatgcagaa gaagacaatg ggctggaag cgtccaccga gcggttgtac    1560
cccgaggacg gcgtgctgaa gggcgacatt aagatggccc tgcgcctgaa ggacggcgga    1620
cgctacctgg cggacttcaa gaccacctac aaggccaaga gcccgtgca gatgcccggc    1680 gcctacaacg tcgaccgcaa gttggacatc acctcccaca cgaggacta caccgtggtg    1740 gaacagtacg aacgctccga gggccgccac tccaccggcg gcatggacga gctgtacaag    1800
ttctgctacg agaacgaggt gtaa                                          1824
```

<210> SEQ ID NO 7
<211> LENGTH: 696
<212> TYPE: DNA
<213> ORGANISM: Artificial sequence
<220> FEATURE:
<223> OTHER INFORMATION: mScarlet NA sequence -continued

```
<400> SEQUENCE: 7
atggtgagca agggcgaggc agtgatcaag gagttcatgc ggttcaaggt gcacatggag      60
ggctccatga acggccacga gttcgagatc gagggcgagg gcgagggccg cccctacgag     120
ggcacccaga ccgccaagct gaaggtgacc aagggtggcc ccctgccctt ctcctgggac     180
atcctgtccc ctcagttcat gtacggctcc agggccttca ccaagcaccc cgccgacatc     240
cccgactact ataagcagtc cttccccgag ggcttcaagt gggagcgcgt gatgaacttc     300
gaggacggcg cgccgtgac cgtgacccag gacacctccc tggaggacgg caccctgatc      360
tacaaggtga agctccgcgg caccaacttc cctcctgacg gccccgtaat gcagaagaag     420
acaatgggct gggaagcgtc caccgagcgg ttgtaccccg aggacggcgt gctgaagggc     480
gacattaaga tggccctgcg cctgaaggac ggcggacgct acctggcgga cttcaagacc     540
acctacaagg ccaagaagcc cgtgcagatg cccggcgcct acaacgtcga ccgcaagttg     600
gacatcacct cccacaacga ggactacacc gtggtggaac agtacgaacg ctccgagggc     660
cgccactcca ccggcggcat ggacgagctg tacaag                               696

<210> SEQ ID NO 8
<211> LENGTH: 429
<212> TYPE: PRT
<213> ORGANISM: Artificial sequence
<220> FEATURE:
<223> OTHER INFORMATION: mosopn3 aa sequence

<400> SEQUENCE: 8

Met Tyr Asp Ala Pro Asn Asp Val Ala Ser Ser Val Ala Asp Tyr Glu
1               5                   10                  15

Asp Leu Met Ala Pro Trp Ala Tyr Asn Ala Ala Ala Ile Thr Leu Phe
            20                  25                  30

Phe Ile Gly Phe Phe Gly Phe Phe Leu Asn Leu Phe Val Ile Ala Leu
        35                  40                  45

Met Ser Lys Asp Met Gln Leu Trp Thr Pro Met Asn Ile Ile Leu Phe
    50                  55                  60

Asn Leu Val Cys Ser Asp Phe Ser Val Ser Ile Ile Gly Asn Pro Leu
65                  70                  75                  80

Thr Leu Thr Ser Ala Ile Ser His Arg Trp Ile Phe Gly Arg Thr Leu
                85                  90                  95

Cys Val Ala Tyr Gly Phe Phe Met Ser Leu Leu Gly Ile Thr Ser Ile
            100                 105                 110

Thr Thr Leu Thr Val Leu Ser Tyr Glu Arg Tyr Cys Leu Ile Ser Arg
        115                 120                 125

Pro Phe Ser Ser Arg Asn Leu Ser Arg Lys Gly Ala Phe Leu Ala Ile
        130                 135                 140

Phe Phe Ile Trp Gly Tyr Ser Phe Ala Leu Thr Ser Pro Pro Leu Phe
145                 150                 155                 160

Gly Trp Gly Ala Tyr Val Gln Glu Ala Ala Asn Ile Ser Cys Ser Val
                165                 170                 175

Asn Trp Glu Ser Gln Thr Lys Asn Ala Thr Thr Tyr Ile Ile Phe Leu
            180                 185                 190

Phe Val Phe Gly Leu Val Val Pro Leu Ile Val Ile Val Tyr Ser Tyr
            195                 200                 205

Thr Asn Ile Ile Val Tyr Met Arg Arg Asn Ser Ala Arg Val Gly Arg
    210                 215                 220

Ile Asn Arg Ala Glu Gln Arg Val Thr Ser Met Val Ala Val Met Ile
```

-continued

```
225               230               235               240

Val Ala Phe Met Val Ala Trp Thr Pro Tyr Ala Ile Phe Ala Leu Ile
              245               250               255

Glu Gln Phe Gly Pro Pro Glu Leu Ile Gly Pro Gly Leu Ala Val Leu
              260               265               270

Pro Ala Leu Ile Ala Lys Ser Ser Ile Cys Tyr Asn Pro Ile Ile Tyr
              275               280               285

Val Gly Met Asn Thr Gln Phe Arg Ala Ala Phe Thr Arg Val Arg Asn
              290               295               300

Lys Gly Gly Val Pro Thr Ala Asp Gln Asn Thr Thr Thr Met Gln Arg
305               310               315               320

Glu Leu Thr Lys Ser Ser Arg Asp Met Val Glu Cys Ser Phe Asp Phe
              325               330               335

Cys Arg Lys Lys Asn Arg Phe Lys Ile Ser Leu Val Lys Pro Thr Ala
              340               345               350

Pro Leu Ala Val Val Asp Val Ser Ser Ser Ser His Pro Gly Lys Val
              355               360               365

Thr Ser Arg Ser Pro Leu Asp Gln Thr Val Leu Asn Glu Met Asn Asp
              370               375               380

Glu Glu Arg Gly Arg Glu Arg Ser Gly Ala Gly Tyr Ala Gly Ser Arg
385               390               395               400

Phe Val Arg Pro Asp Phe Glu Leu Ser Val Ile Asn Ser Gly Lys Ser
              405               410               415

Ile Leu Ile Lys Ser Lys Asn Phe Arg Ser Asn Leu Leu
              420               425
```

```
<210> SEQ ID NO 9
<211> LENGTH: 330
<212> TYPE: PRT
<213> ORGANISM: Artificial sequence
<220> FEATURE:
<223> OTHER INFORMATION: mosopn3 mutant without the last 99 aa

<400> SEQUENCE: 9
```

```
Met Tyr Asp Ala Pro Asn Asp Val Ala Ser Ser Val Ala Asp Tyr Glu
1                 5                 10                15

Asp Leu Met Ala Pro Trp Ala Tyr Asn Ala Ala Ala Ile Thr Leu Phe
              20                25                30

Phe Ile Gly Phe Phe Gly Phe Phe Leu Asn Leu Phe Val Ile Ala Leu
              35                40                45

Met Ser Lys Asp Met Gln Leu Trp Thr Pro Met Asn Ile Ile Leu Phe
              50                55                60

Asn Leu Val Cys Ser Asp Phe Ser Val Ser Ile Ile Gly Asn Pro Leu
65                70                75                80

Thr Leu Thr Ser Ala Ile Ser His Arg Trp Ile Phe Gly Arg Thr Leu
              85                90                95

Cys Val Ala Tyr Gly Phe Phe Met Ser Leu Leu Gly Ile Thr Ser Ile
              100               105               110

Thr Thr Leu Thr Val Leu Ser Tyr Glu Arg Tyr Cys Leu Ile Ser Arg
              115               120               125

Pro Phe Ser Ser Arg Asn Leu Ser Arg Lys Gly Ala Phe Leu Ala Ile
              130               135               140

Phe Phe Ile Trp Gly Tyr Ser Phe Ala Leu Thr Ser Pro Pro Leu Phe
145               150               155               160

Gly Trp Gly Ala Tyr Val Gln Glu Ala Ala Asn Ile Ser Cys Ser Val
```

-continued

```
                   165              170              175
Asn Trp Glu Ser Gln Thr Lys Asn Ala Thr Thr Tyr Ile Ile Phe Leu
                180              185              190

Phe Val Phe Gly Leu Val Val Pro Leu Ile Val Ile Val Tyr Ser Tyr
            195              200              205

Thr Asn Ile Ile Val Tyr Met Arg Arg Asn Ser Ala Arg Val Gly Arg
        210              215              220

Ile Asn Arg Ala Glu Gln Arg Val Thr Ser Met Val Ala Val Met Ile
225              230              235              240

Val Ala Phe Met Val Ala Trp Thr Pro Tyr Ala Ile Phe Ala Leu Ile
                245              250              255

Glu Gln Phe Gly Pro Pro Glu Leu Ile Gly Pro Gly Leu Ala Val Leu
                260              265              270

Pro Ala Leu Ile Ala Lys Ser Ser Ile Cys Tyr Asn Pro Ile Ile Tyr
                275              280              285

Val Gly Met Asn Thr Gln Phe Arg Ala Ala Phe Thr Arg Val Arg Asn
            290              295              300

Lys Gly Gly Val Pro Thr Ala Asp Gln Asn Thr Thr Thr Met Gln Arg
305              310              315              320

Glu Leu Thr Lys Ser Ser Arg Asp Met Val
                325              330
```

<210> SEQ ID NO 10
<211> LENGTH: 288
<212> TYPE: PRT
<213> ORGANISM: Artificial sequence
<220> FEATURE:
<223> OTHER INFORMATION: PufTMT amino acid sequence

<400> SEQUENCE: 10

```
Met Ser Arg Thr Gly His Thr Val Val Ala Val Met Leu Gly Thr Ile
1               5               10              15

Leu Leu Ala Gly Val Phe Gly Asn Ser Val Val Phe Leu Val Phe Val
            20              25              30

Lys Tyr Arg Ser Leu Arg Thr Pro Ile Asn Leu Ile Leu Leu Asn Ile
        35              40              45

Ser Leu Ser Asp Ile Leu Val Cys Val Phe Gly Thr Pro Leu Ser Phe
    50              55              60

Ala Ala Ser Leu Lys Gly Arg Trp Leu Leu Gly Glu Arg Gly Cys Glu
65              70              75              80

Trp Tyr Gly Phe Ala Asn Ser Leu Phe Gly Ile Val Ser Leu Val Ser
                85              90              95

Leu Ser Val Leu Ser Tyr Glu Arg Tyr Thr Val Val Leu Gln Pro Thr
            100             105             110

Gln Val Asp Val Ser Tyr Phe Arg Lys Ala Trp Phe Cys Val Gly Gly
        115             120             125

Ser Trp Leu Tyr Ala Leu Phe Trp Thr Leu Pro Pro Leu Leu Gly Trp
    130             135             140

Ser Arg Tyr Gly Pro Glu Gly Pro Gly Thr Met Cys Ser Val Gln Trp
145             150             155             160

His Leu Arg Ser Pro Ala Asn Ile Ser Tyr Val Leu Cys Leu Phe Ile
            165             170             175

Phe Cys Leu Leu Leu Pro Leu Val Val Met Val Tyr Ser Tyr Gly Arg
            180             185             190

Ile Trp Val Ala Val Arg Arg Gln His Cys Ala Gln Ser His Leu Glu
```

-continued

```
            195                 200                 205

Ala Gly Arg Ile Asn Leu Leu Thr Ala Gln Arg Arg Glu Gln His Ile
    210                 215                 220

Leu Trp Met Val Leu Ser Met Val Ser Cys Tyr Met Leu Cys Trp Met
225                 230                 235                 240

Pro Tyr Gly Ile Ile Ala Leu Val Ala Thr Leu Gly Arg Leu Gly Pro
                245                 250                 255

Ile Ser Pro Ala Val Ser Val Val Pro Ser Ile Leu Ala Lys Phe Ser
                260                 265                 270

Thr Val Val Asn Pro Val Ile Tyr Met Phe Phe Asn Asn Gln Val Arg
            275                 280                 285

<210> SEQ ID NO 11
<211> LENGTH: 6
<212> TYPE: PRT
<213> ORGANISM: Artificial sequence
<220> FEATURE:
<223> OTHER INFORMATION: ER EXPORT SIGNAL
<220> FEATURE:
<221> NAME/KEY: misc_feature
<222> LOCATION: (2)..(2)
<223> OTHER INFORMATION: Xaa can be any naturally occurring amino acid

<400> SEQUENCE: 11

Phe Xaa Tyr Glu Asn Glu
1               5

<210> SEQ ID NO 12
<211> LENGTH: 5
<212> TYPE: PRT
<213> ORGANISM: Artificial sequence
<220> FEATURE:
<223> OTHER INFORMATION: ER EXPORT SIGNAL
<220> FEATURE:
<221> NAME/KEY: misc_feature
<222> LOCATION: (2)..(3)
<223> OTHER INFORMATION: Xaa can be any naturally occurring amino acid

<400> SEQUENCE: 12

Val Xaa Xaa Ser Leu
1               5

<210> SEQ ID NO 13
<211> LENGTH: 5
<212> TYPE: PRT
<213> ORGANISM: Artificial sequence
<220> FEATURE:
<223> OTHER INFORMATION: ER EXPORT SIGNAL

<400> SEQUENCE: 13

Val Lys Glu Ser Leu
1               5

<210> SEQ ID NO 14
<211> LENGTH: 5
<212> TYPE: PRT
<213> ORGANISM: Artificial sequence
<220> FEATURE:
<223> OTHER INFORMATION: ER EXPORT SIGNAL

<400> SEQUENCE: 14

Val Leu Gly Ser Leu
1               5

<210> SEQ ID NO 15
```

```
<211> LENGTH: 16
<212> TYPE: PRT
<213> ORGANISM: Artificial sequence
<220> FEATURE:
<223> OTHER INFORMATION: ER EXPORT SIGNAL

<400> SEQUENCE: 15

Asn Ala Asn Ser Phe Cys Tyr Glu Asn Glu Val Ala Leu Thr Ser Lys
1               5                   10                  15

<210> SEQ ID NO 16
<211> LENGTH: 26
<212> TYPE: PRT
<213> ORGANISM: Artificial sequence
<220> FEATURE:
<223> OTHER INFORMATION: MEMBRANE TRAFFICKING SIGNAL

<400> SEQUENCE: 16

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 17
<211> LENGTH: 26
<212> TYPE: PRT
<213> ORGANISM: Artificial sequence
<220> FEATURE:
<223> OTHER INFORMATION: MEMBRANE TRAFFICKING SIGNAL

<400> SEQUENCE: 17

Ala Gly His Ser Asn Ser Met Ala Leu Phe Ser Phe Ser Leu Leu Trp
1               5                   10                  15

Leu Cys Ser Gly Val Leu Gly Thr Glu Phe
            20                  25

<210> SEQ ID NO 18
<211> LENGTH: 23
<212> TYPE: PRT
<213> ORGANISM: Artificial sequence
<220> FEATURE:
<223> OTHER INFORMATION: MEMBRANE TRAFFICKING SIGNAL

<400> SEQUENCE: 18

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 19
<211> LENGTH: 18
<212> TYPE: PRT
<213> ORGANISM: Artificial sequence
<220> FEATURE:
<223> OTHER INFORMATION: MEMBRANE TRAFFICKING SIGNAL

<400> SEQUENCE: 19

Met Arg Gly Thr Pro Leu Leu Leu Val Val Ser Leu Phe Ser Leu Leu
1               5                   10                  15

Gln Asp

<210> SEQ ID NO 20
<211> LENGTH: 864
<212> TYPE: DNA
<213> ORGANISM: Artificial sequence
```

```
<220> FEATURE:
<223> OTHER INFORMATION: Codon optimized nucleic acid sequence of the
      MosOpn3

<400> SEQUENCE: 20
atgagcagga ccggccacac cgtggtggcc gtgatgctgg gcaccatcct gctggccggc      60
gtgttcggca acagcgtggt gttcctggtg ttcgtgaagt acaggagcct gaggaccccc     120
atcaacctga tcctgctgaa catcagcctg agcgacatcc tggtgtgcgt gttcggcacc     180
cccctgagct tcgccgccag cctgaagggc aggtggctgc tgggcgagag gggctgcgag     240
tggtacggct tcgccaacag cctgttcggc atcgtgagcc tggtgagcct gagcgtgctg     300
agctacgaga ggtacaccgt ggtgctgcag cccacccagg tggacgtgag ctacttcagg     360
aaggcctggt tctgcgtggg cggcagctgg ctgtacgccc tgttctggac cctgcctcct     420
ctgctgggct ggagcaggta cggccccgag ggccctggca ccatgtgcag cgtgcagtgg     480
cacctgagga gccccgccaa catcagctac gtgctgtgcc tgttcatctt ctgcctgctg     540
ctgcccctgg tggtgatggt gtacagctac ggcaggatct gggtggccgt gaggaggcag     600
cactgcgccc agagccacct ggaggccggc aggatcaacc tgctgaccgc ccagaggagg     660
gagcagcaca tcctgtggat ggtgctgagc atggtgagct gctacatgct gtgctggatg     720
ccctacggca tcatcgccct ggtggccacc ctgggcaggc tgggccccat cagccccgcc     780
gtgagcgtgg tgcccagcat cctggccaag ttcagcaccg tggtgaaccc cgtgatctac     840
atgttcttca caaccaggt gagg                                            864

<210> SEQ ID NO 21
<211> LENGTH: 990
<212> TYPE: DNA
<213> ORGANISM: Artificial sequence
<220> FEATURE:
<223> OTHER INFORMATION: Alternative Codon optimized nucleic acid
      sequence of the MosOpn3

<400> SEQUENCE: 21
atgtacgacg cccccaacga cgtggccagc agcgtggccg actacgagga cctgatggcc      60
ccctgggcct acaacgccgc cgccatcacc ctgttcttca tcggcttctt cggcttcttc     120
ctgaacctgt tcgtgatcgc cctgatgagc aaggacatgc agctgtggac ccccatgaac     180
atcatcctgt tcaacctggt gtgcagcgac ttcagcgtga gcatcatcgg caaccccctg     240
accctgacca gcgccatcag ccaccgctgg atcttcggcc gcaccctgtg cgtggcctac     300
ggcttcttca tgagcctgct gggcatcacc agcatcacca ccctgaccgt gctgagctac     360
gagcgctact gcctgatcag ccgccccttc agcagccgca acctgagccg caagggcgcc     420
ttcctggcca tcttcttcat ctgggctac agcttcgccc tgaccagccc ccccctgttc     480
ggctggggcg cctacgtgca ggaggccgcc aacatcagct gcagcgtgaa ctgggagagc     540
cagaccaaga cgccaccac ctacatcatc ttcctgttcg tgttcggcct ggtggtgccc     600
ctgatcgtga tcgtgtacag ctacaccaac atcatcgtgt acatgcgccg caacagcgcc     660
cgcgtgggcc gcatcaaccg cgccgagcag cgcgtgacca gcatggtggc cgtgatgatc     720
gtggccttca tggtggcctg gacccccctac gccatcttcg ccctgatcga gcagttcggc     780 cccccgagc tgatcggccc cggcctggcc gtgctgcccg ccctgatcgc caagagcagc     840
atctgctaca cccccatcat ctacgtgggc atgaacaccc agttccgcgc cgccttcacc     900
cgcgtgcgca acaagggcgg cgtgcccacc gccgaccaga acaccaccac catgcagcgc     960
```

-continued

```
gagctgacca agagcagccg cgacatggtg                                    990
```

```
<210> SEQ ID NO 22
<211> LENGTH: 864
<212> TYPE: DNA
<213> ORGANISM: Artificial sequence
<220> FEATURE:
<223> OTHER INFORMATION: Codon optimized nucleic acid sequence of the
      PufTMT

<400> SEQUENCE: 22
atgagcagga ccggccacac cgtggtggcc gtgatgctgg gcaccatcct gctggccggc    60
gtgttcggca acagcgtggt gttcctggtg ttcgtgaagt acaggagcct gaggaccccc   120
atcaacctga tcctgctgaa catcagcctg agcgacatcc tggtgtgcgt gttcggcacc   180
cccctgagct cgccgccag cctgaagggc aggtggctgc tgggcgagag gggctgcgag    240
tggtacggct cgccaacag cctgttcggc atcgtgagcc tggtgagcct gagcgtgctg    300
agctacgaga ggtacaccgt ggtgctgcag cccacccagg tggacgtgag ctacttcagg   360
aaggcctggt tctgcgtggg cggcagctgg ctgtacgccc tgttctggac cctgcctcct   420
ctgctgggct ggagcaggta cggccccgag ggccctggca ccatgtgcag cgtgcagtgg   480
cacctgagga gccccgccaa catcagctac gtgctgtgcc tgttcatctt ctgcctgctg   540
ctgcccctgg tggtgatggt gtacagctac ggcaggatct gggtggccgt gaggaggcag   600
cactgcgccc agagccacct ggaggccggc aggatcaacc tgctgaccgc ccagaggagg   660
gagcagcaca tcctgtggat ggtgctgagc atggtgagct gctacatgct gtgctggatg   720
ccctacggca tcatcgccct ggtggccacc ctgggcaggc tgggccccat cagccccgcc   780
gtgagcgtgg tgcccagcat cctggccaag ttcagcaccg tggtgaaccc cgtgatctac   840
atgttcttca caaccaggt gagg                                           864
```

```
<210> SEQ ID NO 23
<211> LENGTH: 864
<212> TYPE: DNA
<213> ORGANISM: Artificial sequence
<220> FEATURE:
<223> OTHER INFORMATION: Alternative Codon optimized nucleic acid
      sequence of the PufTMT

<400> SEQUENCE: 23
atgagccgca ccggccacac cgtggtggcc gtgatgctgg gcaccatcct gctggccggc    60
gtgttcggca acagcgtggt gttcctggtg ttcgtgaagt accgcagcct gcgcaccccc   120
atcaacctga tcctgctgaa catcagcctg agcgacatcc tggtgtgcgt gttcggcacc   180
cccctgagct cgccgccag cctgaagggc cgctggctgc tgggcgagcg cggctgcgag    240
tggtacggct cgccaacag cctgttcggc atcgtgagcc tggtgagcct gagcgtgctg    300
agctacgagc gctacaccgt ggtgctgcag cccacccagg tggacgtgag ctacttccgc   360
aaggcctggt tctgcgtggg cggcagctgg ctgtacgccc tgttctggac cctgcccccc   420
ctgctgggct ggagccgcta cggccccgag ggccccggca ccatgtgcag cgtgcagtgg   480
cacctgcgca gccccgccaa catcagctac gtgctgtgcc tgttcatctt ctgcctgctg   540
ctgcccctgg tggtgatggt gtacagctac ggccgcatct gggtggccgt gcgccgccag   600
cactgcgccc agagccacct ggaggccggc cgcatcaacc tgctgaccgc ccagcgccgc   660
gagcagcaca tcctgtggat ggtgctgagc atggtgagct gctacatgct gtgctggatg   720
ccctacggca tcatcgccct ggtggccacc ctgggccgcc tgggccccat cagccccgcc   780
```

-continued

```
gtgagcgtgg tgcccagcat cctggccaag ttcagcaccg tggtgaaccc cgtgatctac        840
atgttcttca acaaccaggt gcgc                                               864
```

<210> SEQ ID NO 24
<211> LENGTH: 5
<212> TYPE: PRT
<213> ORGANISM: Artificial sequence
<220> FEATURE:
<223> OTHER INFORMATION: repetetive amino acid sequence motif

<400> SEQUENCE: 24

Glu Ala Ala Ala Lys
1               5

<210> SEQ ID NO 25
<211> LENGTH: 354
<212> TYPE: PRT
<213> ORGANISM: Artificial sequence
<220> FEATURE:
<223> OTHER INFORMATION: PdCO2 aa sequence

<400> SEQUENCE: 25

Met Asp Gly Glu Asn Leu Thr Ile Pro Asn Pro Val Thr Glu Leu Met
1               5                   10                  15

Asp Thr Pro Ile Asn Ser Thr Tyr Phe Gln Asn Leu Asn Ala Glu Thr
                20                  25                  30

Asp Gly Gly Asn His Tyr Ile Tyr Asn Ala Phe Thr Ala Thr Asp Tyr
            35                  40                  45

Asn Ile Cys Ala Ala Tyr Leu Phe Phe Ile Ala Cys Leu Gly Val Ser
        50                  55                  60

Leu Asn Val Leu Val Leu Val Leu Phe Ile Lys Asp Arg Lys Leu Arg
65                  70                  75                  80

Ser Pro Asn Asn Phe Leu Tyr Val Ser Leu Ala Leu Gly Asp Leu Leu
                85                  90                  95

Val Ala Val Phe Gly Thr Ala Phe Lys Phe Ile Ile Thr Ala Arg Lys
            100                 105                 110

Thr Leu Leu Arg Glu Glu Asp Gly Phe Cys Lys Trp Tyr Gly Phe Ile
        115                 120                 125

Thr Tyr Leu Gly Gly Leu Ala Ala Leu Met Thr Leu Ser Val Ile Ala
    130                 135                 140

Phe Val Arg Cys Leu Ala Val Leu Arg Leu Gly Ser Phe Thr Gly Leu
145                 150                 155                 160

Thr Thr Arg Met Gly Val Ala Ala Met Ala Phe Ile Trp Ile Tyr Ser
                165                 170                 175

Leu Ala Phe Thr Leu Ala Pro Leu Leu Gly Trp Asn His Tyr Ile Pro
                180                 185                 190

Glu Gly Leu Ala Thr Trp Cys Ser Ile Asp Trp Leu Ser Asp Glu Thr
            195                 200                 205

Ser Asp Lys Ser Tyr Val Phe Ala Ile Phe Ile Phe Cys Phe Leu Val
        210                 215                 220

Pro Val Leu Ile Ile Val Val Ser Tyr Gly Leu Ile Tyr Asp Lys Val
225                 230                 235                 240

Arg Lys Val Ala Lys Thr Gly Gly Ser Val Ala Lys Ala Glu Arg Glu
                245                 250                 255

Val Leu Arg Met Thr Leu Leu Met Val Ser Leu Phe Met Leu Ala Trp
                260                 265                 270
```

```
Ser Pro Tyr Ala Val Ile Cys Met Leu Ala Ser Phe Gly Pro Lys Asp
        275                 280                 285

Leu Leu His Pro Val Ala Thr Val Ile Pro Ala Met Phe Ala Lys Ser
        290                 295                 300

Ser Thr Met Tyr Asn Pro Leu Ile Tyr Val Phe Met Asn Lys Gln Phe
305                 310                 315                 320

Arg Arg Ser Leu Lys Val Leu Leu Gly Met Gly Val Glu Asp Leu Asn
                325                 330                 335

Ser Glu Ser Glu Arg Ala Thr Gly Gly Thr Ala Thr Asn Gln Val Ala
            340                 345                 350

Ala Thr
```

```
<210> SEQ ID NO 26
<211> LENGTH: 1062
<212> TYPE: DNA
<213> ORGANISM: Artificial sequence
<220> FEATURE:
<223> OTHER INFORMATION: PdCO2 na sequence

<400> SEQUENCE: 26
atggacgggg agaacttgac gattccaaat cctgtcaccg agttgatgga taccccaatc      60
aacagcacgt atttccaaaa ccttaatgcg gaaacggacg gcggaaatca ttacatctac     120
aatgccttca cagccaccga ttacaacatt tgtgcagctt accttttctt cattgcttgt     180
ctgggagtca gtctcaacgt tttggtgttg gtcctcttta tcaaagacag aaagttgagg     240
agccccaata acttcctgta tgtaagtctc gctctcgggg atctgttggt tgcagttttc     300
ggcaccgcat ttaagttcat tattacagct cgcaaaaccc tgttgcgaga agaagacggt     360
ttctgcaaat ggtacggctt cataacatac ctcggcgggc tcgcggcact gatgaccctg     420
agcgttattg ctttttgttcg ttgtctggcc gtgctgcgtc tcggctcctt cacaggtttg     480
acaacgcgga tgggcgtggc ggcgatggct ttcatttgga tctactccct ggcattcaca     540
ctcgcgcctc tccttgggtg gaatcactac ataccggaag gtttggccac ttggtgtagt     600
atcgactggc tttccgatga aacatccgat aagtcctacg tgtttgctat tttcatcttc     660
tgctttcttg tccctgttct cattatcgtc gtgtcatacg gctgatcta cgataaggtt     720 cggaaggtag cgaaaacagg cggttctgtt gccaaagcag aacgcgaagt actgcgcatg     780
acgctgctga tggttagcct gttcatgctt gcctggagtc cctacgctgt tatctgcatg     840
ctcgctagct tcggccctaa agacctgctc catccagtgg ccacagtgat tcctgccatg     900
tttgcaaagt cttctacgat gtataaccct cttatctatg tgttcatgaa caaacaattc     960
aggcggagcc ttaaagttct tctcggaatg ggagtagagg acctgaactc cgagagtgag    1020
agagcaactg gtggtacagc cacgaatcaa gtcgccgcga cg                        1062
```

```
<210> SEQ ID NO 27
<211> LENGTH: 631
<212> TYPE: PRT
<213> ORGANISM: Artificial sequence
<220> FEATURE:
<223> OTHER INFORMATION: PdCO2-mScarlet open reading frame AA sequence

<400> SEQUENCE: 27

Met Asp Gly Glu Asn Leu Thr Ile Pro Asn Pro Val Thr Glu Leu Met
1               5                   10                  15

Asp Thr Pro Ile Asn Ser Thr Tyr Phe Gln Asn Leu Asn Ala Glu Thr
            20                  25                  30
```

-continued

```
Asp Gly Gly Asn His Tyr Ile Tyr Asn Ala Phe Thr Ala Thr Asp Tyr
        35                  40                  45

Asn Ile Cys Ala Ala Tyr Leu Phe Phe Ile Ala Cys Leu Gly Val Ser
        50                  55                  60

Leu Asn Val Leu Val Leu Val Leu Phe Ile Lys Asp Arg Lys Leu Arg
65                  70                  75                  80

Ser Pro Asn Asn Phe Leu Tyr Val Ser Leu Ala Leu Gly Asp Leu Leu
                    85                  90                  95

Val Ala Val Phe Gly Thr Ala Phe Lys Phe Ile Ile Thr Ala Arg Lys
                100                 105                 110

Thr Leu Leu Arg Glu Glu Asp Gly Phe Cys Lys Trp Tyr Gly Phe Ile
            115                 120                 125

Thr Tyr Leu Gly Gly Leu Ala Ala Leu Met Thr Leu Ser Val Ile Ala
        130                 135                 140

Phe Val Arg Cys Leu Ala Val Leu Arg Leu Gly Ser Phe Thr Gly Leu
145                 150                 155                 160

Thr Thr Arg Met Gly Val Ala Ala Met Ala Phe Ile Trp Ile Tyr Ser
                165                 170                 175

Leu Ala Phe Thr Leu Ala Pro Leu Leu Gly Trp Asn His Tyr Ile Pro
                180                 185                 190

Glu Gly Leu Ala Thr Trp Cys Ser Ile Asp Trp Leu Ser Asp Glu Thr
            195                 200                 205

Ser Asp Lys Ser Tyr Val Phe Ala Ile Phe Ile Phe Cys Phe Leu Val
        210                 215                 220

Pro Val Leu Ile Ile Val Val Ser Tyr Gly Leu Ile Tyr Asp Lys Val
225                 230                 235                 240

Arg Lys Val Ala Lys Thr Gly Gly Ser Val Ala Lys Ala Glu Arg Glu
                245                 250                 255

Val Leu Arg Met Thr Leu Leu Met Val Ser Leu Phe Met Leu Ala Trp
                260                 265                 270

Ser Pro Tyr Ala Val Ile Cys Met Leu Ala Ser Phe Gly Pro Lys Asp
            275                 280                 285

Leu Leu His Pro Val Ala Thr Val Ile Pro Ala Met Phe Ala Lys Ser
        290                 295                 300

Ser Thr Met Tyr Asn Pro Leu Ile Tyr Val Phe Met Asn Lys Gln Phe
305                 310                 315                 320

Arg Arg Ser Leu Lys Val Leu Leu Gly Met Gly Val Glu Asp Leu Asn
                325                 330                 335

Ser Glu Ser Glu Arg Ala Thr Gly Gly Thr Ala Thr Asn Gln Val Ala
            340                 345                 350

Ala Thr Thr Glu Thr Ser Gln Val Ala Pro Ala Pro Arg Ala Arg Asp
            355                 360                 365

Pro Thr Gly Lys Ser Arg Ile Thr Ser Glu Gly Glu Tyr Ile Pro Leu
        370                 375                 380

Asp Gln Ile Asp Ile Asn Val Val Met Val Ser Lys Gly Glu Ala Val
385                 390                 395                 400

Ile Lys Glu Phe Met Arg Phe Lys Val His Met Glu Gly Ser Met Asn
                405                 410                 415

Gly His Glu Phe Glu Ile Glu Gly Glu Gly Glu Gly Arg Pro Tyr Glu
                420                 425                 430

Gly Thr Gln Thr Ala Lys Leu Lys Val Thr Lys Gly Gly Pro Leu Pro
            435                 440                 445

Phe Ser Trp Asp Ile Leu Ser Pro Gln Phe Met Tyr Gly Ser Arg Ala
```

-continued

```
        450               455               460

Phe Thr Lys His Pro Ala Asp Ile Pro Asp Tyr Tyr Lys Gln Ser Phe
465               470               475               480

Pro Glu Gly Phe Lys Trp Glu Arg Val Met Asn Phe Glu Asp Gly Gly
                  485               490               495

Ala Val Thr Val Thr Gln Asp Thr Ser Leu Glu Asp Gly Thr Leu Ile
                  500               505               510

Tyr Lys Val Lys Leu Arg Gly Thr Asn Phe Pro Pro Asp Gly Pro Val
                  515               520               525

Met Gln Lys Lys Thr Met Gly Trp Glu Ala Ser Thr Glu Arg Leu Tyr
                  530               535               540

Pro Glu Asp Gly Val Leu Lys Gly Asp Ile Lys Met Ala Leu Arg Leu
545               550               555               560

Lys Asp Gly Gly Arg Tyr Leu Ala Asp Phe Lys Thr Thr Tyr Lys Ala
                  565               570               575

Lys Lys Pro Val Gln Met Pro Gly Ala Tyr Asn Val Asp Arg Lys Leu
                  580               585               590

Asp Ile Thr Ser His Asn Glu Asp Tyr Thr Val Val Glu Gln Tyr Glu
                  595               600               605

Arg Ser Glu Gly Arg His Ser Thr Gly Gly Met Asp Glu Leu Tyr Lys
                  610               615               620

Phe Cys Tyr Glu Asn Glu Val
625               630
```

```
<210> SEQ ID NO 28
<211> LENGTH: 1900
<212> TYPE: DNA
<213> ORGANISM: Artificial sequence
<220> FEATURE:
<223> OTHER INFORMATION: PdCO2-mScarlet open reading frame NA sequence

<400> SEQUENCE: 28
atggacgggg agaacttgac gattccaaat cctgtcaccg agttgatgga taccccaatc        60
aacagcacgt atttccaaaa ccttaatgcg gaaacggacg gcggaaatca ttacatctac       120
aatgccttca cagccaccga ttacaacatt tgtgcagctt accttttctt cattgcttgt       180
ctgggagtca gtctcaacgt tttggtgttg gtcctctta tcaaagacag aaagttgagg        240
agccccaata acttcctgta tgtaagtctc gctctcgggg atctgttggt tgcagttttc       300
ggcaccgcat ttaagttcat tattacagct cgcaaaaccc tgttgcgaga agaagacggt       360
ttctgcaaat ggtacggctt cataacatac ctcggcgggc tcgcggcact gatgaccctg       420
agcgttattg cttttgttcg ttgtctggcc gtgctgcgtc tcggctcctt cacaggtttg       480
acaacgcgga tgggcgtggc ggcgatggct ttcatttgga tctactccct ggcattcaca       540
ctcgcgcctc tccttgggtg gaatcactac ataccggaag gtttggccac ttggtgtagt       600
atcgactggc tttccgatga acatccgat aagtcctacg tgtttgctat tttcatcttc        660
tgctttcttg tccctgttct cattatcgtc gtgtcatacg ggctgatcta cgataaggtt       720
cggaaggtag cgaaaacagg cggttctgtt gccaaagcag aacgcgaagt actgcgcatg       780
acgctgctga tggttagcct gttcatgctt gcctggagtc cctacgctgt tatctgcatg       840
ctcgctagct tcggccctaa agacctgctc catccagtgg ccacagtgat tcctgccatg       900
tttgcaaagt cttctacgat gtataaccct cttatctatg tgttcatgaa caaacaattc       960
aggcggagcc ttaaagttct tctcggaatg ggagtagagg acctgaactc cgagagtgag      1020
```

```
agagcaactg gtggtacagc cacgaatcaa gtcgccgcga cgaccgagac ttcccaggtt   1080
gctcctgctc cgcgagcccg agatccaacc ggtaagagca ggatcaccag cgagggcgag   1140
tacatccccc tggaccagat cgacatcaac gtggtgatgg tgagcaaggg cgaggcagtg   1200
atcaaggagt tcatgcggtt caaggtgcac atggagggct ccatgaacgg ccacgagttc   1260
gagatcgagg gcgagggcga gggccgcccc tacgagggca cccagaccgc caagctgaag   1320
gtgaccaagg gtggcccct gcccttctcc tgggacatcc tgtcccctca gttcatgtac   1380
ggctccaggg ccttcaccaa gcaccccgcc gacatcccg actactataa gcagtccttc   1440
cccgagggct tcaagtggga gcgcgtgatg aacttcgagg acggcggcgc cgtgaccgtg   1500
acccaggaca cctccctgga ggacggcacc ctgatctaca aggtgaagct ccgcggcacc   1560
aacttccctc ctgacggccc cgtaatgcag aagaagacaa tgggctggga agcgtccacc   1620
gagcggttgt acccgagga cggcgtgctg aagggcgaca ttaagatggc cctgcgcctg   1680
aaggacggcg gacgctacct ggcggacttc aagaccacct acaaggccaa gaagcccgtg   1740
cagatgcccg gcgcctacaa cgtcgaccgc aagttggaca tcacctccca caacgaggac   1800
tacaccgtgg tggaacagta cgaacgctcc gagggccgcc actccaccgg cggcatggac   1860
gagctgtaca agttctgcta cgagaacgag gtgtaactag                           1900
```

```
<210> SEQ ID NO 29
<211> LENGTH: 343
<212> TYPE: PRT
<213> ORGANISM: Artificial sequence
<220> FEATURE:
<223> OTHER INFORMATION: LcPP aa sequence

<400> SEQUENCE: 29

Met Glu Asn Leu Thr Ser Leu Asp Leu Leu Pro Asn Gly Glu Val Pro
1               5                   10                  15

Leu Met Pro Arg Tyr Gly Phe Thr Ile Leu Ala Val Ile Met Ala Val
            20                  25                  30

Phe Thr Ile Ala Ser Leu Val Leu Asn Ser Thr Val Val Ile Val Thr
        35                  40                  45

Leu Arg His Arg Gln Leu Arg His Pro Leu Asn Phe Ser Leu Val Asn
    50                  55                  60

Leu Ala Val Ala Asp Leu Gly Val Thr Val Phe Gly Ala Ser Leu Val
65                  70                  75                  80

Val Glu Thr Asn Ala Val Gly Tyr Phe Asn Leu Gly Arg Val Gly Cys
                85                  90                  95

Val Ile Glu Gly Phe Ala Val Ala Phe Phe Gly Ile Ala Ala Leu Cys
            100                 105                 110

Thr Ile Ala Val Ile Ala Val Asp Arg Phe Val Val Cys Lys Pro
        115                 120                 125

Leu Gly Thr Leu Met Phe Thr Arg Arg His Ala Leu Leu Gly Ile Ala
    130                 135                 140

Trp Ala Trp Leu Trp Ser Phe Val Trp Asn Thr Pro Pro Leu Phe Gly
145                 150                 155                 160

Trp Gly Ser Tyr Glu Leu Glu Gly Val Arg Thr Ser Cys Ala Pro Asp
                165                 170                 175

Trp Tyr Ser Arg Asp Pro Ala Asn Val Ser Tyr Ile Thr Ser Tyr Phe
            180                 185                 190

Ala Phe Cys Phe Ala Ile Pro Phe Leu Val Ile Val Val Ala Tyr Gly
        195                 200                 205
```

-continued

Arg Leu Met Trp Thr Leu His Gln Val Ala Lys Leu Gly Met Gly Glu
    210                 215                 220

Ser Gly Ser Thr Ala Lys Ala Glu Ala Gln Val Ser Arg Met Val Val
225                 230                 235                 240

Val Met Val Val Ala Phe Leu Val Cys Trp Leu Pro Tyr Ala Leu Phe
                245                 250                 255

Ala Met Ile Val Val Thr Lys Pro Asp Val Tyr Ile Asp Pro Val Ile
            260                 265                 270

Ala Thr Leu Pro Met Tyr Leu Thr Lys Thr Ser Thr Val Tyr Asn Pro
        275                 280                 285

Ile Ile Tyr Ile Phe Met Asn Arg Gln Phe Arg Asp Cys Ala Val Pro
    290                 295                 300

Phe Leu Leu Cys Gly Arg Asn Pro Trp Ala Glu Pro Ser Ser Glu Ser
305                 310                 315                 320

Ala Thr Ala Ala Ser Thr Ser Ala Thr Ser Val Thr Leu Ala Ser Ala
                325                 330                 335

Pro Gly Gln Val Ser Pro Ser
            340

<210> SEQ ID NO 30
<211> LENGTH: 1029
<212> TYPE: DNA
<213> ORGANISM: Artificial sequence
<220> FEATURE:
<223> OTHER INFORMATION: LcPP na sequence

<400> SEQUENCE: 30
atggaaaatc tgacttccct ggatctgctg cccaacggag aggtcccact gatgccccgg        60
tacggcttta ctattctggc tgtgattatg gccgtgttca ccatcgcaag tctggtcctg       120
aactcaactg tggtcattgt gaccctgcga caccgacagc tgaggcatcc tctgaacttt       180
tccctggtga atctggctgt cgcagacctg ggcgtgacag tcttcggagc ttctctggtg       240
gtcgagacta acgcagtggg gtactttaat ctgggacgcg tggggtgcgt catcgaaggg       300
ttcgccgtgg ctttctttgg cattgccgct ctgtgcacca tcgctgtgat tgcagtcgat       360
cgatttgtgg tggtgtgcaa gcccctggga accctgatgt tcacaaggag acacgcactg       420
ctgggaatcg catgggcatg gctgtggagc ttcgtgtgga acacacccc tctgttcggc        480 tggggaagct acgagctgga aggagtgaga actagctgcg ctcctgactg gtattcccgg       540
gaccccgcca acgtgagcta catcacatct tatttcgcat tttgtttcgc catcccttc        600 ctggtcatcg tcgtggctta cggccggctg atgtggactc tgcatcaggt ggccaagctg       660
gggatgggcg agtctggaag taccgctaaa gcagaagccc aggtgagtcg catggtcgtg       720
gtcatggtgt tcgcctttct ggtctgttgg ctgccctatg ccctgttcgc tatgatcgtg       780
gtcaccaagc ctgacgtgta catcgatcca gtcattgcca cactgcccat gtatctgacc       840
aaaacaagca ccgtgtacaa ccccatcatc tacatcttca tgaatcgaca gttcagggac       900
tgcgccgtgc ctttcctgct gtgcggcagg aatccctggg cagagcccag ctccgaatct       960
gccacagcag cctcaaccag cgccacaagt gtgactctgg cttcagcacc aggacaggtc      1020
tccccatcc                                                              1029

<210> SEQ ID NO 31
<211> LENGTH: 620
<212> TYPE: PRT
<213> ORGANISM: Artificial sequence
<220> FEATURE:

<223> OTHER INFORMATION: LcPP -mScarlet open reading frame AA sequence

<400> SEQUENCE: 31

```
Met Glu Asn Leu Thr Ser Leu Asp Leu Leu Pro Asn Gly Glu Val Pro
1               5                   10                  15

Leu Met Pro Arg Tyr Gly Phe Thr Ile Leu Ala Val Ile Met Ala Val
            20                  25                  30

Phe Thr Ile Ala Ser Leu Val Leu Asn Ser Thr Val Val Ile Val Thr
            35                  40                  45

Leu Arg His Arg Gln Leu Arg His Pro Leu Asn Phe Ser Leu Val Asn
        50                  55                  60

Leu Ala Val Ala Asp Leu Gly Val Thr Val Phe Gly Ala Ser Leu Val
65                  70                  75                  80

Val Glu Thr Asn Ala Val Gly Tyr Phe Asn Leu Gly Arg Val Gly Cys
                85                  90                  95

Val Ile Glu Gly Phe Ala Val Ala Phe Phe Gly Ile Ala Ala Leu Cys
            100                 105                 110

Thr Ile Ala Val Ile Ala Val Asp Arg Phe Val Val Val Cys Lys Pro
            115                 120                 125

Leu Gly Thr Leu Met Phe Thr Arg Arg His Ala Leu Leu Gly Ile Ala
        130                 135                 140

Trp Ala Trp Leu Trp Ser Phe Val Trp Asn Thr Pro Pro Leu Phe Gly
145                 150                 155                 160

Trp Gly Ser Tyr Glu Leu Glu Gly Val Arg Thr Ser Cys Ala Pro Asp
                165                 170                 175

Trp Tyr Ser Arg Asp Pro Ala Asn Val Ser Tyr Ile Thr Ser Tyr Phe
            180                 185                 190

Ala Phe Cys Phe Ala Ile Pro Phe Leu Val Ile Val Val Ala Tyr Gly
            195                 200                 205

Arg Leu Met Trp Thr Leu His Gln Val Ala Lys Leu Gly Met Gly Glu
        210                 215                 220

Ser Gly Ser Thr Ala Lys Ala Glu Ala Gln Val Ser Arg Met Val Val
225                 230                 235                 240

Val Met Val Val Ala Phe Leu Val Cys Trp Leu Pro Tyr Ala Leu Phe
                245                 250                 255

Ala Met Ile Val Val Thr Lys Pro Asp Val Tyr Ile Asp Pro Val Ile
            260                 265                 270

Ala Thr Leu Pro Met Tyr Leu Thr Lys Thr Ser Thr Val Tyr Asn Pro
            275                 280                 285

Ile Ile Tyr Ile Phe Met Asn Arg Gln Phe Arg Asp Cys Ala Val Pro
        290                 295                 300

Phe Leu Leu Cys Gly Arg Asn Pro Trp Ala Glu Pro Ser Ser Glu Ser
305                 310                 315                 320

Ala Thr Ala Ala Ser Thr Ser Ala Thr Ser Val Thr Leu Ala Ser Ala
                325                 330                 335

Pro Gly Gln Val Ser Pro Ser Thr Glu Thr Ser Gln Val Ala Pro Ala
            340                 345                 350

Pro Arg Ala Arg Asp Pro Thr Gly Lys Ser Arg Ile Thr Ser Glu Gly
            355                 360                 365

Glu Tyr Ile Pro Leu Asp Gln Ile Asp Ile Asn Val Val Met Val Ser
        370                 375                 380

Lys Gly Glu Ala Val Ile Lys Glu Phe Met Arg Phe Lys Val His Met
385                 390                 395                 400
```

-continued

_____

```
Glu Gly Ser Met Asn Gly His Glu Phe Glu Ile Glu Gly Glu Gly Glu
                405                 410                 415

Gly Arg Pro Tyr Glu Gly Thr Gln Thr Ala Lys Leu Lys Val Thr Lys
                420                 425                 430

Gly Gly Pro Leu Pro Phe Ser Trp Asp Ile Leu Ser Pro Gln Phe Met
            435                 440                 445

Tyr Gly Ser Arg Ala Phe Thr Lys His Pro Ala Asp Ile Pro Asp Tyr
    450                 455                 460

Tyr Lys Gln Ser Phe Pro Glu Gly Phe Lys Trp Glu Arg Val Met Asn
465                 470                 475                 480

Phe Glu Asp Gly Gly Ala Val Thr Val Thr Gln Asp Thr Ser Leu Glu
                485                 490                 495

Asp Gly Thr Leu Ile Tyr Lys Val Lys Leu Arg Gly Thr Asn Phe Pro
            500                 505                 510

Pro Asp Gly Pro Val Met Gln Lys Lys Thr Met Gly Trp Glu Ala Ser
            515                 520                 525

Thr Glu Arg Leu Tyr Pro Glu Asp Gly Val Leu Lys Gly Asp Ile Lys
            530                 535                 540

Met Ala Leu Arg Leu Lys Asp Gly Gly Arg Tyr Leu Ala Asp Phe Lys
545                 550                 555                 560

Thr Thr Tyr Lys Ala Lys Lys Pro Val Gln Met Pro Gly Ala Tyr Asn
                565                 570                 575

Val Asp Arg Lys Leu Asp Ile Thr Ser His Asn Glu Asp Tyr Thr Val
                580                 585                 590

Val Glu Gln Tyr Glu Arg Ser Glu Gly Arg His Ser Thr Gly Gly Met
            595                 600                 605

Asp Glu Leu Tyr Lys Phe Cys Tyr Glu Asn Glu Val
    610                 615                 620
```

<210> SEQ ID NO 32
<211> LENGTH: 1863
<212> TYPE: DNA
<213> ORGANISM: Artificial sequence
<220> FEATURE:
<223> OTHER INFORMATION: LcPP -mScarlet open reading frame NA sequence

<400> SEQUENCE: 32

```
atggaaaatc tgacttccct ggatctgctg cccaacggag aggtcccact gatgccccgg     60
tacggcttta ctattctggc tgtgattatg gccgtgttca ccatcgcaag tctggtcctg    120
aactcaactg tggtcattgt gaccctgcga caccgacagc tgaggcatcc tctgaacttt    180
tccctggtga atctggctgt cgcagacctg ggcgtgacag tcttcggagc ttctctggtg    240
gtcgagacta acgcagtggg gtactttaat ctgggacgcg tggggtgcgt catcgaaggg    300
ttcgccgtgg ctttctttgg cattgccgct ctgtgcacca tcgctgtgat tgcagtcgat    360
cgatttgtgg tggtgtgcaa gcccctggga accctgatgt tcacaaggag acacgcactg    420
ctgggaatcg catgggcatg gctgtggagc ttcgtgtgga acacacccccc tctgttcggc    480 tggggaagct acgagctgga aggagtgaga actagctgcg ctcctgactg gtattcccgg    540
gaccccgcca acgtgagcta catcacatct tatttcgcat tttgtttcgc catcccttc    600 ctggtcatcg tcgtggctta cggccggctg atgtggactc tgcatcaggt ggccaagctg    660
gggatgggcg agtctggaag taccgctaaa gcagaagccc aggtgagtcg catggtcgtg    720
gtcatggtgt cgcctttct ggtctgttgg ctgccctatg ccctgttcgc tatgatcgtg    780
gtcaccaagc tgacgtgta catcgatcca gtcattgcca cactgcccat gtatctgacc    840
```

-continued

```
aaaacaagca ccgtgtacaa ccccatcatc tacatcttca tgaatcgaca gttcagggac    900
tgcgccgtgc ctttcctgct gtgcggcagg aatccctggg cagagcccag ctccgaatct    960
gccacagcag cctcaaccag cgccacaagt gtgactctgg cttcagcacc aggacaggtc   1020
tccccatcca ccgagaccag ccaggtggct cctgctccgc gagcccgaga tccaaccggt   1080
aagagcagga tcaccagcga gggcgagtac atcccctgg accagatcga catcaacgtg   1140
gtgatggtga gcaagggcga ggcagtgatc aaggagttca tgcggttcaa ggtgcacatg   1200
gagggctcca tgaacggcca cgagttcgag atcgagggcg agggcgaggg ccgcccctac   1260
gagggcaccc agaccgccaa gctgaaggtg accaagggtg gcccctgcc cttctcctgg   1320 gacatcctgt cccctcagtt catgtacggc tccagggcct tcaccaagca ccccgccgac   1380
atccccgact actataagca gtccttcccc gagggcttca gtgggagcg cgtgatgaac   1440 ttcgaggacg gcggcgccgt gaccgtgacc caggacacct ccctggagga cggcaccctg   1500
atctacaagg tgaagctccg cggcaccaac ttccctcctg acggccccgt aatgcagaag   1560
aagacaatgg gctgggaagc gtccaccgag cggttgtacc ccgaggacgg cgtgctgaag   1620
ggcgacatta agatggccct cgcgcctgaag acggcggac gctacctggc ggacttcaag   1680
accacctaca aggccaagaa gcccgtgcag atgcccggcg cctacaacgt cgaccgcaag   1740
ttggacatca cctcccacaa cgaggactac accgtggtgg aacagtacga acgctccgag   1800
ggccgccact ccaccggcgg catggacgag ctgtacaagt ctgctacga gaacgaggtg   1860 taa                                                                 1863
```

```
<210> SEQ ID NO 33
<211> LENGTH: 342
<212> TYPE: PRT
<213> ORGANISM: Artificial sequence
<220> FEATURE:
<223> OTHER INFORMATION: medakaTMT1A aa sequence

<400> SEQUENCE: 33

Met Leu Val Ser Asn Val Ser Leu Gly Gly Cys Ala Glu Phe Asn Ser
1               5                   10                  15

Ala Leu Cys Ala Gly Ala Gly Glu Glu His Leu Gly Gly Gly Ser Tyr
                20                  25                  30

Arg Thr Thr Leu Thr Pro Thr Gly His Leu Ile Val Ala Val Cys Leu
            35                  40                  45

Gly Phe Ile Gly Thr Phe Gly Leu Val Asn Asn Leu Leu Val Leu Val
        50                  55                  60

Leu Phe Cys Arg Tyr Lys Ile Leu Arg Ser Pro Ile Asn Leu Leu Leu
65                  70                  75                  80

Ile Asn Ile Ser Ile Ser Asp Leu Leu Val Cys Val Leu Gly Thr Pro
                85                  90                  95

Phe Ser Phe Ala Ala Ser Thr Gln Gly Arg Trp Leu Ile Gly Glu Gly
            100                 105                 110

Gly Cys Val Trp Tyr Gly Phe Ala Asn Ser Leu Cys Gly Ile Val Ser
        115                 120                 125

Leu Ile Ser Leu Ala Val Leu Ser Tyr Glu Arg Tyr Ser Thr Met Met
    130                 135                 140

Thr Pro Ala Glu Ala Asp Ser Ser Asn Tyr Arg Lys Ile Ser Leu Gly
145                 150                 155                 160

Ile Ile Leu Ser Trp Gly Tyr Ser Leu Leu Trp Thr Leu Pro Pro Leu
                165                 170                 175
```

```
Phe Gly Trp Ser His Tyr Gly Pro Glu Gly Pro Gly Thr Thr Cys Ser
            180                 185                 190

Val Asp Trp Thr Ala Lys Thr Ala Asn Asn Ile Ser Tyr Ile Ile Cys
        195                 200                 205

Leu Phe Val Phe Cys Leu Ile Val Pro Phe Met Val Ile Val Phe Cys
    210                 215                 220

Tyr Gly Lys Leu Leu Tyr Ala Ile Lys Gln Val Ser Gly Ile Asn Val
225                 230                 235                 240

Ser Val Ser Arg Lys Arg Glu Gln Arg Val Leu Phe Met Val Val Ile
                245                 250                 255

Met Val Ile Cys Tyr Leu Leu Cys Trp Leu Pro Tyr Gly Ile Met Ala
                260                 265                 270

Leu Leu Ala Thr Phe Gly Pro Pro Asp Leu Val Thr Pro Glu Ala Ser
            275                 280                 285

Ile Ile Pro Ser Val Leu Ala Lys Thr Ser Thr Ala Ile Asn Pro Val
        290                 295                 300

Ile Tyr Val Phe Met Asn Lys Gln Phe Phe Arg Cys Phe Gln Ala Met
305                 310                 315                 320

Leu Arg Cys Lys Ala Pro Leu Arg Gly Ser Ser Ala Arg Ser Ser Ser
                325                 330                 335

Lys Val Ala Thr Lys Ala
            340

<210> SEQ ID NO 34
<211> LENGTH: 1026
<212> TYPE: DNA
<213> ORGANISM: Artificial sequence
<220> FEATURE:
<223> OTHER INFORMATION: medakaTMT1A na sequence

<400> SEQUENCE: 34
atgctagtca gtaatgtaag cctgggtggg tgcgccgaat tcaattccgc tctttgtgcg      60
ggcgctggag aagaacacct cggcggtggt tcatatcgga ccacgctaac cccgactggc     120
catctcattg tcgctgtgtg ccttgggttc attggcactt tcgggcttgt aaataatttg     180
cttgtcttgg tcctattctg tcgttataag attctgcgga gccctatcaa tcttctactt     240
attaatatca gtatttccga cctgctcgtt tgcgtgctgg caccccttt ctcctttgct     300 gctagtacac aaggcaggtg gttgattggc gagggcggat gtgtatggta cggatttgcg     360
aacagcctgt gtgggatcgt tagcctaatt cccttgctg tcctttctta tgaacgttac     420
tctactatga tgacccccgc ggaagccgac tcaagtaatt accggaaaat aagtctcggt     480
atcatcctct cctggggcta tagtttgctc tggacgttgc cccctttgtt tggctggagt     540
cattacgggc ccgaaggacc aggaaccacc tgtagcgtcg attggaccgc caagaccgcc     600
aataacatta ctatattat ctgcctgttt gtgttctgtc ttatcgtgcc gtttatggtg     660
attgtatttt gctatggtaa actgctgtac gctattaaac aagtgagcgg aattaatgtc     720
agtgtaagta ggaaacgaga acaacgcgtg ctctttatgg tggtcattat ggtcatatgc     780
tacctgcttt gttggctccc ttacggcatt atggcccttc tcgcaacgtt tggacccccca     840 gacctcgtca ccccagaagc tctctcatca ccctcagttc tcgcgaagac tagtaccgct     900
ataaatccag ttatctatgt ctttatgaat aagcagttct tcaggtgttt ccaagcaatg     960
cttaggtgta agctccact gcgcgggagc tcagcaaggt ccagctccaa agttgctaca    1020
aaagct                                                              1026
```

-continued

<210> SEQ ID NO 35
<211> LENGTH: 619
<212> TYPE: PRT
<213> ORGANISM: Artificial sequence
<220> FEATURE:
<223> OTHER INFORMATION: medakaTMT1A -mScarlet open reading frame AA
     sequence

<400> SEQUENCE: 35

Met Leu Val Ser Asn Val Ser Leu Gly Gly Cys Ala Glu Phe Asn Ser
1               5                   10                  15

Ala Leu Cys Ala Gly Ala Gly Glu Glu His Leu Gly Gly Gly Ser Tyr
            20                  25                  30

Arg Thr Thr Leu Thr Pro Thr Gly His Leu Ile Val Ala Val Cys Leu
        35                  40                  45

Gly Phe Ile Gly Thr Phe Gly Leu Val Asn Asn Leu Leu Val Leu Val
        50                  55                  60

Leu Phe Cys Arg Tyr Lys Ile Leu Arg Ser Pro Ile Asn Leu Leu Leu
65                  70                  75                  80

Ile Asn Ile Ser Ile Ser Asp Leu Leu Val Cys Val Leu Gly Thr Pro
                85                  90                  95

Phe Ser Phe Ala Ala Ser Thr Gln Gly Arg Trp Leu Ile Gly Glu Gly
            100                 105                 110

Gly Cys Val Trp Tyr Gly Phe Ala Asn Ser Leu Cys Gly Ile Val Ser
            115                 120                 125

Leu Ile Ser Leu Ala Val Leu Ser Tyr Glu Arg Tyr Ser Thr Met Met
        130                 135                 140

Thr Pro Ala Glu Ala Asp Ser Ser Asn Tyr Arg Lys Ile Ser Leu Gly
145                 150                 155                 160

Ile Ile Leu Ser Trp Gly Tyr Ser Leu Leu Trp Thr Leu Pro Pro Leu
                165                 170                 175

Phe Gly Trp Ser His Tyr Gly Pro Glu Gly Pro Gly Thr Thr Cys Ser
            180                 185                 190

Val Asp Trp Thr Ala Lys Thr Ala Asn Asn Ile Ser Tyr Ile Ile Cys
            195                 200                 205

Leu Phe Val Phe Cys Leu Ile Val Pro Phe Met Val Ile Val Phe Cys
        210                 215                 220

Tyr Gly Lys Leu Leu Tyr Ala Ile Lys Gln Val Ser Gly Ile Asn Val
225                 230                 235                 240

Ser Val Ser Arg Lys Arg Glu Gln Arg Val Leu Phe Met Val Val Ile
                245                 250                 255

Met Val Ile Cys Tyr Leu Leu Cys Trp Leu Pro Tyr Gly Ile Met Ala
            260                 265                 270

Leu Leu Ala Thr Phe Gly Pro Pro Asp Leu Val Thr Pro Glu Ala Ser
        275                 280                 285

Ile Ile Pro Ser Val Leu Ala Lys Thr Ser Thr Ala Ile Asn Pro Val
        290                 295                 300

Ile Tyr Val Phe Met Asn Lys Gln Phe Phe Arg Cys Phe Gln Ala Met
305                 310                 315                 320

Leu Arg Cys Lys Ala Pro Leu Arg Gly Ser Ser Ala Arg Ser Ser Ser
                325                 330                 335

Lys Val Ala Thr Lys Ala Thr Glu Thr Ser Gln Val Ala Pro Ala Pro
            340                 345                 350

Arg Ala Arg Asp Pro Thr Gly Lys Ser Arg Ile Thr Ser Glu Gly Glu

-continued

```
                355               360               365
Tyr Ile Pro Leu Asp Gln Ile Asp Ile Asn Val Val Met Val Ser Lys
    370               375               380
Gly Glu Ala Val Ile Lys Glu Phe Met Arg Phe Lys Val His Met Glu
385               390               395               400
Gly Ser Met Asn Gly His Glu Phe Glu Ile Glu Gly Glu Gly Glu Gly
                405               410               415
Arg Pro Tyr Glu Gly Thr Gln Thr Ala Lys Leu Lys Val Thr Lys Gly
            420               425               430
Gly Pro Leu Pro Phe Ser Trp Asp Ile Leu Ser Pro Gln Phe Met Tyr
        435               440               445
Gly Ser Arg Ala Phe Thr Lys His Pro Ala Asp Ile Pro Asp Tyr Tyr
    450               455               460
Lys Gln Ser Phe Pro Glu Gly Phe Lys Trp Glu Arg Val Met Asn Phe
465               470               475               480
Glu Asp Gly Gly Ala Val Thr Val Thr Gln Asp Thr Ser Leu Glu Asp
                485               490               495
Gly Thr Leu Ile Tyr Lys Val Lys Leu Arg Gly Thr Asn Phe Pro Pro
            500               505               510
Asp Gly Pro Val Met Gln Lys Lys Thr Met Gly Trp Glu Ala Ser Thr
        515               520               525
Glu Arg Leu Tyr Pro Glu Asp Gly Val Leu Lys Gly Asp Ile Lys Met
    530               535               540
Ala Leu Arg Leu Lys Asp Gly Gly Arg Tyr Leu Ala Asp Phe Lys Thr
545               550               555               560
Thr Tyr Lys Ala Lys Lys Pro Val Gln Met Pro Gly Ala Tyr Asn Val
                565               570               575
Asp Arg Lys Leu Asp Ile Thr Ser His Asn Glu Asp Tyr Thr Val Val
            580               585               590
Glu Gln Tyr Glu Arg Ser Glu Gly Arg His Ser Thr Gly Gly Met Asp
        595               600               605
Glu Leu Tyr Lys Phe Cys Tyr Glu Asn Glu Val
    610               615
```

```
<210> SEQ ID NO 36
<211> LENGTH: 1860
<212> TYPE: DNA
<213> ORGANISM: Artificial sequence
<220> FEATURE:
<223> OTHER INFORMATION: medakaTMT1A -mScarlet open reading frame NA
      sequence

<400> SEQUENCE: 36
atgctagtca gtaatgtaag cctgggtggg tgcgccgaat tcaattccgc tctttgtgcg      60
ggcgctggag aagaacacct cggcggtggt tcatatcgga ccacgctaac cccgactggc     120
catctcattg tcgctgtgtg ccttgggttc attggcactt tcgggcttgt aaataatttg     180
cttgtcttgg tcctattctg tcgttataag attctgcgga gccctatcaa tcttctactt     240
attaatatca gtatttccga cctgctcgtt tgcgtgctgg gcaccccttt ctcctttgct     300
gctagtacac aaggcaggtg gttgattggc gagggcggat gtgtatggta cggatttgcg     360
aacagcctgt gtgggatcgt tagcctaatt tcccttgctg tcctttctta tgaacgttac     420
tctactatga tgaccccgc ggaagccgac tcaagtaatt accggaaat aagtctcggt     480 atcatcctct cctggggcta tagtttgctc tggacgttgc cccctttgtt tggctggagt     540
```

```
cattacgggc ccgaaggacc aggaaccacc tgtagcgtcg attggaccgc caagaccgcc      600
aataacatta gctatattat ctgcctgttt gtgttctgtc ttatcgtgcc gtttatggtg      660
attgtatttt gctatggtaa actgctgtac gctattaaac aagtgagcgg aattaatgtc      720
agtgtaagta ggaaacgaga acaacgcgtg ctctttatgg tggtcattat ggtcatatgc      780
tacctgcttt gttggctccc ttacggcatt atggcccttc tcgcaacgtt tggaccccca      840
gacctcgtca ccccagaagc ctctatcata ccctcagttc tcgcgaagac tagtaccgct      900
ataaatccag ttatctatgt ctttatgaat aagcagttct tcaggtgttt ccaagcaatg      960
cttaggtgta aagctccact gcgcgggagc tcagcaaggt ccagctccaa agttgctaca     1020
aaagctacag agacaagcca agtggcgcct gctccgcgag cccgagatcc aaccggtaag     1080
agcaggatca ccagcgaggg cgagtacatc cccctggacc agatcgacat caacgtggtg     1140
atggtgagca agggcgaggc agtgatcaag gagttcatgc ggttcaaggt gcacatggag     1200
ggctccatga acggccacga gttcgagatc gagggcgagg gcgagggccg cccctacgag     1260
ggcacccaga ccgccaagct gaaggtgacc aagggtggcc ccctgccctt ctcctgggac     1320
atcctgtccc ctcagttcat gtacggctcc agggccttca ccaagcaccc cgccgacatc     1380
cccgactact ataagcagtc cttccccgag ggcttcaagt gggagcgcgt gatgaacttc     1440
gaggacggcg gcgccgtgac cgtgacccag gacacctccc tggaggacgg caccctgatc     1500
tacaaggtga agctccgcgg caccaacttc cctcctgacg gccccgtaat gcagaagaag     1560
acaatgggct gggaagcgtc caccgagcgg ttgtaccccg aggacggcgt gctgaagggc     1620
gacattaaga tggccctgcg cctgaaggac ggcggacgct acctggcgga cttcaagacc     1680
acctacaagg ccaagaagcc cgtgcagatg cccggcgcct acaacgtcga ccgcaagttg     1740
gacatcacct cccacaacga ggactacacc gtggtggaac agtacgaacg ctccgagggc     1800
cgccactcca ccggcggcat ggacgagctg tacaagttct gctacgagaa cgaggtgtaa     1860
```

```
<210> SEQ ID NO 37
<211> LENGTH: 341
<212> TYPE: PRT
<213> ORGANISM: Artificial sequence
<220> FEATURE:
<223> OTHER INFORMATION: zPP1 aa sequence

<400> SEQUENCE: 37

Met His Glu Glu Met Glu Ser Glu Thr Ser Thr Ala Ala Ser Gly Ser
1               5                   10                  15

Ile Ala Glu Val Met Pro Arg Thr Gly Tyr Thr Ile Leu Ala Val Ile
            20                  25                  30

Ile Gly Val Phe Ser Val Cys Gly Val Ile Leu Asn Val Thr Val Ile
        35                  40                  45

Thr Val Thr Leu Lys Tyr Lys Gln Leu Arg Gln Pro Leu Asn Phe Ala
    50                  55                  60

Leu Val Asn Leu Ala Val Ala Asp Leu Gly Cys Ala Val Phe Gly Gly
65                  70                  75                  80

Leu Pro Thr Val Val Thr Asn Ala Met Gly Tyr Phe Ser Leu Gly Arg
                85                  90                  95

Val Gly Cys Val Leu Glu Gly Phe Ala Val Ala Phe Phe Gly Ile Ala
            100                 105                 110

Ala Leu Cys Ser Val Ala Val Ile Ala Leu Glu Arg Cys Met Val Val
        115                 120                 125

Cys Arg Pro Val Gly Ser Ile Ser Phe Gln Thr Arg His Ala Val Phe
```

-continued

---

```
      130              135              140
```

```
Gly Val Ala Val Ser Trp Val Trp Ser Phe Ile Trp Asn Thr Pro Pro
145              150              155              160

Leu Phe Gly Trp Gly Arg Phe Glu Leu Glu Gly Val Arg Thr Ser Cys
                 165              170              175

Ala Pro Asp Trp Tyr Ser Arg Asp Leu Ala Asn Val Ser Phe Ile Val
                 180              185              190

Cys Tyr Phe Leu Leu Cys Phe Ala Leu Pro Phe Ser Val Ile Val Tyr
                 195              200              205

Ser Tyr Thr Arg Leu Leu Trp Thr Leu Arg Gln Val Ser Arg Leu Gln
                 210              215              220

Val Cys Glu Gly Gly Ser Ala Ala Arg Ala Glu Ala Gln Val Ser Cys
225              230              235              240

Met Val Val Val Met Ile Leu Ala Phe Leu Leu Thr Trp Leu Pro Tyr
                 245              250              255

Ala Ser Phe Ala Leu Cys Val Ile Leu Ile Pro Glu Leu Tyr Ile Asp
                 260              265              270

Pro Val Ile Ala Thr Val Pro Met Tyr Leu Thr Lys Ser Ser Thr Val
                 275              280              285

Phe Asn Pro Ile Ile Tyr Ile Phe Met Asn Arg Gln Phe Arg Asp Arg
                 290              295              300

Ala Leu Pro Phe Leu Leu Cys Gly Arg Asn Pro Trp Ala Ala Glu Ala
305              310              315              320

Glu Glu Glu Glu Glu Glu Thr Thr Val Ser Ser Val Ser Arg Ser Thr
                 325              330              335

Ser Val Ser Pro Ala
                 340
```

```
<210> SEQ ID NO 38
<211> LENGTH: 1023
<212> TYPE: DNA
<213> ORGANISM: Artificial sequence
<220> FEATURE:
<223> OTHER INFORMATION: zPP1 na sequence

<400> SEQUENCE: 38
atgcacgagg aaatggaatc agaaacatct acagcggcct ctgggagcat tgctgaggtg      60
atgccccgca ctggatatac catacttgca gtgattatcg gggtctttc agtctgcggt     120 gtaatactga acgtaaccgt tattaccgtc acacttaaat acaaacagtt gcgtcaacct     180
ctgaattttg cgctcgttaa tctggccgta gcagacctgg gatgtgcggt ctttggtggc     240
cttccaacgg ttgtcacaaa tgccatggga tatttctctt tgggccgcgt cggctgcgta     300
ctcgaaggat tcgctgttgc tttcttcggt atcgctgcat tgtgcagcgt cgccgtaatt     360
gctctcgaac ggtgcatggt ggtctgcaga cccgtggggt caatcagttt ccaaaccaga     420
catgccgtgt ttggagttgc cgtgagctgg gtatggtcat ttatctggaa cacacccct     480 ctcttcggtt ggggcaggtt tgaacttgag ggagtgcgga cgagttgcgc tccagattgg     540
tacagtagag atcttgccaa tgtcagcttt atagtttgtt acttcttgct gtgtttgcc     600 ttgcctttct ctgtgattgt atacagctac actcgtttgc tctggacact ccgacaagta     660
tctcggctgc aagtatgtga aggcggttct gcggcacgcg ctgaagctca agtatcctgc     720
atggtagtgg tcatgatact cgcttttctc ctcacttggc tgccatatgc aagtttcgct     780
ttgtgtgtta tcctcatacc tgagctctat atcgaccctg tcatcgccac ggtcccaatg     840
```

-continued

```
tatctcacaa aatcctcaac tgtcttcaac cctatcatct atatatttat gaatcggcag      900
tttagggacc gtgctctccc gtttctgctg tgcgggagaa atccatgggc tgcggaagcc      960
gaggaagaag aagaggaaac aaccgtgtca agcgtcagca ggtccactag cgtaagcccc     1020
gcg                                                                   1023
```

```
<210> SEQ ID NO 39
<211> LENGTH: 618
<212> TYPE: PRT
<213> ORGANISM: Artificial sequence
<220> FEATURE:
<223> OTHER INFORMATION: zPP1 -mScarlet open reading frame AA sequence

<400> SEQUENCE: 39

Met His Glu Glu Met Glu Ser Glu Thr Ser Thr Ala Ala Ser Gly Ser
1               5                   10                  15

Ile Ala Glu Val Met Pro Arg Thr Gly Tyr Thr Ile Leu Ala Val Ile
            20                  25                  30

Ile Gly Val Phe Ser Val Cys Gly Val Ile Leu Asn Val Thr Val Ile
        35                  40                  45

Thr Val Thr Leu Lys Tyr Lys Gln Leu Arg Gln Pro Leu Asn Phe Ala
    50                  55                  60

Leu Val Asn Leu Ala Val Ala Asp Leu Gly Cys Ala Val Phe Gly Gly
65                  70                  75                  80

Leu Pro Thr Val Val Thr Asn Ala Met Gly Tyr Phe Ser Leu Gly Arg
                85                  90                  95

Val Gly Cys Val Leu Glu Gly Phe Ala Val Ala Phe Phe Gly Ile Ala
            100                 105                 110

Ala Leu Cys Ser Val Ala Val Ile Ala Leu Glu Arg Cys Met Val Val
        115                 120                 125

Cys Arg Pro Val Gly Ser Ile Ser Phe Gln Thr Arg His Ala Val Phe
    130                 135                 140

Gly Val Ala Val Ser Trp Val Trp Ser Phe Ile Trp Asn Thr Pro Pro
145                 150                 155                 160

Leu Phe Gly Trp Gly Arg Phe Glu Leu Glu Gly Val Arg Thr Ser Cys
                165                 170                 175

Ala Pro Asp Trp Tyr Ser Arg Asp Leu Ala Asn Val Ser Phe Ile Val
            180                 185                 190

Cys Tyr Phe Leu Leu Cys Phe Ala Leu Pro Phe Ser Val Ile Val Tyr
        195                 200                 205

Ser Tyr Thr Arg Leu Leu Trp Thr Leu Arg Gln Val Ser Arg Leu Gln
    210                 215                 220

Val Cys Glu Gly Gly Ser Ala Ala Arg Ala Glu Ala Gln Val Ser Cys
225                 230                 235                 240

Met Val Val Val Met Ile Leu Ala Phe Leu Leu Thr Trp Leu Pro Tyr
                245                 250                 255

Ala Ser Phe Ala Leu Cys Val Ile Leu Ile Pro Glu Leu Tyr Ile Asp
            260                 265                 270

Pro Val Ile Ala Thr Val Pro Met Tyr Leu Thr Lys Ser Ser Thr Val
        275                 280                 285

Phe Asn Pro Ile Ile Tyr Ile Phe Met Asn Arg Gln Phe Arg Asp Arg
    290                 295                 300

Ala Leu Pro Phe Leu Leu Cys Gly Arg Asn Pro Trp Ala Ala Glu Ala
305                 310                 315                 320

Glu Glu Glu Glu Glu Glu Thr Thr Val Ser Ser Val Ser Arg Ser Thr
```

-continued

```
                    325                 330                 335
Ser Val Ser Pro Ala Thr Glu Thr Ser Gln Val Ala Pro Ala Pro Arg
            340                 345                 350
Ala Arg Asp Pro Thr Gly Lys Ser Arg Ile Thr Ser Glu Gly Glu Tyr
            355                 360                 365
Ile Pro Leu Asp Gln Ile Asp Ile Asn Val Val Met Val Ser Lys Gly
        370                 375                 380
Glu Ala Val Ile Lys Glu Phe Met Arg Phe Lys Val His Met Glu Gly
385                 390                 395                 400
Ser Met Asn Gly His Glu Phe Glu Ile Glu Gly Glu Gly Glu Gly Arg
                405                 410                 415
Pro Tyr Glu Gly Thr Gln Thr Ala Lys Leu Lys Val Thr Lys Gly Gly
            420                 425                 430
Pro Leu Pro Phe Ser Trp Asp Ile Leu Ser Pro Gln Phe Met Tyr Gly
            435                 440                 445
Ser Arg Ala Phe Thr Lys His Pro Ala Asp Ile Pro Asp Tyr Tyr Lys
        450                 455                 460
Gln Ser Phe Pro Glu Gly Phe Lys Trp Glu Arg Val Met Asn Phe Glu
465                 470                 475                 480
Asp Gly Gly Ala Val Thr Val Thr Gln Asp Thr Ser Leu Glu Asp Gly
                485                 490                 495
Thr Leu Ile Tyr Lys Val Lys Leu Arg Gly Thr Asn Phe Pro Pro Asp
            500                 505                 510
Gly Pro Val Met Gln Lys Lys Thr Met Gly Trp Glu Ala Ser Thr Glu
            515                 520                 525
Arg Leu Tyr Pro Glu Asp Gly Val Leu Lys Gly Asp Ile Lys Met Ala
        530                 535                 540
Leu Arg Leu Lys Asp Gly Gly Arg Tyr Leu Ala Asp Phe Lys Thr Thr
545                 550                 555                 560
Tyr Lys Ala Lys Lys Pro Val Gln Met Pro Gly Ala Tyr Asn Val Asp
                565                 570                 575
Arg Lys Leu Asp Ile Thr Ser His Asn Glu Asp Tyr Thr Val Val Glu
            580                 585                 590
Gln Tyr Glu Arg Ser Glu Gly Arg His Ser Thr Gly Gly Met Asp Glu
            595                 600                 605
Leu Tyr Lys Phe Cys Tyr Glu Asn Glu Val
        610                 615
```

```
<210> SEQ ID NO 40
<211> LENGTH: 1857
<212> TYPE: DNA
<213> ORGANISM: Artificial sequence
<220> FEATURE:
<223> OTHER INFORMATION: zPP1 -mScarlet open reading frame NA sequence

<400> SEQUENCE: 40
atgcacgagg aaatggaatc agaaacatct acagcggcct ctgggagcat tgctgaggtg      60
atgccccgca ctggatatac catacttgca gtgattatcg gggtcttttc agtctgcggt     120
gtaatactga acgtaaccgt tattaccgtc acacttaaat acaaacagtt gcgtcaacct     180
ctgaattttg cgctcgttaa tctggccgta gcagacctgg gatgtgcggt ctttggtggc     240
cttccaacgg ttgtcacaaa tgccatggga tatttctctt tgggccgcgt cggctgcgta     300
ctcgaaggat tcgctgttgc tttcttcggt atcgctgcat tgtgcagcgt cgccgtaatt     360
gctctcgaac ggtgcatggt ggtctgcaga cccgtggggt caatcagttt ccaaaccaga     420
```

-continued

```
catgccgtgt ttggagttgc cgtgagctgg gtatggtcat ttatctggaa cacacccct    480 ctcttcggtt ggggcaggtt tgaacttgag ggagtgcgga cgagttgcgc tccagattgg    540
tacagtagag atcttgccaa tgtcagcttt atagtttgtt acttcttgct gtgttttgcc    600
ttgcctttct ctgtgattgt atacagctac actcgtttgc tctggacact ccgacaagta    660
tctcggctgc aagtatgtga aggcggttct gcggcacgcg ctgaagctca agtatcctgc    720
atggtagtgg tcatgatact cgctttttctc ctcacttggc tgccatatgc aagtttcgct    780
ttgtgtgtta tcctcatacc tgagctctat atcgaccctg tcatcgccac ggtcccaatg    840
tatctcacaa aatcctcaac tgtcttcaac cctatcatct atatatttat gaatcggcag    900
tttagggacc gtgctctccc gtttctgctg tgcgggagaa atccatgggc tgcggaagcc    960
gaggaagaag aagaggaaac aaccgtgtca agcgtcagca ggtccactag cgtaagcccc   1020
gcgacagaaa caagtcaagt tgcgcccgcc ccgcgagccc gagatccaac cggtaagagc   1080
aggatcacca gcgagggcga gtacatcccc ctggaccaga tcgacatcaa cgtggtgatg   1140
gtgagcaagg gcgaggcagt gatcaaggag ttcatgcggt tcaaggtgca catggagggc   1200
tccatgaacg gccacgagtt cgagatcgag ggcgagggcg agggccgccc ctacgagggc   1260
acccagaccg ccaagctgaa ggtgaccaag ggtggccccc tgcccttctc ctgggacatc   1320
ctgtcccctc agttcatgta cggctccagg gccttcacca gcacccccgc cgacatcccc   1380
gactactata agcagtcctt ccccgagggc ttcaagtggg agcgcgtgat gaacttcgag   1440
gacggcggcg ccgtgaccgt gacccaggac acctccctgg aggacggcac cctgatctac   1500
aaggtgaagc tccgcggcac caacttccct cctgacggcc ccgtaatgca gaagaagaca   1560
atgggctggg aagcgtccac cgagcggttg taccccgagg acggcgtgct gaagggcgac   1620
attaagatgg ccctgcgcct gaaggacggc ggacgctacc tggcggactt caagaccacc   1680
tacaaggcca agaagcccgt gcagatgccc ggcgcctaca cgtcgaccg caagttggac   1740 atcacctccc acaacgagga ctacaccgtg gtggaacagt acgaacgctc cgagggccgc   1800
cactccaccg gcggcatgga cgagctgtac aagttctgct acgagaacga ggtgtaa      1857
```

<210> SEQ ID NO 41
<211> LENGTH: 336
<212> TYPE: PRT
<213> ORGANISM: Artificial sequence
<220> FEATURE:
<223> OTHER INFORMATION: pPP2 aa sequence

<400> SEQUENCE: 41

```
Met Lys Pro Ser Ala Phe Tyr Leu Asn Ala Ser Leu Tyr Leu Gly Pro
1               5                   10                  15

Gln Gly Glu Pro Pro Leu Pro Arg Ser Gly Phe Ile Ala Leu Ser Val
            20                  25                  30

Ile Met Ala Leu Leu Thr Gly Pro Ala Ile Val Leu Asn Ala Thr Val
        35                  40                  45

Ile Ile Val Ser Leu Met His Lys Gln Leu Arg Gln Pro Leu Asn Tyr
    50                  55                  60

Ala Leu Val Asn Met Ala Val Ala Asp Leu Gly Thr Ala Met Thr Gly
65                  70                  75                  80

Gly Leu Leu Ser Val Val Asn Asn Ala Gln Gly Tyr Phe Ser Leu Gly
                85                  90                  95

Arg Thr Gly Cys Val Leu Glu Gly Phe Ala Val Ser Leu Cys Gly Ile
            100                 105                 110
```

-continued

```
Ala Ser Leu Cys Thr Val Ala Leu Ile Ala Val Glu Arg Met Phe Val
        115                 120                 125

Ile Cys Lys Pro Leu Gly Gln Met Gln Phe Gln Lys Gln His Ala Leu
    130                 135                 140

Gly Gly Ile Ala Leu Ala Trp Leu Trp Ser Leu Thr Trp Asn Leu Pro
145                 150                 155                 160

Pro Leu Phe Gly Trp Gly Arg Tyr Glu Leu Glu Gly Val Gly Thr Ser
                165                 170                 175

Cys Ala Pro Asp Trp His Ser Arg Glu Pro Gln Asn Val Ser Tyr Val
            180                 185                 190

Leu Ala Tyr Phe Thr Val Cys Phe Ala Ala Pro Phe Val Ile Ile Leu
        195                 200                 205

Val Ser Tyr Ser Lys Leu Met Trp Thr Leu His Lys Val Thr Lys Met
    210                 215                 220

Ala Cys Met Glu Gly Gly Ala Val Ala Lys Ser Glu Met Thr Val Ala
225                 230                 235                 240

Tyr Met Val Ile Leu Met Val Val Thr Phe Leu Ile Ser Trp Leu Pro
                245                 250                 255

Tyr Ala Gly Leu Ser Met Leu Val Val Leu Ser Pro Asp Val Lys Ile
            260                 265                 270

His Pro Leu Val Gly Thr Val Pro Val Tyr Leu Ala Lys Ser Ser Thr
        275                 280                 285

Val Tyr Asn Pro Ile Ile Tyr Ile Tyr Leu Asn Lys Gln Phe Arg Lys
    290                 295                 300

Tyr Ala Val Pro Phe Leu Leu Cys Gly Arg Glu Leu Glu Met Glu Asp
305                 310                 315                 320

Glu Leu Ser Met Thr Thr Val Glu Thr Ser Asn Arg Val Ser Pro Ala
                325                 330                 335
```

<210> SEQ ID NO 42
<211> LENGTH: 1008
<212> TYPE: DNA
<213> ORGANISM: Artificial sequence
<220> FEATURE:
<223> OTHER INFORMATION: pPP2 na sequence

<400> SEQUENCE: 42

```
atgaagcctt ctgcattcta cctaaatgca agtctgtacc tcgggccaca gggagagccc      60
ccactgcctc ggagtggctt tattgctctg tctgtgatca tggctttgct cacaggtcca     120
gccatagtct tgaacgctac agtgataatc gtgtccctca tgcataaaca actaaggcag     180
cctttgaatt atgcgctcgt taatatggca gtggccgatc ttggtacagc tatgacgggc     240
ggcctgctgt ctgtggtgaa taatgcgcaa ggatacttta gcctgggcag aacaggttgc     300
gtactggaag gttttgctgt tagtctctgc ggcattgcat ctctgtgtac ggtggcactg     360
atcgccgtcg aacgcatgtt cgtcatttgt aaacctctgg gccaaatgca attccaaaag     420
cagcacgcat gggcggcat cgccctggct tggctttggt ctctgacatg gaatctccca     480
cccctctttg ggtggggcag atatgaactt gagggtgtgg gcacctcatg cgcgcccgac     540
tggcatagcc gggagccaca aaatgtatca tacgtccttg cttatttcac tgtgtgtttt     600
gccgcaccat ttgttatcat tctggtctca tatagcaaac tgatgtggac tctgcacaaa     660
gtcactaaaa tggcttgtat ggaaggtgga gcagtcgcaa agtctgaaat gaccgtggcc     720
tacatggtta tcctcatggt agttacattc ttgatcagct ggctcccta cgccgggctc     780
```

-continued

```
agcatgctcg tggttctcag cccggatgtg aagatacacc cgcttgtggg tactgttcct      840
gtgtacctgg ctaaatcctc tacagtatac aatcccatca tttacattta tttgaacaaa      900
caattccgca agtacgccgt cccatttctg ctctgcggcc gggaactcga aatggaagac      960
gagctttcca tgactacagt agaaactagc aatagagtta gccctgcc                 1008
```

<210> SEQ ID NO 43
<211> LENGTH: 613
<212> TYPE: PRT
<213> ORGANISM: Artificial sequence
<220> FEATURE:
<223> OTHER INFORMATION: pPP2 -mScarlet open reading frame AA sequence

<400> SEQUENCE: 43

```
Met Lys Pro Ser Ala Phe Tyr Leu Asn Ala Ser Leu Tyr Leu Gly Pro
1               5                   10                  15

Gln Gly Glu Pro Pro Leu Pro Arg Ser Gly Phe Ile Ala Leu Ser Val
            20                  25                  30

Ile Met Ala Leu Leu Thr Gly Pro Ala Ile Val Leu Asn Ala Thr Val
        35                  40                  45

Ile Ile Val Ser Leu Met His Lys Gln Leu Arg Gln Pro Leu Asn Tyr
    50                  55                  60

Ala Leu Val Asn Met Ala Val Ala Asp Leu Gly Thr Ala Met Thr Gly
65                  70                  75                  80

Gly Leu Leu Ser Val Val Asn Asn Ala Gln Gly Tyr Phe Ser Leu Gly
                85                  90                  95

Arg Thr Gly Cys Val Leu Glu Gly Phe Ala Val Ser Leu Cys Gly Ile
            100                 105                 110

Ala Ser Leu Cys Thr Val Ala Leu Ile Ala Val Glu Arg Met Phe Val
        115                 120                 125

Ile Cys Lys Pro Leu Gly Gln Met Gln Phe Gln Lys Gln His Ala Leu
    130                 135                 140

Gly Gly Ile Ala Leu Ala Trp Leu Trp Ser Leu Thr Trp Asn Leu Pro
145                 150                 155                 160

Pro Leu Phe Gly Trp Gly Arg Tyr Glu Leu Glu Gly Val Gly Thr Ser
                165                 170                 175

Cys Ala Pro Asp Trp His Ser Arg Glu Pro Gln Asn Val Ser Tyr Val
            180                 185                 190

Leu Ala Tyr Phe Thr Val Cys Phe Ala Ala Pro Phe Val Ile Ile Leu
        195                 200                 205

Val Ser Tyr Ser Lys Leu Met Trp Thr Leu His Lys Val Thr Lys Met
    210                 215                 220

Ala Cys Met Glu Gly Gly Ala Val Ala Lys Ser Glu Met Thr Val Ala
225                 230                 235                 240

Tyr Met Val Ile Leu Met Val Val Thr Phe Leu Ile Ser Trp Leu Pro
                245                 250                 255

Tyr Ala Gly Leu Ser Met Leu Val Val Leu Ser Pro Asp Val Lys Ile
            260                 265                 270

His Pro Leu Val Gly Thr Val Pro Val Tyr Leu Ala Lys Ser Ser Thr
        275                 280                 285

Val Tyr Asn Pro Ile Ile Tyr Ile Tyr Leu Asn Lys Gln Phe Arg Lys
    290                 295                 300

Tyr Ala Val Pro Phe Leu Leu Cys Gly Arg Glu Leu Glu Met Glu Asp
305                 310                 315                 320

Glu Leu Ser Met Thr Thr Val Glu Thr Ser Asn Arg Val Ser Pro Ala
```

```
              325              330              335
Thr Glu Thr Ser Gln Val Ala Pro Ala Pro Arg Ala Arg Asp Pro Thr
         340              345              350
Gly Lys Ser Arg Ile Thr Ser Glu Gly Glu Tyr Ile Pro Leu Asp Gln
         355              360              365
Ile Asp Ile Asn Val Val Met Val Ser Lys Gly Glu Ala Val Ile Lys
     370              375              380
Glu Phe Met Arg Phe Lys Val His Met Glu Gly Ser Met Asn Gly His
385              390              395              400
Glu Phe Glu Ile Glu Gly Glu Gly Glu Gly Arg Pro Tyr Glu Gly Thr
              405              410              415
Gln Thr Ala Lys Leu Lys Val Thr Lys Gly Gly Pro Leu Pro Phe Ser
         420              425              430
Trp Asp Ile Leu Ser Pro Gln Phe Met Tyr Gly Ser Arg Ala Phe Thr
         435              440              445
Lys His Pro Ala Asp Ile Pro Asp Tyr Tyr Lys Gln Ser Phe Pro Glu
     450              455              460
Gly Phe Lys Trp Glu Arg Val Met Asn Phe Glu Asp Gly Gly Ala Val
465              470              475              480
Thr Val Thr Gln Asp Thr Ser Leu Glu Asp Gly Thr Leu Ile Tyr Lys
              485              490              495
Val Lys Leu Arg Gly Thr Asn Phe Pro Pro Asp Gly Pro Val Met Gln
         500              505              510
Lys Lys Thr Met Gly Trp Glu Ala Ser Thr Glu Arg Leu Tyr Pro Glu
         515              520              525
Asp Gly Val Leu Lys Gly Asp Ile Lys Met Ala Leu Arg Leu Lys Asp
     530              535              540
Gly Gly Arg Tyr Leu Ala Asp Phe Lys Thr Thr Tyr Lys Ala Lys Lys
545              550              555              560
Pro Val Gln Met Pro Gly Ala Tyr Asn Val Asp Arg Lys Leu Asp Ile
              565              570              575
Thr Ser His Asn Glu Asp Tyr Thr Val Val Glu Gln Tyr Glu Arg Ser
              580              585              590
Glu Gly Arg His Ser Thr Gly Gly Met Asp Glu Leu Tyr Lys Phe Cys
              595              600              605
Tyr Glu Asn Glu Val
         610
```

<210> SEQ ID NO 44
<211> LENGTH: 1842
<212> TYPE: DNA
<213> ORGANISM: Artificial sequence
<220> FEATURE:
<223> OTHER INFORMATION: pPP2 -mScarlet open reading frame NA sequence

<400> SEQUENCE: 44

```
atgaagcctt ctgcattcta cctaaatgca agtctgtacc tcgggccaca gggagagccc      60
ccactgcctc ggagtggctt tattgctctg tctgtgatca tggctttgct cacaggtcca     120
gccatagtct tgaacgctac agtgataatc gtgtccctca tgcataaaca actaaggcag     180
cctttgaatt atgcgctcgt taatatggca gtggccgatc ttggtacagc tatgacgggc     240
ggcctgctgt ctgtggtgaa taatgcgcaa ggatacttta gcctgggcag aacaggttgc     300
gtactggaag gttttgctgt tagtctctgc ggcattgcat ctctgtgtac ggtggcactg     360
atcgccgtcg aacgcatgtt cgtcatttgt aaacctctgg ccaaatgca attccaaaag     420
```

99　　　　　　　　　　　　　　　　　　　　　　　　　　　　　　100

-continued

```
cagcacgcat tgggcggcat cgccctggct tggctttggt ctctgacatg gaatctccca      480
cccctctttg ggtggggcag atatgaactt gagggtgtgg gcacctcatg cgcgcccgac      540
tggcatagcc gggagccaca aaatgtatca tacgtccttg cttatttcac tgtgtgtttt      600
gccgcaccat ttgttatcat tctggtctca tatagcaaac tgatgtggac tctgcacaaa      660
gtcactaaaa tggcttgtat ggaaggtgga gcagtcgcaa agtctgaaat gaccgtggcc      720
tacatggtta tcctcatggt agttacattc ttgatcagct ggctcccta cgccgggctc       780 agcatgctcg tggttctcag cccggatgtg aagatacacc cgcttgtggg tactgttcct      840
gtgtacctgg ctaaatcctc tacagtatac aatcccatca tttacatta tttgaacaaa       900 caattccgca agtacgccgt cccatttctg ctctgcggcc gggaactcga aatggaagac      960
gagctttcca tgactacagt agaaactagc aatagagtta gccctgccac agaaactagt     1020
caagtagccc ctgctccgcg agcccgagat ccaaccggta agagcaggat caccagcgag     1080
ggcgagtaca tcccccctgga ccagatcgac atcaacgtgg tgatggtgag caagggcgag    1140
gcagtgatca aggagttcat gcggttcaag gtgcacatgg agggctccat gaacggccac     1200
gagttcgaga tcgagggcga gggcgagggc cgcccctacg agggcacccca gaccgccaag    1260 ctgaaggtga ccaagggtgg cccccctgccc ttctcctggg acatcctgtc ccctcagttc    1320
atgtacggct ccagggcctt caccaagcac cccgccgaca tccccgacta ctataagcag     1380
tccttccccg agggcttcaa gtgggagcgc gtgatgaact tcgaggacgg cggcgccgtg     1440
accgtgaccc aggacacctc cctggaggac ggcaccctga tctacaaggt gaagctccgc     1500
ggcaccaact ccctcctga cggcccccgta atgcagaaga agacaatggg ctgggaagcg     1560
tccaccgagc ggttgtaccc cgaggacggc gtgctgaagg cgacattaa gatggccctg     1620 cgcctgaagg acggcggacg ctacctggcg gacttcaaga ccacctacaa ggccaagaag     1680
cccgtgcaga tgcccggcgc ctacaacgtc gaccgcaagt tggacatcac ctcccacaac    1740
gaggactaca ccgtggtgga acagtacgaa cgctccgagg gccgccactc caccggcggc    1800
atggacgagc tgtacaagtt ctgctacgag aacgaggtgt aa                       1842
```